United States Patent
Bogner et al.

(10) Patent No.: US 10,968,492 B2
(45) Date of Patent: Apr. 6, 2021

(54) HPPD-INHIBITOR HERBICIDE TOLERANCE

(71) Applicant: PIONEER HI-BRED INTERNATIONAL, INC., Johnston, IA (US)

(72) Inventors: Mark Bogner, Kalaheo, HI (US); Julian Chaky, Urbandale, IA (US); Jennifer A. Klaiber, Urbandale, IA (US); Donald Kyle, Princeton, IL (US); Mark D. Vogt, Ankeny, IA (US)

(73) Assignee: PIONEER HI-BRED INTERNATIONAL, INC.

( * ) Notice: Subject to any disclaimer, the term of this patent is extended or adjusted under 35 U.S.C. 154(b) by 420 days.

(21) Appl. No.: 15/916,735

(22) Filed: Mar. 9, 2018

(65) Prior Publication Data
US 2018/0201949 A1    Jul. 19, 2018

Related U.S. Application Data

(62) Division of application No. 13/013,332, filed on Jan. 25, 2011, now Pat. No. 9,970,021.

(60) Provisional application No. 61/371,392, filed on Aug. 6, 2010, provisional application No. 61/371,454, filed on Aug. 6, 2010, provisional application No. 61/298,523, filed on Jan. 26, 2010, provisional application No. 61/298,528, filed on Jan. 26, 2010.

(51) Int. Cl.
*C12Q 1/6895* (2018.01)
*A01H 1/04* (2006.01)

(52) U.S. Cl.
CPC ............. *C12Q 1/6895* (2013.01); *A01H 1/04* (2013.01); *C12Q 2600/13* (2013.01); *C12Q 2600/156* (2013.01); *C12Q 2600/172* (2013.01)

(58) Field of Classification Search
CPC ................................ C12Q 1/6895; A01H 1/04
See application file for complete search history.

(56) References Cited

U.S. PATENT DOCUMENTS

| | | |
|---|---|---|
| 476,137 A | 5/1892 | Eustis |
| 5,013,659 A | 5/1991 | Bedbrook et al. |
| 5,141,870 A | 8/1992 | Bedbrook et al. |
| 5,304,732 A | 4/1994 | Anderson et al. |
| 5,331,107 A | 7/1994 | Anderson et al. |
| 5,378,824 A | 1/1995 | Bedbrook et al. |
| 5,489,520 A | 2/1996 | Adams et al. |
| 5,550,318 A | 8/1996 | Adams et al. |
| 5,561,236 A | 10/1996 | Leemans et al. |
| 5,605,011 A | 2/1997 | Bedbrook et al. |
| 5,646,024 A | 7/1997 | Leemans et al. |
| 5,648,477 A | 7/1997 | Leemans et al. |
| 5,731,180 A | 3/1998 | Dietrich |
| 5,750,853 A | 5/1998 | Fuller et al. |
| 5,767,361 A | 6/1998 | Dietrich |
| 5,767,373 A | 6/1998 | Ward et al. |
| 5,852,226 A | 12/1998 | Fuller et al. |
| 5,874,265 A | 2/1999 | Adams et al. |
| 5,879,903 A | 3/1999 | Strauch |
| 5,919,675 A | 7/1999 | Adams et al. |
| 5,928,937 A | 7/1999 | Kakefuda et al. |
| 5,969,213 A | 10/1999 | Adams et al. |
| 6,069,115 A | 5/2000 | Pallet et al. |
| 6,177,616 B1 | 1/2001 | Bartsch et al. |
| 6,245,968 B1 | 7/2001 | Boudoc et al. |
| 6,268,549 B1 | 7/2001 | Sailland et al. |
| 6,282,837 B1 | 9/2001 | Ward et al. |
| 6,288,306 B1 | 9/2001 | Ward et al. |
| 6,307,129 B1 | 10/2001 | Ward et al. |
| 2006/0041951 A1 | 2/2006 | Sebastian et al. |
| 2010/0024080 A1 | 1/2010 | Kyle et al. |
| 2010/0186131 A1* | 7/2010 | Chaky ............... C12N 15/8274 800/312 |

FOREIGN PATENT DOCUMENTS

| | | |
|---|---|---|
| WO | 1996/033270 | 10/1996 |
| WO | 1999/023886 | 5/1999 |
| WO | 2001/012825 | 2/2001 |
| WO | 2005/107437 | 11/2005 |
| WO | 2006/017840 | 2/2006 |

(Continued)

OTHER PUBLICATIONS

Young et al, Weed Technology (2003) 17:651-654.*
Song et al, Theor. Appl. Genetics (2004) 109: 122-128.*
Choi, et al., "A soybean transcript map: Gene distribution, haplotype and single nucleotide polymorphism analysis", Genetics, vol. 176, pp. 685-696 (2007).
Cregan, P.B., et al. "An integrated genetic linkage map of the soybean genome", Crop Science, vol. 39, pp. 1464-1490 (1990).
Dayan et al., "Soybean (*Glycine max*) cultivar differences in response to sulfentrazone", Weed Science, vol. 45, pp. 634-641 (1997).
Henikoff, et al., "Amino acid substitution matrices from protein blocks" Proc. Natl. Acad. Sci. USA, vol. 89, pp. 10915-10919 (1992).

(Continued)

*Primary Examiner* — Mykola V. Kovalenko

(57) ABSTRACT

This invention relates generally to the detection of genetic differences among soybeans. More particularly, the invention relates to soybean quantitative trait loci (QTL) for tolerance or sensitivity to HPPD-inhibitor herbicides, such as mesotrione and isoxazole herbicides, to soybean plants possessing these QTLs, which map to a novel chromosomal region, and to genetic markers that are indicative of phenotypes associated with tolerance, improved tolerance, susceptibility, or increased susceptibility. Methods and compositions for use of these markers in genotyping of soybean and selection are also disclosed, as are methods and compositions for use of these markers in selection and use of herbicides for weed control. Also disclosed are isolated polynucleotides and polypeptides relating to such tolerance or sensitivity and methods of introgres sing such tolerance into a plant by breeding or transgenically or by a combination thereof. Plant cells, plants, and seeds produced are also provided.

3 Claims, 1 Drawing Sheet

Specification includes a Sequence Listing.

(56) References Cited

FOREIGN PATENT DOCUMENTS

WO     2010/011803     1/2010

OTHER PUBLICATIONS

Herman, et al., "A Three-component Dicamba O-Demethylase from Pseudomonas maltophilia, Strain DI-6: Gene Isolation . . . ", J. Biol. Chem., vol. 280, pp. 24759-24767 (2005).
Hulting, et al., "Soybean (*Glycine max* (L.) Merr.) cultivar tolerance to sulfentrazone", Science Direct, vol. 20, pp. 679-683 (2001).
Li, Z., et al., "Physiological basis for the differentials tolerance of Glycine max to sulfentrazone during seed germination", Weed Science, vol. 48, pp. 281-285 (2000).
Li, Z., et al., "Using electrolyte leakage to detect soybean (*Glycine max* cultivars sensitive to sulfentrazone", Weed Technology, vol. 14, pp. 699-704 (2000).
Needleman, et al., "A general method applicable to the search for similarities in the amino acid sequence of two proteins", J. Mol. Biol., vol. 48, pp. 443-453 (1970).
Retzinger, et al., "Classification of herbicides by site of action for weed resistance management strategies", Weed Technology, vol. 11, pp. 383-393 (1997).
Shoemaker, et al., "Molecular linkage map of soybean (*Glycine max* L. Merr.)", pp. 6.131-6.138 (1993), In S.J. O'Brien (ed.) Genetic Maps of Complex Genomes . . . .
Shoemaker, R.C., "RFLP map of soybean", pp. 299-309 (1994), In R.L. Phillips and I.K. Vasil (eds.) DNA based markers in plants. Kluwer Academic Pres Dordrecht, Netherlands.
Swantek, J.M., et al., "Evaluation of soybean injury from sulentrazone and inheritance of tolerance", Weed Science, vol. 46, p. 271-277 (1998).
Taylor-Lovell, et al., "Phytosic response and yield of soybean (*Glycine max*) varieties treated with sulfentrazone or flumioxazin", Weed Technology, vol. 15, pp. 95-102 (2001).
International Search Report in PCT/US2009/051483, dated Oct. 13, 2009.
Copending U.S. Appl. No. 12/506,498, filed Jul. 21, 2009.
Copending U.S. Appl. No. 12/694,255, filed Jan. 26, 2010.
Copending U.S. Appl. No. 13/013,139, filed Jan. 25, 2011.

\* cited by examiner

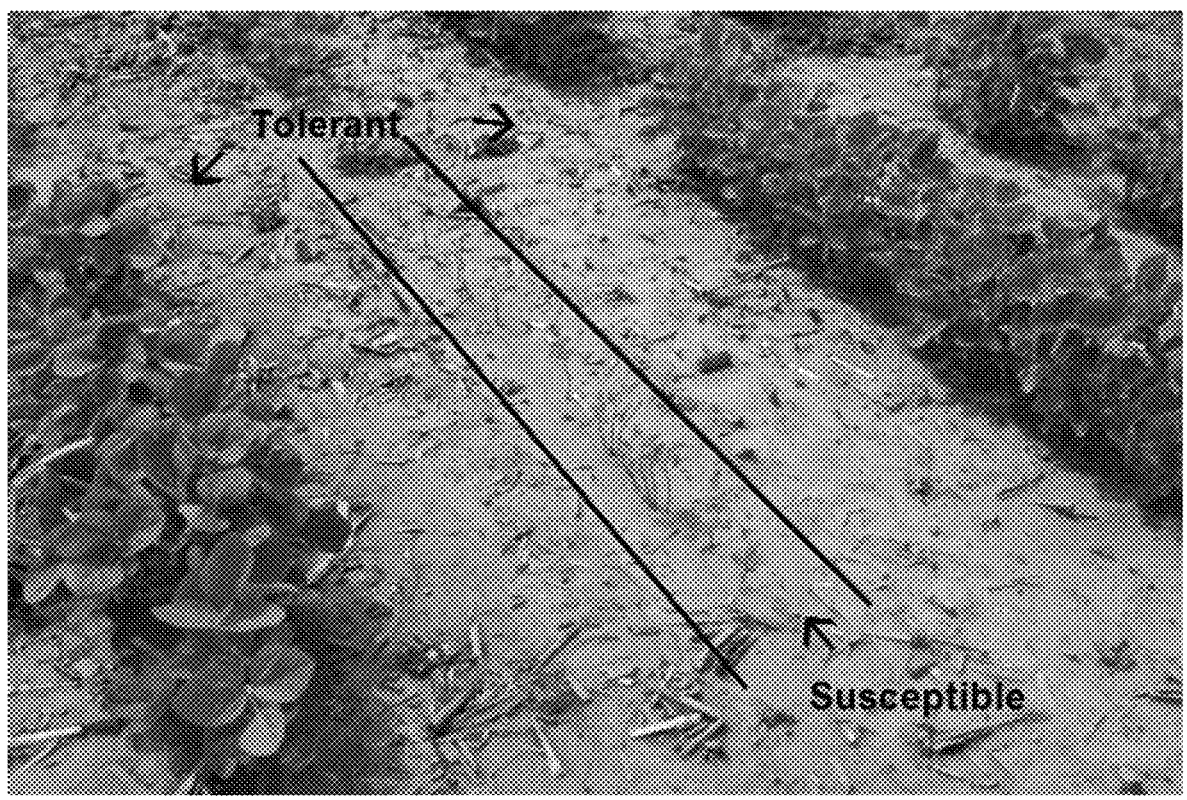

HPPD-INHIBITOR HERBICIDE TOLERANCE

FIELD OF THE INVENTION

This invention relates generally to the detection of genetic differences among soybeans.

BACKGROUND OF THE INVENTION

Soybeans (*Glycine max* L. Merr.) are a major cash crop and investment commodity in North America and elsewhere. Soybean oil is one of the most widely used edible oils, and soybeans are used worldwide both in animal feed and in human food production. Additionally, soybean utilization is expanding to industrial, manufacturing, and pharmaceutical applications. Weed management in soybean fields is important to maximizing yields. A recent development in soybean technology has been the development of herbicide-tolerant soybean varieties. Glyphosate tolerant soybeans were commercially introduced in 1996 and accounted for more than 85% percent of U.S. soybean acreage in 2007.

Some weeds are starting to show increased tolerance to glyphosate. This increased tolerance decreases the effectiveness of glyphosate application and results in lower yields for farmers. As a result there is a need in the art for soybean varieties that are tolerant to other herbicide chemistry.

SUMMARY OF THE INVENTION

This invention relates generally to the detection of genetic differences among soybeans. More particularly, the invention relates to soybean quantitative trait loci (QTL) for tolerance or sensitivity to mesotrione and/or isoxazole herbicides, to soybean plants possessing these QTLs, which map to a novel chromosomal region, and to genetic markers that are indicative of phenotypes associated with mesotrione and/or isoxazole herbicide tolerance. Methods and compositions for use of these markers in genotyping, screening, and selection of soybean are also disclosed.

A novel method is provided for determining the presence or absence in soybean germplasm of a QTL associated with tolerance or susceptibility to HPPD-inhibitor herbicides, including mesotrione and/or isoxazole herbicides. The trait has been found to be closely linked to a number of molecular markers that map to linkage group L, on chromosome 19 (Gm19). Soybean plants, seeds, tissue cultures, variants and mutants having tolerance or susceptibility to HPPD-inhibitor herbicides, including mesotrione and/or isoxazole herbicides, produced by the foregoing methods are also provided.

The QTL associated with tolerance or sensitivity to mesotrione and/or isoxazole herbicides maps to soybean linkage group L. The QTL may be mapped by one or more molecular markers, including SATT495, P10649C-3, SATT182, SATT388, SATT313, SATT613, and markers closely linked thereto. Other markers of linkage group L may also be used to identify the presence or absence of the gene, including other markers above marker SATT613. Additional relevant markers on linkage group L include S03859-1-A, S08103-1-Q1, S08104-1-Q1, S08106-1-Q1, S08110-1-Q1, S08111-1-Q1, S08115-2-Q1, S08117-1-Q1, S08119-1-Q1, S08118-1-Q1, S08116-1-Q1, S08114-1-Q1, S08113-1-Q1, S08112-1-Q1, S08108-1-Q1, S08101-2-Q1, S08101-3-Q1, S08101-4-Q1, S08105-1-Q1, S08102-1-Q1, S08107-1-Q1, S08109-1-Q1, and S08101-1-Q1, or markers closely linked thereto (see, e.g., Tables A and B below). Other markers of linkage group L may also be used to identify the presence or absence of the gene, including other markers above marker SATT613.

The information disclosed herein regarding the QTL for tolerance or sensitivity to mesotrione and/or isoxazole herbicides which maps to soybean linkage group L is used to aid in the selection of breeding plants, lines, and populations containing tolerance or sensitivity to mesotrione and/or isoxazole herbicides for use in introgression of this trait into elite soybean germplasm, or germplasm of proven genetic superiority suitable for variety release.

Also provided is a method for introgressing a soybean QTL associated with tolerance or sensitivity to mesotrione and/or isoxazole herbicides into non-tolerant soybean germplasm or less tolerant soybean germplasm. According to the method, nucleic acid markers mapping the QTL are used to select soybean plants containing the QTL. Plants so selected have a high probability of expressing the trait tolerance or sensitivity to mesotrione and/or isoxazole herbicides. Plants so selected can be used in a soybean breeding program. Through the process of introgression, the QTL associated with tolerance or sensitivity to mesotrione and/or isoxazole herbicides is introduced from plants identified using marker-assisted selection to other plants. According to the method, agronomically desirable plants and seeds can be produced containing the QTL associated with tolerance or sensitivity to mesotrione and/or isoxazole herbicides from germplasm containing the QTL. Sources of tolerance or sensitivity to mesotrione and/or isoxazole herbicides are disclosed below.

Also provided herein is a method for producing a soybean plant adapted for conferring tolerance or sensitivity to mesotrione and/or isoxazole herbicides. First, donor soybean plants for a parental line containing the tolerance QTL are selected. According to the method, selection can be accomplished via nucleic acid marker-associated selection as explained herein. Selected plant material may represent, among others, an inbred line, a hybrid, a heterogeneous population of soybean plants, or simply an individual plant. According to techniques well known in the art of plant breeding, this donor parental line is crossed with a second parental line. Typically, the second parental line is a high yielding line. This cross produces a segregating plant population composed of genetically heterogeneous plants. Plants of the segregating plant population are screened for the tolerance QTL and are subjected to further breeding. This further breeding may include, among other techniques, additional crosses with other lines, hybrids, backcrossing, or self-crossing. The result is a line of soybean plants that is tolerant to mesotrione and/or isoxazole herbicides, and also has other desirable traits, such as yield, from one or more other soybean lines.

Also provided is a method for introgressing a soybean QTL associated with tolerance or sensitivity to mesotrione and/or isoxazole herbicides into non-tolerant soybean germplasm or less tolerant soybean germplasm. According to the method, nucleic acid markers mapping the QTL are used to select soybean plants containing the QTL. Plants so selected have a high probability of expressing the trait tolerance or sensitivity to mesotrione and/or isoxazole herbicides. Plants so selected can be used in a soybean breeding program. Through the process of introgression, the QTL associated with tolerance or sensitivity to mesotrione and/or isoxazole herbicides is introduced from plants identified using marker-assisted selection to other plants. According to the method, agronomically desirable plants and seeds can be produced containing the QTL associated with tolerance or sensitivity to mesotrione and/or isoxazole herbicides from germplasm containing the QTL. Sources of tolerance or sensitivity to mesotrione and/or isoxazole herbicides are disclosed below.

Soybean plants, seeds, tissue cultures, variants and mutants having tolerance or sensitivity to mesotrione and/or isoxazole herbicides produced by the foregoing methods are also provided. Also provided herein are methods for controlling weeds in a crop by applying to the crop and any weeds affecting such crop an effective amount of such herbicide(s), either pre-emergent or post-emergent, such that the weeds are substantially controlled without substantially negatively impacting the crop. Also provided are compositions useful in the disclosed methods, including polynucleotide primers and probes useful for detecting relevant markers, as well as kits containing the same.

BRIEF DESCRIPTION OF THE DRAWINGS

The invention can be more fully understood from the following detailed description and the accompanying drawings and Sequence Listing, which form a part of this application.

FIG. 1 provides examples of cultivars with vastly different mesotrione and isoxazole herbicide tolerance or sensitivity phenotype. Shown are field samples, with a non-tolerant variety in the center and tolerant varieties on the left and right (normal growth).

SUMMARY OF THE SEQUENCES

SEQ ID NOs: 1-5 comprise nucleotide sequences of regions of the Soybean genome, each capable of being used as a probe or primer, either alone or in combination, for the detection of marker locus P10649C-3 on LG-L. In certain examples, SEQ ID NOs: 1 and 2 are used as primers while SEQ ID NOs: 3-5 are used as probes.

SEQ ID NOs: 6-9 comprise nucleotide sequences of regions of the Soybean genome, each capable of being used as a probe or primer, either alone or in combination, for the detection of marker locus S00224-1 on LG-L. In certain examples, SEQ ID NOs: 6 and 7 are used as primers while SEQ ID NOs: 8 and 9 are used as probes.

SEQ ID NOs: 10-13 comprise nucleotide sequences of regions of the Soybean genome, each capable of being used as a probe or primer, either alone or in combination, for the detection of marker locus P5467-1 on LG-N. In certain examples, SEQ ID NOs: 10 and 11 are used as primers while SEQ ID NOs: 12 and 13 are used as probes.

SEQ ID NOs: 14-17 comprise nucleotide sequences of regions of the Soybean genome, each capable of being used as a probe or primer, either alone or in combination, for the detection of marker locus S08101-1-Q1 on LG-L. In certain examples, SEQ ID NOs: 14 and 15 are used as primers while SEQ ID NOs: 16 and 17 are used as probes.

SEQ ID NOs: 18-21 comprise nucleotide sequences of regions of the Soybean genome, each capable of being used as a probe or primer, either alone or in combination, for the detection of marker locus S08101-2-Q1 on LG-L. In certain examples, SEQ ID NOs: 18 and 19 are used as primers while SEQ ID NOs: 20 and 21 are used as probes.

SEQ ID NOs: 22-25 comprise nucleotide sequences of regions of the Soybean genome, each capable of being used as a probe or primer, either alone or in combination, for the detection of marker locus S08101-3-Q1 on LG-L. In certain examples, SEQ ID NOs: 22 and 23 are used as primers while SEQ ID NOs: 24 and 25 are used as probes.

SEQ ID NOs: 26-29 comprise nucleotide sequences of regions of the Soybean genome, each capable of being used as a probe or primer, either alone or in combination, for the detection of marker locus S08101-4-Q1 on LG-L. In certain examples, SEQ ID NOs: 26 and 27 are used as primers while SEQ ID NOs: 28 and 29 are used as probes.

SEQ ID NOs: 30-33 comprise nucleotide sequences of regions of the Soybean genome, each capable of being used as a probe or primer, either alone or in combination, for the detection of marker locus S08102-1-Q1 on LG-L. In certain examples, SEQ ID NOs: 30 and 31 are used as primers while SEQ ID NOs: 32 and 33 are used as probes.

SEQ ID NOs: 34-37 comprise nucleotide sequences of regions of the Soybean genome, each capable of being used as a probe or primer, either alone or in combination, for the detection of marker locus S08103-1-Q1 on LG-L. In certain examples, SEQ ID NOs: 34 and 35 are used as primers while SEQ ID NOs: 36 and 37 are used as probes.

SEQ ID NOs: 38-41 comprise nucleotide sequences of regions of the Soybean genome, each capable of being used as a probe or primer, either alone or in combination, for the detection of marker locus S08104-1-Q1 on LG-L. In certain examples, SEQ ID NOs: 38 and 39 are used as primers while SEQ ID NOs: 40 and 41 are used as probes.

SEQ ID NOs: 42-45 comprise nucleotide sequences of regions of the Soybean genome, each capable of being used as a probe or primer, either alone or in combination, for the detection of marker locus S08105-1-Q1 on LG-L. In certain examples, SEQ ID NOs: 42 and 43 are used as primers while SEQ ID NOs: 44 and 45 are used as probes.

SEQ ID NOs: 46-49 comprise nucleotide sequences of regions of the Soybean genome, each capable of being used as a probe or primer, either alone or in combination, for the detection of marker locus S08106-1-Q1 on LG-L. In certain examples, SEQ ID NOs: 46 and 47 are used as primers while SEQ ID NOs: 48 and 49 are used as probes.

SEQ ID NOs: 50-53 comprise nucleotide sequences of regions of the Soybean genome, each capable of being used as a probe or primer, either alone or in combination, for the detection of marker locus S08107-1-Q1 on LG-L. In certain examples, SEQ ID NOs: 50 and 51 are used as primers while SEQ ID NOs: 52 and 53 are used as probes.

SEQ ID NOs: 54-57 comprise nucleotide sequences of regions of the Soybean genome, each capable of being used as a probe or primer, either alone or in combination, for the detection of marker locus S08108-1-Q1 on LG-L. In certain examples, SEQ ID NOs: 54 and 55 are used as primers while SEQ ID NOs: 56 and 57 are used as probes.

SEQ ID NOs: 58-61 comprise nucleotide sequences of regions of the Soybean genome, each capable of being used as a probe or primer, either alone or in combination, for the detection of marker locus S08109-1-Q1 on LG-L. In certain examples, SEQ ID NOs: 58 and 59 are used as primers while SEQ ID NOs: 60 and 61 are used as probes.

SEQ ID NOs: 62-65 comprise nucleotide sequences of regions of the Soybean genome, each capable of being used as a probe or primer, either alone or in combination, for the detection of marker locus S08110-1-Q1 on LG-L. In certain examples, SEQ ID NOs: 62 and 63 are used as primers while SEQ ID NOs: 64 and 65 are used as probes.

SEQ ID NOs: 66-69 comprise nucleotide sequences of regions of the Soybean genome, each capable of being used as a probe or primer, either alone or in combination, for the detection of marker locus S08111-1-Q1 on LG-L. In certain examples, SEQ ID NOs: 66 and 67 are used as primers while SEQ ID NOs: 68 and 69 are used as probes.

SEQ ID NOs: 70-73 comprise nucleotide sequences of regions of the Soybean genome, each capable of being used as a probe or primer, either alone or in combination, for the detection of marker locus S08112-1-Q1 on LG-L. In certain examples, SEQ ID NOs: 70 and 71 are used as primers while SEQ ID NOs: 72 and 73 are used as probes.

SEQ ID NOs: 74-77 comprise nucleotide sequences of regions of the Soybean genome, each capable of being used as a probe or primer, either alone or in combination, for the detection of marker locus S08115-2-Q1 on LG-L. In certain examples, SEQ ID NOs: 74 and 75 are used as primers while SEQ ID NOs: 76 and 77 are used as probes.

SEQ ID NOs: 78-81 comprise nucleotide sequences of regions of the Soybean genome, each capable of being used as a probe or primer, either alone or in combination, for the detection of marker locus S08116-1-Q1 on LG-L. In certain examples, SEQ ID NOs: 78 and 79 are used as primers while SEQ ID NOs: 80 and 81 are used as probes.

SEQ ID NOs: 82-85 comprise nucleotide sequences of regions of the Soybean genome, each capable of being used as a probe or primer, either alone or in combination, for the detection of marker locus S08117-1-Q1 on LG-L. In certain examples, SEQ ID NOs: 82 and 83 are used as primers while SEQ ID NOs: 84 and 85 are used as probes.

SEQ ID NOs: 86-89 comprise nucleotide sequences of regions of the Soybean genome, each capable of being used as a probe or primer, either alone or in combination, for the detection of marker locus S08118-1-Q1 on LG-L. In certain examples, SEQ ID NOs: 86 and 87 are used as primers while SEQ ID NOs: 88 and 89 are used as probes.

SEQ ID NOs: 90-93 comprise nucleotide sequences of regions of the Soybean genome, each capable of being used as a probe or primer, either alone or in combination, for the detection of marker locus S08119-1-Q1 on LG-L. In certain examples, SEQ ID NOs: 90 and 91 are used as primers while SEQ ID NOs: 92 and 93 are used as probes.

SEQ ID NOs: 94-97 comprise nucleotide sequences of regions of the Soybean genome, each capable of being used as a probe or primer, either alone or in combination, for the detection of marker locus S04867-1-A on LG-L. In certain examples, SEQ ID NOs: 94 and 95 are used as primers while SEQ ID NOs: 96 and 97 are used as probes.

SEQ ID NOs: 98-101 comprise nucleotide sequences of regions of the Soybean genome, each capable of being used as a probe or primer, either alone or in combination, for the detection of marker locus S03859-1-A on LG-L. In certain examples, SEQ ID NOs: 98 and 99 are used as primers while SEQ ID NOs: 100 and 101 are used as probes.

SEQ ID NOs: 102-105 comprise nucleotide sequences of regions of the Soybean genome, each capable of being used as a probe or primer, either alone or in combination, for the detection of marker locus S08010-1-Q1 on LG-L. In certain examples, SEQ ID NOs: 102 and 103 are used as primers while SEQ ID NOs: 104 and 105 are used as probes.

SEQ ID NOs: 106-109 comprise nucleotide sequences of regions of the Soybean genome, each capable of being used as a probe or primer, either alone or in combination, for the detection of marker locus S08010-2-Q1 on LG-L. In certain examples, SEQ ID NOs: 106 and 107 are used as primers while SEQ ID NOs: 108 and 109 are used as probes.

SEQ ID NOs: 110-113 comprise nucleotide sequences of regions of the Soybean genome, each capable of being used as a probe or primer, either alone or in combination, for the detection of marker locus S08114-1-Q1 on LG-L. In certain examples, SEQ ID NOs: 110 and 111 are used as primers while SEQ ID NOs: 112 and 113 are used as probes.

SEQ ID NOs: 114-117 comprise nucleotide sequences of regions of the Soybean genome, each capable of being used as a probe or primer, either alone or in combination, for the detection of marker locus S08113-1-Q1 on LG-L. In certain examples, SEQ ID NOs: 114 and 115 are used as primers while SEQ ID NOs: 116 and 117 are used as probes.

SEQ ID NOs: 118-121 comprise nucleotide sequences of regions of the Soybean genome, each capable of being used as a probe or primer, either alone or in combination, for the detection of marker locus S08007-1-Q1 on LG-L. In certain examples, SEQ ID NOs: 118 and 119 are used as primers while SEQ ID NOs: 120 and 121 are used as probes.

DETAILED DESCRIPTION

It is to be understood that this invention is not limited to particular embodiments or examples, which can, of course, vary. It is also to be understood that the terminology used herein is for the purpose of describing particular embodiments only, and is not intended to be limiting. Further, all publications referred to herein are incorporated by reference herein for the purpose cited to the same extent as if each was specifically and individually indicated to be incorporated by reference herein.

Definitions

As used in this specification and the appended claims, terms in the singular and the singular forms "a," "an" and "the," for example, include plural referents unless the content clearly dictates otherwise. Thus, for example, reference to "plant," "the plant" or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

Additionally, as used herein, "comprising" is to be interpreted as specifying the presence of the stated features, integers, steps, or components as referred to, but does not preclude the presence or addition of one or more features, integers, steps, or components, or groups thereof. Thus, for example, a kit comprising one pair of oligonucleotide primers may have two or more pairs of oligonucleotide primers. Additionally, the term "comprising" is intended to include examples encompassed by the terms "consisting essentially of" and "consisting of." Similarly, the term "consisting essentially of" is intended to include examples encompassed by the term "consisting of."

Certain definitions used in the specification and claims are provided below. In order to provide a clear and consistent understanding of the specification and claims, including the scope to be given such terms, the following definitions are provided:

Agronomics," "agronomic traits," and "agronomic performance" refer to the traits (and underlying genetic elements) of a given plant variety that contribute to yield over the course of a growing season. Individual agronomic traits include emergence vigor, vegetative vigor, stress tolerance, disease resistance or tolerance, insect resistance or tolerance, herbicide resistance or tolerance, branching, flowering, seed set, seed size, seed density, standability, threshability, and the like.

"Allele" means any of one or more alternative forms of a genetic sequence. In a diploid cell or organism, the two alleles of a given sequence typically occupy corresponding loci on a pair of homologous chromosomes. With regard to a SNP marker, allele refers to the specific nucleotide base present at that SNP locus in that individual plant.

The term "amplifying" in the context of nucleic acid amplification is any process whereby additional copies of a selected nucleic acid (or a transcribed form thereof) are produced. Typical amplification methods include various polymerase based replication methods, including the polymerase chain reaction (PCR), ligase mediated methods, such as the ligase chain reaction (LCR), and RNA polymerase based amplification (e.g., by transcription) methods. An "amplicon" is an amplified nucleic acid, e.g., a nucleic acid that is produced by amplifying a template nucleic acid by any available amplification method (e.g., PCR, LCR, transcription, or the like).

An "ancestral line" is a parent line used as a source of genes, e.g., for the development of elite lines.

An "ancestral population" is a group of ancestors that have contributed the bulk of the genetic variation that was used to develop elite lines.

"Backcrossing" is a process in which a breeder crosses a progeny variety back to one of the parental genotypes one or more times.

"Breeding" means the genetic manipulation of living organisms.

The term "chromosome segment" designates a contiguous linear span of genomic DNA that resides in planta on a single chromosome.

The term "crossed" or "cross" means the fusion of gametes via pollination to produce progeny (e.g., cells, seeds or plants). The term encompasses both sexual crosses (the pollination of one plant by another) and selfing (self-pollination, e.g., when the pollen and ovule are from the same plant).

"Cultivar" and "variety" are used synonymously and mean a group of plants within a species (e.g., *Glycine max*) that share certain genetic traits that separate them from other possible varieties within that species. Soybean cultivars are inbred lines produced after several generations of self-pollinations. Individuals within a soybean cultivar are homogeneous, nearly genetically identical, with most loci in the homozygous state.

An "elite line" is an agronomically superior line that has resulted from many cycles of breeding and selection for superior agronomic performance. Numerous elite lines are available and known to those of skill in the art of soybean breeding.

An "elite population" is an assortment of elite individuals or lines that can be used to represent the state of the art in terms of agronomically superior genotypes of a given crop species, such as soybean.

An "equivalent position" in a polynucleotide and/or polypeptide sequence is a position that correlates to a position in the reference sequence when the sequences are aligned for a maximum correspondence. In some examples, the sequences are aligned across their whole length using a global alignment program. In other examples, a portion of the sequence or sequences may be aligned using a local alignment program or a global alignment program, for example a sequence may comprise exons and introns, conserved motifs or domains, or functional motifs or domains which may be aligned to the reference sequence(s) to identify equivalent positions. Equivalent positions in polynucleotides encoding a polypeptide can be determined using the encoded amino acid, and/or using a FrameAlign program to align the polynucleotide and polypeptide for maximal correspondence.

As used herein, the terms "exogenous" or "heterologous," as applied to polynucleotides or polypeptides, refer to molecules that have been artificially supplied to a biological system (e.g., a plant cell, a plant gene, a particular plant species or a plant chromosome under study) and are not native to that particular biological system. The terms indicate that the relevant material originated from a source other than the naturally occurring source, or refers to molecules having a non-natural configuration, genetic location or arrangement of parts. For example, exogenous polynucleotides include polynucleotides from another organism or from the same organism which have been modified by linkage to a distinct non-endogenous polynucleotide and/or inserted to a distinct non-endogenous locus. In contrast, for example, a "native" or "endogenous" gene is a gene that does not contain nucleic acid elements encoded by sources other than the chromosome or other genetic element on which it is normally found in nature. An endogenous gene, transcript or polypeptide is encoded by its natural chromosomal locus, and not artificially supplied to the cell. The term "introduced," when referring to a heterologous or exogenous nucleic acids, refers to the incorporation of a nucleic acid into a eukaryotic or prokaryotic cell using any type of suitable vector (e.g., naked linear DNA, plasmid, plastid, or virion), converted into an autonomous replicon, or transiently expressed (e.g., transfected mRNA). The term includes such nucleic acid introduction means as "transfection," "transformation," and "transduction." The term "host cell" means a cell that contains an exogenous nucleic acid, such as a vector, and supports the replication and/or expression of the nucleic acid. Host cells may be prokaryotic cells such as *E. coli*, or eukaryotic cells such as yeast, insect, amphibian or mammalian cells. In some examples, host cells are plant cells, including, but not limited to, dicot and monocot cells.

An "exotic soybean strain" or an "exotic soybean germplasm" is a strain or germplasm derived from a soybean not belonging to an available elite soybean line or strain of germplasm. In the context of a cross between two soybean plants or strains of germplasm, an exotic germplasm is not closely related by descent to the elite germplasm with which it is crossed. Most commonly, the exotic germplasm is not derived from any known elite line of soybean, but rather is selected to introduce novel genetic elements (typically novel alleles) into a breeding program.

A "genetic map" is a description of genetic linkage relationships among loci on one or more chromosomes (or linkage groups) within a given species, generally depicted in a diagrammatic or tabular form.

"Genotype" refers to the genetic constitution of a cell or organism.

"Germplasm" means the genetic material that comprises the physical foundation of the hereditary qualities of an organism. As used herein, germplasm includes seeds and living tissue from which new plants may be grown; or, another plant part, such as leaf, stem, pollen, or cells, that may be cultured into a whole plant. Germplasm resources provide sources of genetic traits used by plant breeders to improve commercial cultivars.

An individual is "homozygous" if the individual has only one type of allele at a given locus (e.g., a diploid individual has a copy of the same allele at a locus for each of two homologous chromosomes). An individual is "heterozygous" if more than one allele type is present at a given locus (e.g., a diploid individual with one copy each of two different alleles). The term "homogeneity" indicates that members of a group have the same genotype at one or more specific loci. In contrast, the term "heterogeneity" is used to indicate that individuals within the group differ in genotype at one or more specific loci.

"Haplotype" means a combination of sequence polymorphisms that are located closely together on the same chromosome and that can discriminate between different genotypes. The combination represented by the haplotype tends to be inherited together, and this combination may represent sequence differences or alleles within a region. The region may contain one gene, or more than one gene.

The term "homologous" refers to nucleic acid sequences that are derived from a common ancestral gene through natural or artificial processes (e.g., are members of the same gene family), and thus, typically share sequence similarity. Typically, homologous nucleic acids have sufficient sequence identity that one of the sequences or a subsequence thereof or its complement is able to selectively hybridize to the other under selective (e.g., stringent) hybridization conditions. The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing nucleic acid sequences typically have about at least 70% sequence identity, at least 80% sequence identity, or about 90%, 91%, 92%, 93%, 94%, 95%, 96%, 97%, 98%, 99%, 99.5%, 99.75%, or 100% sequence identity with each other. A nucleic acid that exhibits at least some degree of homology to a reference nucleic acid can be unique or identical to the reference nucleic acid or its complementary sequence.

The term "introgression" refers to the transmission of a desired allele of a genetic locus from one genetic background to another by sexual crossing, transgenic means, or any other means known in the art. For example, introgression of a desired allele at a specified locus can be transmitted to at least one progeny plant via a sexual cross between two parent plants, at least one of the parent plants having the desired allele within its genome. Alternatively, for example, transmission of an allele can occur by recombination between two donor genomes, e.g., in a fused protoplast, where at least one of the donor protoplasts has the desired allele in its genome. The desired allele can be, e.g., a transgene or a gene allele that imparts resistance to a plant pathogen.

The term "isolated" refers to material, such as polynucleotides or polypeptides, which are identified and separated from at least one contaminant with which it is ordinarily associated in its natural or original source. Furthermore, an isolated polynucleotide or polypeptide is typically present in a form or setting that is different from the form or setting that is normally found in nature. In some examples, the isolated molecule is substantially free from components that normally accompany or interact with it in its naturally occurring environment. In some embodiments, the isolated material optionally comprises material not found with the material in its natural environment, e.g., in a cell.

A "line" or "strain" is a group of individuals of identical parentage that are generally inbred to some degree and that are generally homozygous and homogeneous at most loci (isogenic or near isogenic). A "subline" refers to an inbred subset of descendents that are genetically distinct from other similarly inbred subsets descended from the same progenitor. Traditionally, a subline has been derived by inbreeding the seed from an individual soybean plant selected at the F3 to F5 generation until the residual segregating loci are "fixed" or homozygous across most or all loci. Commercial soybean varieties (or lines) are typically produced by aggregating ("bulking") the self-pollinated progeny of a single F3 to F5 plant from a controlled cross between two genetically different parents. While the variety typically appears uniform, the self-pollinating variety derived from the selected plant eventually (e.g., F8) becomes a mixture of homozygous plants that can vary in genotype at any locus that was heterozygous in the originally selected F3 to F5 plant. Marker-based sublines that differ from each other based on qualitative polymorphism at the DNA level at one or more specific marker loci are derived by genotyping a sample of seed derived from individual self-pollinated progeny derived from a selected F3-F5 plant. The seed sample can be genotyped directly as seed, or as plant tissue grown from such a seed sample. Optionally, seed sharing a common genotype at the specified locus (or loci) are bulked providing a subline that is genetically homogenous at identified loci important for a trait of interest (e.g., yield, tolerance, etc.).

"Linkage" refers to a phenomenon wherein alleles on the same chromosome tend to segregate together more often than expected by chance if their transmission was independent. Genetic recombination occurs with an assumed random frequency over the entire genome. Genetic maps are constructed by measuring the frequency of recombination between pairs of traits or markers. The closer the traits or markers lie to each other on the chromosome, the lower the frequency of recombination, and the greater the degree of linkage. Traits or markers are considered herein to be linked if they generally co-segregate. A $1/100$ probability of recombination per generation is defined as a map distance of 1.0 centiMorgan (1.0 cM). For example, in soybean, 1 cM correlates, on average, to about 400,000 base pairs (400 Kb).

The genetic elements or genes located on a single chromosome segment are physically linked. Advantageously, the two loci are located in close proximity such that recombination between homologous chromosome pairs does not occur between the two loci during meiosis with high frequency, e.g., such that linked loci co-segregate at least about 90% of the time, e.g., 91%, 92%, 93%, 94%, 95%, 96%, 97%, 98%, 99%, 99.5%, 99.75%, or more of the time. The genetic elements located within a chromosome segment are also genetically linked, typically within a genetic recombination distance of less than or equal to 50 centimorgans (cM), e.g., about 49, 40, 30, 20, 10, 5, 4, 3, 2, 1, 0.75, 0.5, or 0.25 cM or less. That is, two genetic elements within a single chromosome segment undergo recombination during meiosis with each other at a frequency of less than or equal to about 50%, e.g., about 49%, 40%, 30%, 20%, 10%, 5%, 4%, 3%, 2%, 1%, 0.75%, 0.5%, or 0.25% or less. Closely linked markers display a cross over frequency with a given marker of about 10% or less (the given marker is within about 10 cM of a closely linked marker). Put another way, closely linked loci co-segregate at least about 90% of the time.

When referring to the relationship between two genetic elements, such as a genetic element contributing to resistance and a proximal marker, "coupling" phase linkage indicates the state where the "favorable" allele at the resistance locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest (e.g., a QTL for resistance) is physically linked with an "unfavorable" allele at the proximal marker locus, and the two "favorable" alleles are not inherited together (i.e., the two loci are "out of phase" with each other).

"Linkage disequilibrium" refers to a phenomenon wherein alleles tend to remain together in linkage groups when segregating from parents to offspring, with a greater frequency than expected from their individual frequencies.

"Linkage group" refers to traits or markers that generally co-segregate. A linkage group generally corresponds to a chromosomal region containing genetic material that encodes the traits or markers.

"Locus" is a defined segment of DNA.

A "map location" is an assigned location on a genetic map relative to linked genetic markers where a specified marker can be found within a given species. Markers are frequently described as being "above" or "below" other markers on the same linkage group; a marker is "above" another marker if it appears earlier on the linkage group, whereas a marker is "below" another marker if it appears later on the linkage group.

"Mapping" is the process of defining the linkage relationships of loci through the use of genetic markers, populations segregating for the markers, and standard genetic principles of recombination frequency.

"Marker" or "molecular marker" is a term used to denote a nucleic acid or amino acid sequence that is sufficiently unique to characterize a specific locus on the genome. Examples include Restriction Fragment Length Polymorphisms (RFLPs), Single Sequence Repeats (SSRs), Target Region Amplification Polymorphisms (TRAPs), Isozyme Electrophoresis, Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Single Nucleotide Polymorphisms (SNPs). Additionally, other types of molecular markers are known to the art, and phenotypic traits may also be used as markers. All markers are used to define a specific locus on the soybean genome. Large numbers of these markers have been mapped. Each marker is therefore an indicator of a specific segment of DNA, having a unique nucleotide sequence. The map positions provide a measure of the relative positions of particular markers with respect to one another. When a trait is stated to be linked to a given marker it will be understood that the actual DNA segment whose sequence affects the trait generally co-segregates with the marker. More precise and definite localization of a trait can be obtained if markers are identified on both sides of the trait. By measuring the appearance of the marker(s) in progeny of crosses, the existence of the trait can be detected by relatively simple molecular tests without actually evaluating the appearance of the trait itself, which can be difficult and time-consuming because the actual evaluation of the trait requires growing plants to a stage and/or under specific conditions where the trait can be expressed. Molecular markers have been widely used to determine genetic composition in soybeans. Shoemaker and Olsen, ((1993) Molecular Linkage Map of Soybean (*Glycine max* L. Men.). p. 6.131-6.138. In S. J. O'Brien (ed.) Genetic Maps: Locus Maps of Complex Genomes. Cold Spring Harbor Laboratory Press. Cold Spring Harbor, N.Y.), developed a molecular genetic linkage map that consisted of 25 linkage groups with about 365 RFLP, 11 RAPD, three classical markers, and four isozyme loci. See also Shoemaker R. C. (1994) RFLP Map of Soybean. pp. 299-309 in R. L. Phillips and I. K. Vasil (ed.) DNA-based markers in plants. Kluwer Academic Press Dordrecht, the Netherlands.

"Marker assisted selection" refers to the process of selecting a desired trait or desired traits in a plant or plants by detecting one or more molecular markers from the plant, where the molecular marker is linked to the desired trait.

The term "plant" includes reference to an immature or mature whole plant, including a plant from which seed or grain or anthers have been removed. Seed or embryo that will produce the plant is also considered to be the plant.

As used herein, the term "plant cell" includes, without limitation, cells within or derived from, for example and without limitation, plant seeds, plant tissue suspension cultures, plant tissue, plant tissue explants, plant embryos, meristematic tissue, callus tissue, leaves, roots, shoots, gametophytes, sporophytes, pollen and microspores.

"Plant parts" means any portion or piece of a plant, including leaves, stems, buds, roots, root tips, anthers, seed, grain, embryo, pollen, ovules, flowers, cotyledons, hypocotyls, pods, flowers, shoots, stalks, tissues, tissue cultures, cells and the like.

"Polymorphism" means a change or difference between two related nucleic acids. A "nucleotide polymorphism" refers to a nucleic acid comprising at least one nucleotide difference when compared to a related sequence when the two nucleic acids are aligned for maximal correspondence. A "genetic nucleotide polymorphism" refers to a nucleic acid comprising at least one nucleotide difference when compared to a related sequence when the two nucleic acids are aligned for maximal correspondence, where the two nucleic acids are genetically related, i.e., homologous, for example, where the nucleic acids are isolated from different strains of a soybean plant, or from different alleles of a single strain, or the like.

"Polynucleotide," "polynucleotide sequence," "nucleic acid sequence," "nucleic acid fragment," and "oligonucleotide" are used interchangeably herein. These terms encompass nucleotide sequences and the like. A polynucleotide may be a polymer of RNA or DNA that is single- or double-stranded, that optionally contains synthetic, non-natural, or altered nucleotide bases. A polynucleotide in the form of a polymer of DNA may be comprised of one or more strands of cDNA, genomic DNA, synthetic DNA, or mixtures thereof.

"Positional cloning" is a cloning procedure in which a target nucleic acid is identified and isolated by its genomic proximity to marker nucleic acid. For example, a genomic nucleic acid clone can include part or all of two more chromosomal regions that are proximal to one another. If a marker can be used to identify the genomic nucleic acid clone from a genomic library, standard methods such as sub-cloning or sequencing can be used to identify and or isolate subsequences of the clone that are located near the marker.

"Primer" refers to an oligonucleotide (synthetic or occurring naturally), which is capable of acting as a point of initiation of nucleic acid synthesis or replication along a complementary strand when placed under conditions in which synthesis of a complementary strand is catalyzed by a polymerase. Typically, primers are oligonucleotides from 10 to 30 nucleic acids in length, but longer or shorter sequences can be employed. Primers may be provided in double-stranded form, though the single-stranded form is preferred. A primer can further contain a detectable label, for example a 5' end label.

"Probe" refers to an oligonucleotide (synthetic or occurring naturally) that is complementary (though not necessarily fully complementary) to a polynucleotide of interest and forms a duplexed structure by hybridization with at least one strand of the polynucleotide of interest. Typically, probes are oligonucleotides from 10 to 50 nucleic acids in length, but longer or shorter sequences can be employed. A probe can further contain a detectable label. The terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, semiconductor nanocrystals, ligands (e.g., biotin, avidin, streptavidin, or haptens), and the like. A detectable label can also include a combination of a reporter and a quencher, such as are employed in FRET probes or TaqMan™ probes. The term "reporter" refers to a substance or a portion thereof which is capable of exhibiting a detectable signal, which signal can be suppressed by a quencher. The detectable signal of the reporter is, e.g., fluorescence in the detectable range. The term "quencher" refers to a substance or portion thereof which is capable of suppressing, reducing, inhibiting, etc., the detectable signal produced by the reporter. As used herein, the terms "quenching" and "fluorescence energy transfer" refer to the process whereby, when a reporter and a quencher are in close proximity, and the reporter is excited by an energy source, a substantial portion of the energy of the excited state nonradiatively transfers to the quencher where it either dissipates nonradiatively or is emitted at a different emission wavelength than that of the reporter.

"RAPD marker" means random amplified polymorphic DNA marker. Chance pairs of sites complementary to single octa- or decanucleotides may exist in the correct orientation and close enough to one another for PCR amplification. With some randomly chosen decanucleotides no sequences are amplified. With others, the same length products are generated from DNAs of different individuals. With still others, patterns of bands are not the same for every individual in a population. The variable bands are commonly called random amplified polymorphic DNA (RAPD) bands.

The term "recombinant" indicates that the material (e.g., a recombinant nucleic acid, gene, polynucleotide or polypeptide) has been altered by human intervention. Generally, the arrangement of parts of a recombinant molecule is not a native configuration, or the primary sequence of the recombinant polynucleotide or polypeptide has in some way been manipulated. The alteration to yield the recombinant material can be performed on the material within or removed from its natural environment or state. For example, a naturally occurring nucleic acid becomes a recombinant nucleic acid if it is altered, or if it is transcribed from DNA which has been altered, by means of human intervention performed within the cell from which it originates. A gene sequence open reading frame is recombinant if that nucleotide sequence has been removed from it natural text and cloned into any type of artificial nucleic acid vector. Protocols and reagents to produce recombinant molecules, especially recombinant nucleic acids, are common and routine in the art (see, e.g., Maniatis et al. (eds.), Molecular Cloning: A Laboratory Manual, Cold Spring Harbor Laboratory Press, NY, [1982]; Sambrook et al. (eds.), Molecular Cloning: A Laboratory Manual, Second Edition, Volumes 1-3, Cold Spring Harbor Laboratory Press, NY, [1989]; and Ausubel et al. (eds.), Current Protocols in Molecular Biology, Vol. 1-4, John Wiley & Sons, Inc., New York [1994]). The term recombinant can also refer to an organism that harbors a recombinant material, e.g., a plant that comprises a recombinant nucleic acid is considered a recombinant plant. In some embodiments, a recombinant organism is a transgenic organism.

"Recombination frequency" is the frequency of a crossing over event (recombination) between two genetic loci. Recombination frequency can be observed by following the segregation of markers and/or traits during meiosis. A marker locus is "associated with" another marker locus or some other locus (for example, a tolerance locus), when the relevant loci are part of the same linkage group and are in linkage disequilibrium. This occurs when the marker locus and a linked locus are found together in progeny plants more frequently than if the two loci segregated randomly. Similarly, a marker locus can also be associated with a trait, e.g., a marker locus can be "associated with tolerance or improved tolerance," when the marker locus is in linkage disequilibrium with the trait.

"RFLP" means restriction fragment length polymorphism. Any sequence change in DNA, including a single base substitution, insertion, deletion or inversion, can result in loss or gain of a restriction endonuclease recognition site. The size and number of fragments generated by one such enzyme is therefore altered. A probe that hybridizes specifically to DNA in the region of such an alteration can be used to rapidly and specifically identify a region of DNA that displays allelic variation between two plant varieties. Isozyme Electrophoresis and RFLPs have been widely used to determine genetic composition "Self crossing" or "self pollination" or "selfing" a process through which a breeder crosses progeny with itself; for example, a second generation hybrid F2 with itself to yield progeny designated F2:3.

"SNP" or "single nucleotide polymorphism" means a sequence variation that occurs when a single nucleotide (A, T, C, or G) in the genome sequence is altered or variable. "SNP markers" exist when SNPs are mapped to sites on the soybean genome. Many techniques for detecting SNPs are known in the art, including allele specific hybridization, primer extension, direct sequencing, and real-time PCR, such as the TaqMan™ assay.

"SSR" means short sequence repeats. "SSR markers" are genetic markers based on polymorphisms in repeated nucleotide sequences, such as microsatellites. A marker system based on SSRs can be highly informative in linkage analysis relative to other marker systems in that multiple alleles may be present. The PCR detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology.

"Tolerance" and "improved tolerance" are used interchangeably herein and refer to plants in which higher doses of an herbicide are required to produce effects similar to those seen in non-tolerant plants. Tolerant plants typically exhibit fewer necrotic, lytic, chlorotic, or other lesions when subjected to the herbicide at concentrations and rates typically employed by the agricultural community. A "tolerant plant" or "tolerant plant variety" need not possess absolute or complete tolerance such that no detrimental effect to the plant or plant variety is observed when the given herbicide is applied. Instead, a "tolerant plant," "tolerant plant variety," or a plant or plant variety with "improved tolerance" will simply be less affected by the given herbicide than a comparable susceptible plant or variety.

"Transgenic plant" refers to a plant that comprises within its cells an exogenous polynucleotide, e.g., a polynucleotide from another organism (including a polynucleotide from another soybean plant). Generally, the exogenous polynucleotide is stably integrated within a genome such that the polynucleotide is passed on to successive generations. The exogenous polynucleotide may be integrated into the genome alone or as part of a recombinant expression cassette. "Transgenic" is used herein to refer to any cell, cell line, callus, tissue, plant part, or plant, the genotype of which has been altered by the presence of exogenous nucleic acid including those transgenic organisms or cells initially so altered, as well as those created by crosses or asexual propagation from the initial transgenic organism or cell. The term "transgenic" as used herein does not encompass the alteration of the genome (chromosomal or extra-chromosomal) by conventional plant breeding methods (e.g., crosses) or by naturally occurring events such as random cross-fertilization, non-recombinant viral infection, non-recombinant bacterial transformation, non-recombinant transposition, or spontaneous mutation.

"TRAP marker" means target region amplification polymorphism marker. The TRAP technique employs one fixed primer of known sequence in combination with a random primer to amplify genomic fragments. The differences in fragments between alleles can be detected by gel electrophoresis.

The term "vector" is used in reference to polynucleotide or other molecules that transfer nucleic acid segment(s) into a cell. A vector optionally comprises parts which mediate vector maintenance and enable its intended use (e.g., sequences necessary for replication, genes imparting drug or antibiotic resistance, a multiple cloning site, operably linked promoter/enhancer elements which enable the expression of a cloned gene, etc.). Vectors are often derived from plasmids, bacteriophages, or plant or animal viruses.

The term "yield" refers to the productivity per unit area of a particular plant product of commercial value. For example, yield of soybean is commonly measured in bushels of seed per acre or metric tons of seed per hectare per season. Yield is affected by both genetic and environmental factors. Yield is the final culmination of all agronomic traits.

Mesotrione and Isoxazole

Mesotrione and isoxazole are two herbicide classes from different chemical families, but both can act as hydroxyphenyl pyruvate dioxygenase (HPPD) inhibitors. Isoxazole is used as a pre-plant herbicide while mesotrione is used as either a pre-plant or post-emergent herbicide. Isoxazole is member of the isoxazole chemical family. Following either foliar or root uptake, isoxazole is rapidly converted to a diketonitrile derivative (2-cyclopropyl-3-(2-mesyl-4-trifluoromethylphenyl)-3-oxopropanenitrile) by opening of the isoxazole ring. This diketonitrile undergoes degradation to a benzoic acid derivative (2-mesyl-4-trifluoromethyl benzoic acid) in treated plants and the extent of this degradation is correlated to the degree of susceptibility, being most rapid in tolerant plants and slowest in susceptible plants.

Mesotrione belongs to the triketone family of herbicides, which are chemically derived from a natural phytotoxin produced by the bottlebrush plant *Callistemon citrinus*. Mesotrione works by inhibiting HPPD (p-hydroxyphenylpyruvate dioxygenase), an essential enzyme in the biosynthesis of carotenoids. Carotenoids protect chlorophyll from excess light energy.

Molecular Markers and Genetic Linkage

Table A below provides an integrated genetic map of soybean markers on linkage group L (chromosome 19), including the marker type (SSR or ASH/SNP). The genetic map positions of the markers are indicated in centiMorgans (cM), typically with position zero being the first (most distal) marker on the chromosome. The map includes relative positions for some markers for which higher resolution genetic mapping data was not available; no position in cM is provided for such markers. Table B lists genetic markers that are linked to the mesotrione and isoxazole herbicide tolerance and sensitivity markers identified on linkage group L. These markers are from the soybean public composite map of Jun. 18, 2008 for linkage group L.

TABLE A

| Marker | Linkage Group | Position | Type |
|---|---|---|---|
| SATT495 | L | 0.00 | SSR |
| SATT723 | L | 0.44 | SSR |
| SAT_408 | L | 1.00 | SSR |
| S08102-1-Q1 | L |  | SNP |
| S08103-1-Q1 |  |  |  |
| S08104-1-Q1 |  |  |  |
| S08106-1-Q1 |  |  |  |
| S08107-1-Q1 |  |  |  |
| S08107-1-Q1 |  |  |  |
| S08109-1-Q1 |  |  |  |
| S08110-1-Q1 |  |  |  |
| S08111-1-Q1 |  |  |  |
| S08115-2-Q1 |  |  |  |
| S08117-1-Q1 |  |  |  |
| S08119-1-Q1 |  |  |  |
| S08116-1-Q1 |  |  |  |
| S08112-1-Q1 |  |  |  |
| S08108-1-Q1 |  |  |  |
| S08101-4-Q1 |  |  |  |
| S08101-1-Q1 |  |  |  |
| S08101-2-Q1 |  |  |  |
| S08101-3-Q1 |  |  |  |
| S08118-1-Q1 |  |  |  |
| S08114-1-Q1 |  |  |  |
| S08113-1-Q1 |  |  |  |
| S03859-1-A |  |  |  |
| Sat_301 | L | 10.31 | SSR |
| SATT446 | L | 11.13 | SSR |
| P10649C-3 | L | 12.5 | ASH |
| SATT232 | L | 12.55 | SSR |
| S08105-1-Q1 | L |  | SNP |
| SATT182 | L | 13.90 | SSR |
| S08010-1-Q1 | L |  | SNP |
| S08010-2-Q1 |  |  |  |
| SATT238 | L | 19.41 | SSR |
| Sat_071 | L | 20.04 | SSR |
| SATT388 | L | 21.61 | SSR |
| SATT497 | L | 26.06 | SSR |
| SATT313 | L | 27.35 | SSR |
| SATT143 | L | 28.16 | SSR |
| Sat_397 | L | 28.26 | SSR |
| SATT418 | L | 28.57 | SSR |
| Sat_134 | L | 28.66 | SSR |
| SATT652 | L | 28.67 | SSR |
| SATT711 | L | 28.67 | SSR |
| Sat_187 | L | 28.68 | SSR |
| Sat_195 | L | 28.68 | SSR |
| Sat_388 | L | 28.71 | SSR |
| SATT694 | L | 28.71 | SSR |
| SATT398 | L | 28.90 | SSR |
| Sat_191 | L | 29.19 | SSR |
| Sat_405 | L | 29.40 | SSR |
| Sat_320 | L | 29.74 | SSR |
| SATT523 | L | 30.18 | SSR |
| SATT278 | L | 30.34 | SSR |
| SATT613 | L | 32.64 | SSR |

TABLE B

| | | Linked Markers | | | |
|---|---|---|---|---|---|
| Satt495 | Satt723 | Sat_408 | A169_1 | EV2_1 | Sle3_4s |
| BLT010_2 | BLT007_1 | Satt232 | Sat_301 | Satt446 | Satt182 |
| R176_1 | JUBC090 | Satt238 | Sat_071 | BLT039_1 | Bng071_1 |
| Satt388 | A264_1 | RGA_7 | RGA7 | Satt523 | Sat_134 |
| LbA | i8_2 | A450_2 | A106_1 | Sat_405 | Satt143 |
| B124_2 | A459_1 | Satt398 | Satt694 | Sat_195 | Sat_388 |
| Satt652 | Satt711 | Sat_187 | Satt418 | Satt278 | Sat_397 |
| Sat_191 | Sat_320 | O109_1 | A204_2 | Satt497 | G214_17 |
| Satt313 | B164_1 | G214_16 | Satt613 | A023_1 | Satt284 |
| AW508247 | Satt462 | L050_7 | E014_1 | A071_5 | B046_1 |
| L1 | B162_2 | S00224-1 | S01659-1 | | |

Table C provides examples of primer and probe nucleic acid sequences that are useful for detecting SNP markers associated with tolerance, improved tolerance, or susceptibility/sensitivity to mesotrione and/or isoxazole herbicides.

TABLE C

| Marker Name | PCR Primers | Allele Probes |
|---|---|---|
| P10649C-3 LG-L | Primer Seq 1 (SEQ ID NO. 1): GAGGGCTATGTTTTCTTCT CCAGATGTGAG<br>Primer Seq 2 (SEQ ID NO. 2): AAGGTCGGCTTGGTGGTTA AAGGCAG | Allele 1 Probe (SEQ ID NO. 3): TCATcTgTGATAA<br>Allele 2 Probe (SEQ ID NO. 4): TCATgTgTGATAA<br>Allele 3 Probe (SEQ ID NO. 5): TCATcTcTGATAA |
| S00224-1 LG-L | Primer Seq 1 (F) (SEQ ID NO. 6): CTGGACCTACCCGGGATG AAAA<br>Primer Seq 2 (R) (SEQ ID NO. 7): TCTTCCTCTCCCTTCCTCTC GC | Allele 1 Probe (PF1) (SEQ ID NO. 8): CGCGAcTCTCCTC<br>Allele 2 Probe (PV1) (SEQ ID NO. 9): CGCGAgTCTCCTC |
| P5467-1 LG-N | Primer Seq 1 (SEQ ID NO. 10): TCCCAGGTTAGATTTTCTG AACGAAGA<br>Primer Seq 2 (SEQ ID NO. 11): CATCAGCACAAAAGGGCA TCCTCA | Allele 1 Probe (SEQ ID NO. 12): CACTCCTTAAGgTAAT<br>Allele 2 Probe (SEQ ID NO. 13): CACTCCTTAAGaTAAT |
| S08101-1 Q1 LG-L | Primer Seq 1 (F) (SEQ ID NO. 14): gttatcgtcaccaccaccaa<br>Primer Seq 2 (R) (SEQ ID NO. 15): cacaacacgagtagccgtagg | Allele 1 Probe (PF1) (SEQ ID NO. 16) aacggAtcatcacaac<br>Allele 2 Probe (PV1) (SEQ ID NO. 17) aacggCtcatcacaa |
| S08101-2-Q1 LG-L | Primer Seq 1(F) (SEQ ID NO. 18): cgacaatggcctttacacct<br>Primer Seq 2 (R) (SEQ ID NO. 19): tcgatatggacgaaggagga | Allele 1 Probe (PF1) (SEQ ID NO. 20) acaccAttttcatcc<br>Allele 2 Probe (PV1) (SEQ ID NO. 21) acaccCttttcatcc |
| S08101-3-Q1 LG-L | Primer Seq 1 (F) (SEQ ID NO. 22): GCAATCACATTTGCATTCC TTA<br>Primer Seq 2 (R) (SEQ ID NO. 23): TCTGAACGAGTTGTGCAAG AA | Allele 1 Probe (PF1) (SEQ ID NO. 24) actgctGctttgtcta<br>Allele 2 Probe (PV1) (SEQ ID NO. 25) ctactgctActttgtc |
| S08101-4-Q1 LG-L | Primer Seq 1 (F) (SEQ ID NO. 26): acctcgtattggtggtggtg<br>Primer Seq 2 (R) (SEQ ID NO. 27): gaatgttcagtgcgagcaac | Allele 1 Probe (PF1) (SEQ ID NO. 28) acttccctcGtttcg<br>Allele 2 Probe (PV1) (SEQ ID NO. 29) cttccctcAtttcg |
| S08102-1-Q1 LG-L | Primer Seq 1 (F) (SEQ ID NO. 30): caaaaggaaagaagaaccgtgt<br>Primer Seq 2 (R) (SEQ ID NO. 31): tccaacctatgtgttggtgtg | Allele 1 Probe (PF1) (SEQ ID NO. 32) atgattgaagcagGaaa<br>Allele 2 Probe (PV1) (SEQ ID NO. 33) tcatgattgaagcagCaa |

TABLE C-continued

| Marker Name | PCR Primers | Allele Probes |
|---|---|---|
| S08103-1-Q1 LG-L | Primer Seq 1 (F) (SEQ ID NO. 34): ggagacttgacttaaagagaaagaaaa Primer Seq 2 (R) (SEQ ID NO. 35): cggaaagaaaaacaatagattgaatg | Allele 1 Probe (PF1) (SEQ ID NO. 36) cttgttctagactgatCat Allele 2 Probe (PV1) (SEQ ID NO. 37) ctagactgatAattca |
| S08104-1-Q1 LG-L | Primer Seq 1 (F) (SEQ ID NO. 38): tcattcaagactacatgaaagacaaa Primer Seq 2 (R) (SEQ ID NO. 39): caagggagagcaatccttga | Allele 1 Probe (PF1) (SEQ ID NO. 40) atagtctcCcaaacac Allele 2 Probe (PV1) (SEQ ID NO. 41) atagtctcTcaaacacc |
| S08105-1-Q1 LG-L | Primer Seq 1 (F) (SEQ ID NO. 42): gaaactttccattttgcccttc Primer Seq 2 (R) (SEQ ID NO. 43): agaacgcaggggagaagc | Allele 1 Probe (PF1) (SEQ ID NO. 44) cttcttCcactcttac Allele 2 Probe (PV1) (SEQ ID NO. 45) ccttcttAcactcttac |
| S08106-1-Q1 LG-L | Primer Seq 1 (F) (SEQ ID NO. 46): tgatatgacactctactaagatgtgttg Primer Seq 2 (R) (SEQ ID NO. 47): tgattcatccgcaaacttga | Allele 1 Probe (PF1) (SEQ ID NO. 48) cactctcctaTattgtc Allele 2 Probe (PV1) (SEQ ID NO. 49) ctctcctaCattgtca |
| S08107-1-Q1 LG-L | Primer Seq 1 (F) (SEQ ID NO. 50): agatccttgttccaaattccaa Primer Seq 2 (R) (SEQ ID NO. 51): ccttggcttaatgggtgtgt | Allele 1 Probe (PF1) (SEQ ID NO. 52) ccaacacaatcTaact Allele 2 Probe (PV1) (SEQ ID NO. 53) ccaacacaatcGaa |
| S08108-1-Q1 LG-L | Primer Seq 1 (F) (SEQ ID NO. 54): atggaggcaagcttgtgttt Primer Seq 2 (R) (SEQ ID NO. 55): catgctaccagcatctgcaa | Allele 1 Probe (PF1) (SEQ ID NO. 56) cttcataaaCgccaaag Allele 2 Probe (PV1) (SEQ ID NO. 57) cataaaTgccaaagca |
| S08109-1-Q1 LG-L | Primer Seq 1 (F) (SEQ ID NO. 58): aatgagcaagggagaggaca Primer Seq 2 (R) (SEQ ID NO. 59): tcgccgctgctatttaattt | Allele 1 Probe (PF1) (SEQ ID NO. 60) aagcacTactttcaattg Allele 2 Probe (PV1) (SEQ ID NO. 61) aagcacCactttca |
| S08110-1-Q1 LG-L | Primer Seq 1 (F) (SEQ ID NO. 62): agatgccttgctcagtggac Primer Seq 2 (R) (SEQ ID NO. 63): atgatgaatgtgttgagccaat | Allele 1 Probe (PF1) (SEQ ID NO. 64) ccccaTcaccatac Allele 2 Probe (PV1) (SEQ ID NO. 65) accccaCcaccata |
| S08111-1-Q1 LG-L | Primer Seq 1 (F) (SEQ ID NO. 66): agaaaccttccaaagctcttgg Primer Seq 2 (R) (SEQ ID NO. 67): tagggaggcacttgacaacc | Allele 1 Probe (PF1) (SEQ ID NO. 68) caacatcCgagtcca Allele 2 Probe (PV1) (SEQ ID NO. 69) caacatcAgagtcca |
| S08112-1-Q1 LG-L | Primer Seq 1 (F) (SEQ ID NO. 70): ttttgaccccagagagttg Primer Seq 2 (R) (SEQ ID NO. 71): ttgcaagcctaaaggatggt | Allele 1 Probe (PF1) (SEQ ID NO. 72) ctatctcTacacgatgtgt Allele 2 Probe (PV1) (SEQ ID NO. 73) ctatctcCacacgatg |
| S08115-2-Q1 LG-L | Primer Seq 1 (F) (SEQ ID NO. 74): tcccacttgatcttgcagaa Primer Seq 2 (R) (SEQ ID NO. 75): tacggtgggtggattattcg | Allele 1 Probe (PF1) (SEQ ID NO. 76) cctccaatGgcatac Allele 2 Probe (PV1) (SEQ ID NO. 77) cctccaatAgcatacat |
| S08116-1-Q1 LG-L | Primer Seq 1 (F) (SEQ ID NO. 78): agaaaagcagcagaaagaggac Primer Seq 2 (R) (SEQ ID NO. 79): cttcatgaatcccaacatcaga | Allele 1 Probe (PF1) (SEQ ID NO. 80) ctctaattCcacatctg Allele 2 Probe (PV1) (SEQ ID NO. 81) cctctaattTcacatctg |
| S08117-1-Q1 LG-L | Primer Seq 1 (F) (SEQ ID NO. 82): tcaaaccattttgtttcccagt Primer Seq 2 (R) (SEQ ID NO. 83): tgctagcctttgatacccaac | Allele 1 Probe (PF1) (SEQ ID NO. 84) ttgcattgtattCtct Allele 2 Probe (PV1) (SEQ ID NO. 85) ttgcattgtattTtc |
| S08118-1-Q1 LG-L | Primer Seq 1 (F) (SEQ ID NO. 86): gtctcaggcagtgaatctgct Primer Seq 2 (R) (SEQ ID NO. 87): cagccttaccatcaacatcg | Allele 1 Probe (PF1) (SEQ ID NO. 88) ttccgTgaagatc Allele 2 Probe (PV1) (SEQ ID NO. 89) atgcttccgCgaaga |

TABLE C-continued

| Marker Name | PCR Primers | Allele Probes |
|---|---|---|
| S08119-1-Q1 LG-L | Primer Seq 1 (F) (SEQ ID NO. 90): ggtagcagttactttgtgatgtaagc<br>Primer Seq 2 (R) (SEQ ID NO. 91): catgcaataaaatccaaaacca | Allele 1 Probe (PF1) (SEQ ID NO. 92) tactgaTcacaggttat<br>Allele 2 Probe (PV1) (SEQ ID NO. 93) tactgaCcacaggttat |
| S04867-1-A LG-L | Primer Seq 1 (F) (SEQ ID NO. 94.): ttgctttggaaaggactcca<br>Primer Seq 2 (R) (SEQ ID NO. 95): cctcatcaactcctgctgct | Allele 1 Probe (PF1) (SEQ ID NO. 96) ctcggtgctgtTtt<br>Allele 2 Probe (PV1) (SEQ ID NO. 97) ctcggtgctgtCtt |
| S03859-1-A LG-L | Primer Seq 1 (F) (SEQ ID NO. 98): gaaaccaattttgatgtgaagga<br>Primer Seq 2 (R) (SEQ ID NO. 99): aagtgagaggggtgcaaaga | Allele 1 Probe (PF1) (SEQ ID NO. 100) cagccctAtctcac<br>Allele 2 Probe (PV1) (SEQ ID NO. 101) agccctGtctcact |
| S08010-1-Q1 LG-L | Primer Seq 1 (F) (SEQ ID NO. 102): gcaaatgagaaggctgaagct<br>Primer Seq 2 (R) (SEQ ID NO. 103): gctgtccctcagtccatcc | Allele 1 Probe (PF1) (SEQ ID NO. 104) cggtatcgctcgTca<br>Allele 2 Probe (PV1) (SEQ ID NO. 105) tatcgctcgCcaacg |
| S08010-2-Q1 LG-L | Primer Seq 1 (F) (SEQ ID NO. 106): atccacttgcaagataggacact<br>Primer Seq 2 (R) (SEQ ID NO. 107): gtgtaagtactgatgtgcagttttga | Allele 1 Probe (PF1) (SEQ ID NO. 108) cttgacattaagact:atcc<br>Allele 2 Probe (PV1) (SEQ ID NO. 109) agactAatccttaaacaag |
| S08114-1-Q1 LG-L | Primer Seq 1 (F) (SEQ ID NO: 110): tcaacaggttatgaatatacaggtcaa<br>Primer Seq 2(R) (SEQ ID NO: 111): catcaccaattgtttggagttc | Allele 1 Probe (PF1) (SEQ ID NO: 112) ctattactcTccgttattt<br>Allele 2 Probe (PV1) (SEQ ID NO: 113) ctattactcCccgttatt |
| S08113-1-Q1 LG-L | Primer Seq 1 (F) (SEQ ID NO: 114): ttgttgaatgggggcact<br>Primer Seq 2 (R) (SEQ ID NO: 115): ctcgagcaaatctcgatggt | Allele 1 Probe (PF1) (SEQ ID NO: 116) ttgaatgCttactctct<br>Allele 2 Probe (PV1) (SEQ ID NO: 117) ttgaatgTttactctcttt |
| S08007-1-Q1 LG-L | Primer Seq 1 (F) (SEQ ID NO: 118): ctgtggaggaggagcttgag<br>Primer Seq 2(R) (SEQ ID NO: 119): acaagtcacaaccgtcaatgat | Allele 1 Probe (PF1) (SEQ ID NO: 120) agctttgttttctctTtt<br>Allele 2 Probe (PV1) (SEQ ID NO: 121) agctttgttttctctCtt |

In traditional linkage analysis, no direct knowledge of the physical relationship of genes on a chromosome is required. Mendel's first law is that factors of pairs of characteristics are segregated, meaning that alleles of a diploid trait separate into two gametes and then into different offspring. Classical linkage analysis can be thought of as a statistical description of the relative frequencies of cosegregation of different traits. Linkage analysis, as described previously, is the well-characterized descriptive framework of how traits are grouped together based upon the frequency with which they segregate together. Because chromosomal distance is approximately proportional to the frequency of crossing over events between traits, there is an approximate physical distance that correlates with recombination frequency.

Marker loci are traits, and can be assessed according to standard linkage analysis by tracking the marker loci during segregation. Thus, one cM is equal to a 1% chance that a marker locus will be separated from another locus (which can be any other trait, e.g., another marker locus, or another trait locus that encodes a QTL), due to crossing over in a single generation. Any detectible polymorphic trait can be used as a marker so long as it is inherited differentially and exhibits linkage disequilibrium with a phenotypic trait of interest. A number of soybean markers have been mapped and linkage groups created, as described in Cregan, P. B. et al., "An Integrated Genetic Linkage Map of the Soybean Genome" (1999) Crop Science 39:1464-90, and more recently in Choi et al., "A Soybean Transcript Map: Gene Distribution, Haplotype and Single-Nucleotide Polymorphism Analysis" (2007) Genetics 176:685-96. Many soybean markers are publicly available at the USDA affiliated soybase website.

Most plant traits of agronomic importance are polygenic, otherwise known as quantitative traits. A quantitative trait is controlled by two or more genes located at various locations, or loci, in the plant's genome. The multiple genes have a cumulative effect which contributes to the continuous range of phenotypes observed in many plant traits. These genes are referred to as quantitative trait loci (QTL). Recombination frequency measures the extent to which a molecular marker is linked with a QTL. Lower recombination frequencies, typically measured in centiMorgans (cM), indicate greater linkage between the QTL and the molecular marker. The extent to which two features are linked is often referred to as the genetic distance. The genetic distance is also typically related to the physical distance between the marker and the QTL; however, certain biological phenomenon (including recombinational "hot spots") can affect the relationship between physical distance and genetic distance. Generally, the usefulness of a molecular marker is determined by the genetic and physical distance between the marker and the selectable trait of interest.

The method for determining the presence or absence of a QTL associated with tolerance or sensitivity to mesotrione and/or isoxazole herbicides in soybean germplasm, comprises analyzing genomic DNA from a soybean germplasm for the presence of at least one molecular marker, wherein at least one molecular marker is linked to the QTL, and wherein the QTL maps to soybean major linkage group L and is associated with tolerance or sensitivity to mesotrione and/or isoxazole herbicides. The term "is associated with" in this context means that the QTL associated with tolerance or sensitivity to mesotrione and/or isoxazole herbicides has been found to be present in soybean plants showing tolerance or sensitivity to mesotrione and/or isoxazole herbicides as described herein.

Any marker that is linked to a trait of interest (e.g., in the present case, a tolerance or improved tolerance trait) can be used as a marker for that trait. Thus, in addition to the markers described herein, markers linked to the markers itemized herein can also be used to predict the tolerance, improved tolerance, or susceptibility/sensitivity trait. Such linked markers are particularly useful when they are sufficiently proximal to a given marker so that they display a low recombination frequency with the given marker. Markers linked and/or closely linked to the given markers are provided, for example, in Tables A and B above. These include, for example, SATT495, SATT723, Sat_408, A169_1, EV2_1, Sle3_4s, BLT010_2, BLT007_1, SATT232, S04867-1-A, S08102-1-Q1, S08103-1-Q1, S08104-1-Q1, S08106-1-Q1, S08107-1-Q1, S08109-1-Q1, S08110-1-Q1, S08111-1-Q1, S08115-2-Q1, S08117-1-Q1, S08119-1-Q1, S08116-1-Q1, S08112-1-Q1, S08108-1-Q1, S08101-4-Q1, S08101-1-Q1, S08101-2-Q1, S08101-3-Q1, S08118-1-Q1, S08114-1-Q1, S08113-1-Q1, S03859-1-A, Sat_301, SATT446, P10649C-3, SATT232, S08105-1-Q1, SATT182, S08010-1-Q1, S08010-2-Q1, R176_1, JUBC090, SATT238, Sat_071, BLT039_1, Bng071_1, SATT388, A264_1, RGA_7, RGA7, SATT523, Sat_134, S00224-1, S01659-1, LbA, i8_2, A450_2, A106_1, Sat_405, SATT143, B124_2, A459_1, SATT398, SATT694, Sat_195, Sat_388, SATT652, SATT711, Sat_187, SATT418, SATT278, Sat_397, Sat_191, Sat_320, O109_1, A204_2, SATT497, G214_17, SATT313, B164_1, G214_16, SATT613, A023_1, SATT284, AW508247, SATT462, L050_7, E014_1, A071_5, B046_1, L1, and B162_2.

Marker loci are especially useful when they are closely linked to target loci (e.g., QTL for tolerance, or, alternatively, simply other marker loci, such as those identified herein, that are linked to such QTL) for which they are being used as markers. A marker more closely linked to a target locus is a better indicator for the target locus (due to the reduced cross-over frequency between the target locus and the marker). Thus, in one example, closely linked loci such as a marker locus and a second locus (e.g., a given marker or a QTL) display an inter-locus cross-over frequency of about 10% or less, about 9% or less, about 8% or less, about 7% or less, about 6% or less, about 5% or less, about 4% or less, about 3% or less, or about 2% or less. In some examples, the relevant loci (e.g., a marker locus and a target locus such as a QTL) display a recombination a frequency of about 1% or less, e.g., about 0.75% or less, about 0.5% or less, or about 0.25% or less. Thus, the loci are about 10 cM, 9 cM, 8 cM, 7 cM, 6 cM, 5 cM, 4 cM, 3 cM, 2 cM, 1 cM, 0.75 cM, 0.5 cM or 0.25 cM or less apart. Put another way, two loci that are localized to the same chromosome, and at such a distance that recombination between the two loci occurs at a frequency of no more than 10% (e.g., about 9%, 8%, 7%, 6%, 5%, 4%, 3%, 2%, 1%, 0.75%, 0.5%, 0.25%, or less) are said to be proximal to each other.

Many marker alleles can be detected or selected for or against. Optionally, one, two, three, or more marker allele(s) can be identified in or introgressed into the plant. Plants or germplasm frequently are identified that have at least one favorable allele that positively correlates with tolerance or improved tolerance. However, it is useful for exclusionary purposes during breeding to also identify alleles that negatively correlate with tolerance, to eliminate such plants or germplasm from subsequent rounds of breeding.

The identification of favorable marker alleles may be germplasm-specific. The determination of which marker alleles correlate with tolerance (or non-tolerance) is determined for the particular germplasm under study. One of skill recognizes that methods for identifying favorable alleles are routine and well known, and, furthermore, that the identification and use of such favorable alleles is well within the scope of the invention.

Numerous markers disclosed herein have been found to be associated with or to correlate with tolerance, improved tolerance, or susceptibility/sensitivity to mesotrione and/or isoxazole herbicides in soybean. Generally, markers that map closer to the QTL mapped to linkage group L and associated with tolerance or sensitivity to mesotrione and/or isoxazole herbicides are superior to markers that map farther from the QTL. In some examples, a marker used to determine the presence or absence of a QTL mapping to soybean linkage group L and associated with tolerance or sensitivity to mesotrione and/or isoxazole herbicides includes one or more of SATT495, P10649C-3, SATT182, S03859-1, S00224-1, SATT388, SATT313, and SATT613, or other markers above marker SATT613 on LG-L. Additional useful and/or relevant markers include S03859-1-A, S08103-1-Q1, S08104-1-Q1, S08106-1-Q1, S08110-1-Q1, S08111-1-Q1, S08115-2-Q1, S08117-1-Q1, S08119-1-Q1, S08118-1-Q1, S08116-1-Q1, S08114-1-Q1, S08113-1-Q1, S08112-1-Q1, S08108-1-Q1, S08101-2-Q1, S08101-3-Q1, S08101-4-Q1, S08105-1-Q1, S08102-1-Q1, S08107-1-Q1, S08109-1-Q1, and S08101-1-Q1. Any marker assigned to soybean linkage group L and linked or closely linked to a marker disclosed herein as associated with tolerance or sensitivity to mesotrione and/or isoxazole herbicides may be used. Generally, a linked marker is within 50 cM of the referenced marker or trait, and a closely linked marker is within 10 cM of the referenced marker or trait. Updated information regarding markers assigned to soybean linkage group L may be found on the USDA's Soybase website. Further, linkage group L is now formally referred to as chromosome #19.

Intervals defined by markers flanking the QTL associated with tolerance or sensitivity to mesotrione and/or isoxazole herbicides are useful, as well. For interval determination, the genomic DNA of soybean germplasm is typically tested for the presence of at least two of the foregoing molecular markers, one marker on each side of the QTL. Examples of such intervals include the interval flanked by and including SATT613 and above on LG-L, the interval flanked by and including markers SATT495 and SATT613, the interval flanked by and including SATT313 and above on LG-L, the interval flanked by and including markers SATT495 and SATT313, the interval flanked by and including markers SATT495 and SATT388, the interval flanked by and including markers P10649C-3 and SATT182, the interval flanked by and including markers S04867-1-A and S03859-1-A, the interval flanked by and including markers S08110-1-Q1 and S08010-1-Q1, the interval flanked by and including markers S08117-1-Q1 and S08010-1-Q1, the interval flanked by and including markers S08110-1-Q1 and S08105-1-Q1, the interval flanked by and including markers S08117-1-Q1 and S08105-1-Q1, and the interval flanked by and including markers S08113-1-Q1 and S08105-1-Q1.

Initial fine mapping isolated the location of the QTL associated with herbicide tolerance/sensitivity to a ~56 kb interval between marker S08117-1-Q1 and S08105-1-Q1 on linkage group L. Further fine mapping refined the location of the QTL to a ~44 kb interval between marker S08113-1-Q1 and S08105-1-Q1 on linkage group L. Accordingly, markers that map within the interval defined by and including these markers are particularly useful for selecting for this QTL. These markers include S08117-1-Q1, S08119-1-Q1, S08118-1-Q1, S08116-1-Q1, S08101-1-Q1, S08112-1-Q1, S08108-1-Q1, S08101-1-Q1, S08101-2-Q1, S08101-3-Q1, S08101-4-Q1, and S08105-1-Q1. In some examples, the markers are S08112-1-Q1, S08108-1-Q1, S08101-2-Q1, S08101-3-Q1, and S08101-4-Q1.

Methods of introgressing tolerance to mesotrione and/or isoxazole herbicides into non-tolerant or less-tolerant soybean germplasm are provided. Any method for introgressing QTLs into soybean plants can be used. In some examples, a first soybean germplasm that contains tolerance or sensitivity to mesotrione and/or isoxazole herbicides derived from the QTL mapped to linkage group L which is associated with tolerance or sensitivity to mesotrione and/or isoxazole herbicides and a second soybean germplasm that lacks tolerance or sensitivity to mesotrione and/or isoxazole herbicides derived from the QTL mapped to linkage group L are provided. The first soybean plant may be crossed with the second soybean plant to provide progeny soybeans. Phenotypic and/or marker screening is performed on the progeny plants to determine the presence of tolerance or sensitivity to mesotrione and/or isoxazole herbicides derived from the QTL mapped to linkage group L. Progeny that test positive for the presence of tolerance or sensitivity to mesotrione and/or isoxazole herbicides derived from the QTL mapped to linkage group L can be selected.

In some examples, the screening and selection are performed by using marker-assisted selection using any marker or combination of markers on major linkage group L provided. Any method of identifying the presence or absence of these markers may be used, including for example single-strand conformation polymorphism (SSCP) analysis, base excision sequence scanning (BESS), RFLP analysis, heteroduplex analysis, denaturing gradient gel electrophoresis, temperature gradient electrophoresis, allelic PCR, ligase chain reaction direct sequencing, mini sequencing, nucleic acid hybridization, or micro-array-type detection.

Amplification primers for amplifying marker loci and suitable marker probes to detect marker loci or to genotype SNP alleles are provided, for example, in Table C and the related sequence listing (SEQ ID NOs: 1-121). Optionally, other sequences to either side of the given primers can be used in place of the given primers, so long as the primers can amplify a region that includes the allele to be detected. Further, it will be appreciated that the precise probe to be used for detection can vary, e.g., any probe that can identify the region of a marker amplicon to be detected can be substituted for those examples provided herein. The configuration of the amplification primers and detection probes can, of course, vary. Thus, the invention is not limited to the primers and probes specifically recited herein.

Systems, including automated systems for selecting plants that comprise a marker of interest and/or for correlating presence of the marker with tolerance are also provided. These systems can include probes relevant to marker locus detection, detectors for detecting labels on the probes, appropriate fluid handling elements and temperature controllers that mix probes and templates and/or amplify templates, and systems and/or instructions that correlate label detection to the presence of a particular marker locus or allele.

Kits are also provided. For example, a kit can include appropriate primers or probes for detecting tolerance associated marker loci and instructions for using the primers or probes for detecting the marker loci and correlating the loci with predicted tolerance to mesotrione and/or isoxazole herbicides. The kits can further include packaging materials for packaging the probes, primers, or instructions; controls, such as control amplification reactions that include probes, primers, or template nucleic acids for amplifications; molecular size markers; or the like.

Isolated nucleic acid fragments comprising a nucleic acid sequence coding for soybean tolerance or sensitivity to mesotrione and/or isoxazole herbicides, are provided. The nucleic acid fragment comprises at least a portion of a nucleic acid belonging to linkage group L. The nucleic acid fragment is capable of hybridizing under stringent conditions to a nucleic acid of a soybean cultivar tolerant to mesotrione and/or isoxazole herbicides containing a QTL associated with mesotrione and/or isoxazole herbicide tolerance that is located on major linkage group L.

Vectors comprising such nucleic acid fragments, expression products of such vectors expressed in a host compatible therewith, antibodies to the expression product (both polyclonal and monoclonal), and antisense nucleic acid to the nucleic acid fragment are also provided.

Seed of a soybean produced by crossing a soybean variety having mesotrione and/or isoxazole herbicide tolerance QTL located on major linkage group L in its genome with another soybean variety, and progeny thereof, are provided.

Detection Methods

Any suitable detection method known in the art can be used to detect the markers, QTL, or traits discussed herein. In some examples, the presence of marker loci is directly detected in unamplified genomic DNA by performing a Southern blot on a sample of genomic DNA using probes to the marker loci. In other examples, amplification based techniques are employed. PCR, RT-PCR, and LCR are in particularly broad use as amplification and amplification-detection methods for amplifying nucleic acids of interest, thus facilitating detection of markers. Procedures for performing Southern blotting, amplification (PCR, LCR, or the like), and many other nucleic acid detection methods are well established and are taught, e.g., in Sambrook et al., *Molecular Cloning—A Laboratory Manual* (3d ed.), Vol. 1-3, Cold Spring Harbor Laboratory, Cold Spring Harbor, N.Y., 2000 ("Sambrook"); *Current Protocols in Molecular Biology*, F. M. Ausubel et al., eds., Current Protocols, a joint venture between Greene Publishing Associates, Inc. and John Wiley & Sons, Inc., (supplemented through 2002) ("Ausubel")) and *PCR Protocols A Guide to Methods and Applications* (Innis et al. eds) Academic Press Inc. San Diego, Calif. (1990) (Innis). Additional details regarding detection of nucleic acids in plants can also be found, e.g., in *Plant Molecular Biology* (1993) Croy (ed.) BIOS Scientific Publishers, Inc.

Typically, molecular markers are detected by any established method available, including, without limitation, allele specific hybridization (ASH), real-time PCR assays for detecting single nucleotide polymorphisms (SNP), amplified fragment length polymorphism (AFLP) detection, amplified variable sequence detection, randomly amplified polymorphic DNA (RAPD) detection, restriction fragment length polymorphism (RFLP) detection, self-sustained sequence replication detection, simple sequence repeat (SSR) detection, single-strand conformation polymorphisms (SSCP) detection, isozyme markers detection, or the like. While the exemplary markers provided in the tables herein are either SSR or SNP markers, any of the aforementioned marker types can be employed to identify chromosome segments encompassing genetic element that contribute to superior agronomic performance (e.g., tolerance or improved tolerance).

In another example, the presence or absence of a molecular marker is determined by nucleotide sequencing of the polymorphic marker region. This method is readily adapted to high throughput analysis, as are the other methods noted above, e.g., using available high throughput sequencing methods such as sequencing by hybridization.

In general, the majority of genetic markers rely on one or more properties of nucleic acids for their detection. For example, some techniques for detecting genetic markers utilize hybridization of a probe nucleic acid to nucleic acids corresponding to the genetic marker (e.g., amplified nucleic acids produced using genomic soybean DNA as a template). Hybridization formats, including but not limited to solution phase, solid phase, mixed phase, or in situ hybridization assays are useful for allele detection. An extensive guide to the hybridization of nucleic acids is found in Tijssen (1993) *Laboratory Techniques in Biochemistry and Molecular Biology—Hybridization with Nucleic Acid Probes* Elsevier, New York, as well as in Sambrook and Ausubel.

For example, markers that comprise restriction fragment length polymorphisms (RFLP) are detected, e.g., by hybridizing a probe which is typically a sub-fragment (or a synthetic oligonucleotide corresponding to a sub-fragment) of the nucleic acid to be detected to restriction-digested genomic DNA. The restriction enzyme is selected to provide restriction fragments of at least two alternative (or polymorphic) lengths in different individuals or populations. Determining one or more restriction enzymes that produce informative fragments for each cross is a simple procedure. After separation by length in an appropriate matrix (e.g., agarose, polyacrylamide, etc.) and transfer to a membrane (e.g., nitrocellulose, nylon, etc.), the labeled probe is hybridized under conditions which result in equilibrium binding of the probe to the target followed by removal of excess probe by washing.

In some examples, molecular markers are detected using a suitable PCR-based detection method. This includes methods where the size or sequence of the PCR amplicon is indicative of the absence or presence of the marker (e.g., a particular marker allele), as well as methods where a labeled allele-specific probe is used for detection (e.g., a TaqMan® assay). In these types of methods, PCR primers and, optionally, probes are hybridized to the conserved regions flanking the polymorphic marker region. Suitable primers can be designed using any suitable method. It is not intended that the invention be limited to any particular primer or primer pair. For example, primers can be designed using any suitable software program, such as LASERGENE®.

In some examples, primers are labeled by any suitable means (e.g., using a non-radioactive fluorescent tag) to allow for rapid visualization of the different size amplicons following an amplification reaction without any additional labeling step or visualization step. In some examples, the primers are not labeled, and the amplicons are visualized following their size resolution, e.g., following agarose gel electrophoresis. In some examples, ethidium bromide staining of the PCR amplicons following size resolution allows visualization of the different size amplicons.

The primers used to amplify the marker loci and alleles herein are not limited to amplifying the entire region of the relevant locus. In some examples, marker amplification produces an amplicon at least 20 nucleotides in length, or alternatively, at least 50 nucleotides in length, or alternatively, at least 100 nucleotides in length, or alternatively, at least 200 nucleotides in length, or up to and including the full length of the amplicon.

Nucleic acid probes to the marker loci can also be cloned and/or synthesized. Any suitable label can be used with a probe. Detectable labels suitable for use with nucleic acid probes include, for example, any composition detectable by spectroscopic, radioisotopic, photochemical, biochemical, immunochemical, electrical, optical or chemical means. Useful labels include biotin for staining with labeled streptavidin conjugate, magnetic beads, fluorescent dyes, radiolabels, enzymes, and colorimetric labels. Other labels include ligands, which bind to antibodies labeled with fluorophores, chemiluminescent agents, and enzymes. A probe can also constitute radiolabelled PCR primers that are used to generate a radiolabelled amplicon. Methods and reagents for labeling nucleic acids and corresponding detection strategies can be found, e.g., in Haugland (1996) *Handbook of Fluorescent Probes and Research Chemicals Sixth Edition* by Molecular Probes, Inc. (Eugene Oreg.); or Haugland (2001) *Handbook of Fluorescent Probes and Research Chemicals Eighth Edition* by Molecular Probes, Inc. (Eugene Oreg.).

Separate detection probes can also be omitted in amplification/detection methods, e.g., by performing a real time amplification reaction that detects product formation by modification of the relevant amplification primer upon incorporation into a product, incorporation of labeled nucleotides into an amplicon, or by monitoring changes in molecular rotation properties of amplicons as compared to unamplified precursors (e.g., by fluorescence polarization).

In alternative embodiments, in silico methods can be used to detect the marker loci of interest. For example, the sequence of a nucleic acid comprising the marker locus of interest can be stored in a computer. The desired marker locus sequence or its homolog can be identified using an appropriate nucleic acid search algorithm as provided by, for example, in such readily available programs as BLAST, or even simple word processors.

Real Time Amplification/Detection Methods:

In one aspect, real time PCR or LCR is performed on the amplification mixtures described herein, e.g., using molecular beacons or TaqMan™ probes. A molecular beacon (MB) is an oligonucleotide or peptide nucleic acid (PNA) which, under appropriate hybridization conditions, self-hybridizes to form a stem and loop structure. The MB has a label and a quencher at the termini of the oligonucleotide or PNA; thus, under conditions that permit intra-molecular hybridization, the label is typically quenched (or at least altered in its fluorescence) by the quencher. Under conditions where the MB does not display intra-molecular hybridization (e.g., when bound to a target nucleic acid, e.g., to a region of an amplicon during amplification), the MB label is unquenched and signal is detected. Standard methods of making and using MBs are known and MBs and reagents are commercially available. See also, e.g., Leone et al. (1995) "Molecular beacon probes combined with amplification by NASBA enable homogenous real-time detection of RNA." Nucleic Acids Res. 26:2150-2155; Tyagi and Kramer (1996) "Molecular beacons: probes that fluoresce upon hybridization" Nature Biotechnology 14:303-308; Blok and Kramer (1997) "Amplifiable hybridization probes containing a molecular switch" Mol Cell Probes 11:187-194; Hsuih et al. (1997) "Novel, ligation-dependent PCR assay for detection of hepatitis C in serum" J Clin Microbiol 34:501-507; Kostrikis et al. (1998) "Molecular beacons: spectral genotyping of human alleles" Science 279:1228-1229; Sokol et al. (1998) "Real time detection of DNA:RNA hybridization in living cells" Proc. Natl. Acad. Sci. U.S.A. 95:11538-11543; Tyagi et al. (1998) "Multicolor molecular beacons for allele discrimination" Nature Biotechnology 16:49-53; Bonnet et al. (1999) "Thermodynamic basis of the chemical specificity of structured DNA probes" Proc. Natl. Acad. Sci. U.S.A. 96:6171-6176; Fang et al. (1999) "Designing a novel molecular beacon for surface-immobilized DNA hybridization studies" J. Am. Chem. Soc. 121:2921-2922; Marras et al. (1999) "Multiplex detection of single-nucleotide variation using molecular beacons" Genet. Anal. Biomol. Eng. 14:151-156; and Vet et al. (1999) "Multiplex detection of four pathogenic retroviruses using molecular beacons" Proc. Natl. Acad. Sci. U.S.A. 96:6394-6399. See also, e.g., U.S. Pat. No. 5,925,517 (Jul. 20, 1999) to Tyagi et al. entitled "Detectably labeled dual conformation oligonucleotide probes, assays and kits;" U.S. Pat. No. 6,150,097 to Tyagi et al (Nov. 21, 2000) entitled "Nucleic acid detection probes having non-FRET fluorescence quenching and kits and assays including such probes" and U.S. Pat. No. 6,037,130 to Tyagi et al (Mar. 14, 2000), entitled "Wavelength-shifting probes and primers and their use in assays and kits."

PCR detection and quantification using dual-labeled fluorogenic oligonucleotide probes can be done, using, for example, TaqMan® probes. These probes are composed of short (e.g., 10-40 bases) oligodeoxynucleotides that are labeled with two different fluorescent dyes. On the 5' terminus of each probe is a reporter dye, and on the 3' terminus of each probe a quenching dye is found. The oligonucleotide probe sequence is complementary to an internal target sequence present in a PCR amplicon. When the probe is intact, energy transfer occurs between the two fluorophores and emission from the reporter is quenched by the quencher via FRET. During the extension phase of PCR, the probe is cleaved by 5' nuclease activity of the polymerase used in the reaction, thereby releasing the reporter from the oligonucleotide-quencher and producing an increase in reporter emission intensity. Accordingly, TaqMan® probes are oligonucleotides that have a label and a quencher, where the label is released during amplification by the exonuclease action of the polymerase used in amplification. This provides a real time measure of amplification during synthesis. A variety of TaqMan® reagents are commercially available, e.g., from Applied Biosystems (Division Headquarters in Foster City, Calif.) as well as from a variety of specialty vendors such as Biosearch Technologies (e.g., black hole quencher probes).

In general, synthetic methods for making oligonucleotides, including probes, primers, molecular beacons, PNAs, LNAs (locked nucleic acids), etc., are well known. For example, oligonucleotides can be synthesized chemically according to the solid phase phosphoramidite triester method described by Beaucage and Caruthers (1981), Tetrahedron Letts 22:1859-1862, e.g., using a commercially available automated synthesizer. Oligonucleotides, including modified oligonucleotides and PNAs, can also be ordered from a variety of commercial sources known to persons of skill.

Additional Details Regarding Amplified Variable Sequences, SSR, AFLP ASH, SNPs, and Isozyme Markers Amplified variable sequences refer to amplified sequences of the plant genome, which exhibit high nucleic acid residue variability between members of the same species. All organisms have variable genomic sequences and each organism (with the exception of a clone) has a different set of variable sequences. Once identified, the presence of specific variable sequence can be used to predict phenotypic traits. Typically, DNA from the plant serves as a template for amplification with primers that flank a variable sequence of DNA. The variable sequence is amplified and then sequenced.

Alternatively, self-sustained sequence replication can be used to identify genetic markers. Self-sustained sequence replication refers to a method of nucleic acid amplification using target nucleic acid sequences which are replicated exponentially in vitro under substantially isothermal conditions by using three enzymatic activities involved in retroviral replication: (1) reverse transcriptase, (2) RNase H, and (3) a DNA-dependent RNA polymerase (Guatelli et al. (1990) Proc Natl Acad Sci USA 87:1874). By mimicking the retroviral strategy of RNA replication by means of cDNA intermediates, this reaction accumulates cDNA and RNA copies of the original target.

Amplified fragment length polymorphisms (AFLP), which are amplified before or after cleavage by a restriction endonuclease, can also be used as genetic markers (Vos et al. (1995) Nucl Acids Res 23:4407). The amplification step allows easier detection of specific restriction fragments. AFLP allows the detection large numbers of polymorphic markers and has been used for genetic mapping of plants (Becker et al. (1995) Mol Gen Genet 249:65; and Meksem et al. (1995) Mol Gen Genet 249:74).

Allele-specific hybridization (ASH) can be used to identify the genetic markers. ASH technology is based on the stable annealing of a short, single-stranded, oligonucleotide probe to a completely complementary single-strand target nucleic acid. Detection is via an isotopic or non-isotopic label attached to the probe.

For each polymorphism, two or more different ASH probes are designed to have identical DNA sequences except at the polymorphic nucleotides. Each probe will have exact homology with one allele sequence so that the range of probes can distinguish all the known alternative allele sequences. Each probe is hybridized to the target DNA. With appropriate probe design and hybridization conditions, a single-base mismatch between the probe and target DNA will prevent hybridization. In this manner, only one of the alternative probes will hybridize to a target sample that is homozygous or homogenous for an allele. Samples that are heterozygous or heterogeneous for two alleles will hybridize to both of two alternative probes.

ASH markers are used as dominant markers where the presence or absence of only one allele is determined from hybridization or lack of hybridization by only one probe. The alternative allele may be inferred from the lack of hybridization. ASH probe and target molecules are optionally RNA or DNA; the target molecules are any length of nucleotides beyond the sequence that is complementary to the probe; the probe is designed to hybridize with either strand of a DNA target; the probe ranges in size to conform to variously stringent hybridization conditions, etc.

PCR allows the target sequence for ASH to be amplified from low concentrations of nucleic acid in relatively small volumes. Otherwise, the target sequence from genomic DNA is digested with a restriction endonuclease and size separated by gel electrophoresis. Hybridizations typically occur with the target sequence bound to the surface of a membrane or, as described in U.S. Pat. No. 5,468,613, the ASH probe sequence may be bound to a membrane. In one example, ASH data are typically obtained by amplifying nucleic acid fragments (amplicons) from genomic DNA using PCR, transferring the amplicon target DNA to a membrane in a dot-blot format, hybridizing a labeled oligonucleotide probe to the amplicon target, and observing the hybridization dots by autoradiography.

Single nucleotide polymorphisms (SNP) are markers that consist of a shared sequence differentiated on the basis of a single nucleotide. Typically, this distinction is detected by differential migration patterns of an amplicon comprising the SNP on, e.g., an acrylamide gel. However, alternative modes of detection, such as hybridization, e.g., ASH, or RFLP analysis are also appropriate.

Isozyme markers can be employed as genetic markers, e.g., to track markers other than the tolerance markers herein, or to track isozyme markers linked to the markers herein. Isozymes are multiple forms of enzymes that differ from one another in their amino acid sequence, and therefore their nucleic acid sequences. Some isozymes are multimeric enzymes containing slightly different subunits. Other isozymes are either multimeric or monomeric but have been cleaved from the proenzyme at different sites in the amino acid sequence. Isozymes can be characterized and analyzed at the protein level, or alternatively, isozymes, which differ at the nucleic acid level, can be determined. In such cases any of the nucleic acid based methods described herein can be used to analyze isozyme markers.

Marker Assisted Selection and Breeding of Plants

The identification of markers associated with a particular phenotypic trait can allow for selection of plants possessing that trait, for example, via marker assisted selection (MAS). In general, the application of MAS uses the identification of a population of tolerant plants and genetic mapping of the tolerance trait. Polymorphic loci in the vicinity of the mapped tolerance trait are chosen as potential tolerance markers. Typically, a marker locus closest to the tolerance locus is a preferred marker. Linkage analysis is then used to determine which polymorphic marker allele sequence demonstrates a statistical likelihood of co-segregation with the tolerant phenotype (thus, a "tolerance marker allele"). Following identification of a marker allele for co-segregation with the tolerance allele, it is possible to use this marker for rapid, accurate screening of plant lines for the tolerance allele without the need to grow the plants through their life cycle and await phenotypic evaluations, and furthermore, permits genetic selection for the particular tolerance allele even when the molecular identity of the actual tolerance QTL is anonymous. Tissue samples can be taken, for example, from the first leaf of the plant and screened with the appropriate molecular marker, and within days it is determined which progeny will advance. Linked markers also remove the impact of environmental factors that can often influence phenotypic expression.

After a desired phenotype (e.g., tolerance or sensitivity to mesotrione and/or isoxazole herbicides) and a polymorphic chromosomal marker locus are determined to cosegregate, the polymorphic marker locus can be used to select for marker alleles that segregate with the desired tolerance phenotype. This general process is typically called marker-assisted selection (MAS). In brief, a nucleic acid corresponding to the marker nucleic acid is detected in a biological sample from a plant to be selected. This detection can take the form of hybridization of a probe nucleic acid to a marker allele or amplicon thereof, e.g., using allele-specific hybridization, Southern analysis, northern analysis, in situ hybridization, hybridization of primers followed by PCR amplification of a region of the marker, or the like. After the presence (or absence) of a particular marker in the biological sample is verified, the plant is selected, e.g., used to make progeny plants by selective breeding.

Soybean plant breeders desire combinations of tolerance loci with genes for high yield and other desirable traits to develop improved soybean varieties. Screening large numbers of samples by non-molecular methods (e.g., trait evaluation in soybean plants) can be expensive, time consuming, and unreliable. Use of the polymorphic markers described herein genetically linked to tolerance loci provide effective methods for selecting tolerant varieties in breeding programs. For example, one advantage of marker-assisted selection over field evaluations for tolerance is that MAS can be done at any time of year, regardless of the growing season. Moreover, environmental effects are largely irrelevant to marker-assisted selection. When a population is segregating for multiple loci affecting one or multiple traits, e.g., multiple loci involved in tolerance, or multiple loci each involved in tolerance or tolerance to different herbicides, the efficiency of MAS compared to phenotypic screening becomes even greater, because all of the loci can be evaluated in the lab together from a single sample of DNA. In the present instance, for linkage group L, relevant markers include: SATT495, P10649C-3, SATT182, S03859-1, S00224-1, SATT388, SATT313, and SATT613 (or other markers above SATT613). Additional relevant markers on linkage group L include S03859-1-A, S08103-1-Q1, S08104-1-Q1, S08106-1-Q1, S08110-1-Q1, S08111-1-Q1, S08115-2-Q1, S08117-1-Q1, S08119-1-Q1, S08118-1-Q1, S08116-1-Q1, S08114-1-Q1, S08113-1-Q1, S08112-1-Q1, S08108-1-Q1, S08101-2-Q1, S08101-3-Q1, S08101-4-Q1, S08105-1-Q1, S08102-1-Q1, S08107-1-Q1, S08109-1-Q1, and S08101-1-Q1, and markers for other traits, transgenes, and/or loci can be assayed simultaneously or sequentially in a single sample or population of samples. Markers for other traits, transgenes, and/or loci can be assayed simultaneously or sequentially in a single sample or population of samples.

Another use of MAS in plant breeding is to assist the recovery of the recurrent parent genotype by backcross breeding. Backcross breeding is the process of crossing a progeny back to one of its parents or parent lines. Backcrossing is usually done for the purpose of introgressing one or a few loci from a donor parent (e.g., a parent comprising desirable tolerance marker loci) into an otherwise desirable genetic background from the recurrent parent (e.g., an otherwise high yielding soybean line). The more cycles of backcrossing that are done, the greater the genetic contribution of the recurrent parent to the resulting introgressed variety. This is often necessary, because tolerant plants may be otherwise undesirable, e.g., due to low yield, low fecundity, or the like. In contrast, strains which are the result of intensive breeding programs may have excellent yield, fecundity or the like, merely being deficient in one desired trait, such as tolerance or sensitivity to mesotrione and/or isoxazole herbicides.

The determination of the presence and/or absence of a particular genetic marker or allele, e.g., SATT495, P10649C-3, SATT182, S03859-1, S00224-1, SATT388, SATT313, SATT613 (including markers above SATT613), S03859-1-A, S08103-1-Q1, S08104-1-Q1, S08106-1-Q1, S08110-1-Q1, S08111-1-Q1, S08115-2-Q1, S08117-1-Q1, S08119-1-Q1, S08118-1-Q1, S08116-1-Q1, S08114-1-Q1, S08113-1-Q1, S08112-1-Q1, S08108-1-Q1, S08101-2-Q1, S08101-3-Q1, S08101-4-Q1, S08105-1-Q1, S08102-1-Q1, S08107-1-Q1, S08109-1-Q1, or S08101-1-Q1, in the genome of a plant exhibiting a preferred phenotypic trait can be made by any method noted herein. If the nucleic acids from the plant are positive for a desired genetic marker, the plant can be self fertilized to create a true breeding line with the same genotype, or it can be crossed with a plant with the same marker or with other desired characteristics to create a sexually crossed hybrid generation.

Introgression of Favorable Alleles—Efficient Crossing of Tolerance Markers into Other Lines One application of MAS is to use the tolerance or improved tolerance markers to increase the efficiency of an introgression or backcrossing effort aimed at introducing a tolerance QTL into a desired (typically high yielding) background. In marker assisted backcrossing of specific markers (and associated QTL) from a donor source, e.g., to an elite genetic background, one selects among progeny or backcross progeny for the donor trait.

Thus, the markers and methods can be utilized to guide marker assisted selection or breeding of soybean varieties with the desired complement (set) of allelic forms of chromosome segments associated with herbicide tolerance as well as markers associated with superior agronomic performance (tolerance, along with any other available markers for yield, disease tolerance, etc.). Any of the disclosed marker alleles can be introduced into a soybean line via, for example, introgression, traditional breeding, or transformation, or a combination thereof, to yield a soybean plant with superior agronomic performance. The number of alleles associated with mesotrione and/or isoxazole tolerance that can be introduced or be present in a soybean plant ranges from 1 to the number of alleles disclosed herein, each integer of which is incorporated herein as if explicitly recited.

Methods of making a progeny soybean plant, and these progeny soybean plants having tolerance or susceptibility to mesotrione and/or isoxazole, are provided. These methods comprise crossing a first parent soybean plant with a second soybean plant and growing the female soybean plant under plant growth conditions to yield soybean plant progeny. Such soybean plant progeny can be assayed for alleles associated with tolerance and, thereby, the desired progeny selected. Such progeny plants or seed can be sold commercially for soybean production, used for food, processed to obtain a desired constituent of the soybean, or further utilized in subsequent rounds of breeding. At least one of the first or second soybean plants is a soybean plant comprising at least one of the allelic forms of the markers provided, such that the progeny are capable of inheriting the allele.

Inheritance of the desired tolerance allele can be traced, such as from progenitor or descendant lines in the subject soybean plants pedigree such that the number of generations separating the soybean plants being subject to the methods will generally be from 1 to 20, commonly 1 to 5, and typically 1, 2, or 3 generations of separation, and quite often a direct descendant or parent of the soybean plant will be subject to the method (i.e., 1 generation of separation).

Positional Cloning

The molecular marker loci and alleles associated with tolerance or susceptibility to mesotrione and/or isoxazole, e.g., SATT495, P10649C-3, SATT182, S03859-1, S00224-1, SATT388, SATT313, SATT613 (including markers above SATT613), S03859-1-A, S08103-1-Q1, S08104-1-Q1, S08106-1-Q1, S08110-1-Q1, S08111-1-Q1, S08115-2-Q1, S08117-1-Q1, S08119-1-Q1, S08118-1-Q1, S08116-1-Q1, S08114-1-Q1, S08113-1-Q1, S08112-1-Q1, S08108-1-Q1, S08101-2-Q1, S08101-3-Q1, S08101-4-Q1, S08105-1-Q1, S08102-1-Q1, S08107-1-Q1, S08109-1-Q1, and S08101-1-Q1, can be used, as indicated previously, to identify a tolerance QTL, which can be cloned by well-established procedures, e.g., as described in detail in Ausubel, Berger and Sambrook.

These tolerance clones are first identified by their genetic linkage to markers provided herein. Isolation of a nucleic acid of interest is achieved by any number of methods as discussed in detail in such references as Ausubel, Berger and Sambrook, herein, and Clark, ed. (1997) Plant Molecular Biology: A Laboratory Manual Springer-Verlag, Berlin.

For example, "positional gene cloning" uses the proximity of a tolerance marker to physically define an isolated chromosomal fragment containing a tolerance QTL gene. The isolated chromosomal fragment can be produced by such well known methods as digesting chromosomal DNA with one or more restriction enzymes, or by amplifying a chromosomal region in a polymerase chain reaction (PCR), or any suitable alternative amplification reaction. The digested or amplified fragment is typically ligated into a vector suitable for replication, and, e.g., expression, of the inserted fragment. Markers that are adjacent to an open reading frame (ORF) associated with a phenotypic trait can hybridize to a DNA clone (e.g., a clone from a genomic DNA library), thereby identifying a clone on which an ORF (or a fragment of an ORF) is located. If the marker is more distant, a fragment containing the open reading frame is identified by successive rounds of screening and isolation of clones which together comprise a contiguous sequence of DNA, a process termed "chromosome walking", resulting in a "contig" or "contig map." Protocols sufficient to guide one of skill through the isolation of clones associated with linked markers are found in, e.g. Berger, Sambrook and Ausubel, all herein.

Variant sequences have a high degree of sequence similarity. For polynucleotides, conservative variants include those sequences that, because of the degeneracy of the genetic code, encode the amino acid sequence of one of the native recombinase polypeptides. Variants such as these can be identified with the use of well-known molecular biology techniques, as, for example, with polymerase chain reaction (PCR) and hybridization techniques. Variant polynucleotides also include synthetically derived nucleotide sequences, such as those generated, for example, by using site-directed mutagenesis but which still encode a recombinase protein. Generally, variants of a particular polynucleotide will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by known sequence alignment programs and parameters.

Variants of a particular polynucleotide (the reference nucleotide sequence) can also be evaluated by comparison of the percent sequence identity between the polypeptide encoded by a variant polynucleotide and the polypeptide encoded by the reference polynucleotide. Percent sequence identity between any two polypeptides can be calculated using sequence alignment programs and parameters described. Where any given pair of polynucleotides is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

Variant proteins include proteins derived from the native protein by deletion, addition, and/or substitution of one or more amino acids to the N-terminal, internal region(s), and/or C-terminal end of the native protein. Variant proteins can be biologically active, that is they continue to possess the desired biological activity of the native protein, for example a variant recombinase can implement a recombination event between appropriate recombination sites. Such variants may result from, for example, genetic polymorphism or from human manipulation. A biologically active variant of a protein may differ from that protein by as few as 1-15 amino acid residues, as few as 1-10, such as 6-10, as few as 5, as few as 4, 3, 2, or even 1 amino acid residue.

Sequence relationships can be analyzed and described using computer-implemented algorithms. The sequence relationship between two or more polynucleotides or two or more polypeptides can be determined by generating the best alignment of the sequences, and scoring the matches and the gaps in the alignment, which yields the percent sequence identity, and the percent sequence similarity. Polynucleotide relationships can also be described based on a comparison of the polypeptide each encodes. Many programs and algorithms for the comparison and analysis of sequences are available.

Unless otherwise stated, sequence identity/similarity values provided herein refer to the value obtained using GAP Version 10 (GCG, Accelrys, San Diego, Calif.) using the following parameters: % identity and % similarity for a nucleotide sequence using a gap creation penalty weight of 50 and a gap length extension penalty weight of 3, and the nwsgapdna.cmp scoring matrix; % identity and % similarity for an amino acid sequence using a GAP creation penalty weight of 8 and a gap length extension penalty of 2, and the BLOSUM62 scoring matrix (Henikoff & Henikoff (1989) Proc Natl Acad Sci USA 89:10915).

GAP uses the algorithm of Needleman & Wunsch (1970) J Mol Biol 48:443-453, to find an alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. GAP presents one member of the family of best alignments.

Sequence identity, or identity, is a measure of the residues in the two sequences that are the same when aligned for maximum correspondence. Sequences, particularly polypeptides, that differ by conservative substitutions are said to have sequence similarity or similarity. Means for making this adjustment are known, and typically involve scoring a conservative substitution as a partial rather than a full mismatch. For example, where an identical amino acid is given a score of 1 and a non-conservative substitution is given a score of zero, a conservative substitution is given a score between zero and 1. The scoring of conservative substitutions is calculated using the selected scoring matrix (BLOSUM62 by default for GAP).

Equivalent positions between two or more polynucleotides, and/or polypeptides can be identified using any searching, sequence assembly, and/or alignment tool including, but not limited to, BLAST, GAP, PILEUP, FrameAlign, Sequencher, or similar tools. In some examples, GAP alignment can be used to identify equivalent positions, using the following parameters: for a nucleotide sequence using a gap creation penalty weight of 50 and a gap length extension penalty weight of 3, and the nwsgapdna.cmp scoring matrix; for an amino acid sequence using a gap creation penalty weight of 8 and a gap length extension penalty of 2, and the BLOSUM62 scoring matrix (Henikoff & Henikoff (1989) Proc Natl Acad Sci USA 89:10915). In some examples, PILEUP can be used to identify equivalent positions, using the following parameters for a nucleotide sequence: a gap weight of 5 and a gap length weight of 1, and the pileupdna.cmp scoring matrix; for an amino acid sequence using a gap weight of 8 and a gap length weight of 2, and the BLOSUM62 scoring matrix (Henikoff & Henikoff (1989) Proc Natl Acad Sci USA 89:10915).

Proteins may be altered in various ways including amino acid substitutions, deletions, truncations, and insertions. Methods for such manipulations are generally known. Methods for mutagenesis and nucleotide sequence alterations are described, for example, in Kunkel (1985) Proc Natl Acad Sci USA 82:488-492; Kunkel et al. (1987) Methods in Enzymol 154:367-382; U.S. Pat. No. 4,873,192; Walker & Gaastra, eds. (1983) Techniques in Molecular Biology (MacMillan Publishing Company, New York) and the references cited therein. Guidance as to appropriate amino acid substitutions that do not affect biological activity of the protein of interest may be found in the model of Dayhoff et al. (1978) Atlas of Protein Sequence and Structure (Natl Biomed Res Found, Washington, D.C.). Conservative substitutions, such as exchanging one amino acid with another having similar properties, may be preferable.

Generation of Transgenic Cells and Plants

The present invention also relates to host cells and organisms which are transformed with nucleic acids corresponding to the tolerance, improved tolerance, or susceptibility/sensitivity markers, traits, or QTLs identified herein. For example, such nucleic acids include chromosome intervals (e.g., genomic fragments), ORFs, and/or cDNAs that encode a tolerance or improved tolerance trait. Additionally, production of polypeptides that provide tolerance or improved tolerance by recombinant techniques are provided.

General texts which describe molecular biological techniques for the cloning and manipulation of nucleic acids and production of encoded polypeptides include Berger and Kimmel, Guide to Molecular Cloning Techniques, Methods in Enzymology volume 152 Academic Press, Inc., San Diego, Calif. (Berger); Sambrook et al., Molecular Cloning—A Laboratory Manual (3rd Ed.), Vol. 1-3, Cold Spring Harbor Laboratory, Cold Spring Harbor, N.Y., 2001 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 2004 or later) ("Ausubel")). These texts describe mutagenesis, the use of vectors, promoters and many other relevant topics related to, e.g., the generation of clones that comprise nucleic acids of interest, e.g., marker loci, marker probes, QTL that segregate with marker loci, etc.

Host cells are genetically engineered (e.g., transduced, transfected, transformed, etc.) with the vectors (e.g., vectors, such as expression vectors which comprise an ORF derived from or related to a tolerance QTL) which can be, for example, a cloning vector, a shuttle vector, or an expression vector. Such vectors are, for example, in the form of a plasmid, a phagemid, an *agrobacterium*, a virus, a naked polynucleotide (linear or circular), or a conjugated polynucleotide. Vectors can be introduced into bacteria, especially for the purpose of propagation and expansion. The vectors are also introduced into plant tissues, cultured plant cells, or plant protoplasts by a variety of standard methods known in the art, including but not limited to electroporation (From et al. (1985) Proc. Natl. Acad. Sci. USA 82; 5824), infection by viral vectors such as cauliflower mosaic virus (CaMV) (Hohn et al. (1982) Molecular Biology of Plant Tumors (Academic Press, New York, pp. 549-560; Howell U.S. Pat. No. 4,407,956), high velocity ballistic penetration by small particles with the nucleic acid either within the matrix of small beads or particles or on the surface (Klein et al. (1987) Nature 327; 70), use of pollen as vector (WO 85/01856), or use of *Agrobacterium tumefaciens* or *A. rhizogenes* carrying a T-DNA plasmid in which DNA fragments are cloned. The T-DNA plasmid is transmitted to plant cells upon infection by *Agrobacterium tumefaciens*, and a portion is stably integrated into the plant genome (Horsch et al. (1984) Science 233:496; Fraley et al. (1983) Proc. Natl. Acad. Sci. USA 80:4803). Additional details regarding nucleic acid introduction methods are found in Sambrook, Berger and Ausubel. The method of introducing a nucleic acid into a host cell is not critical, and therefore should not be limited to any particular method for introducing exogenous genetic material into a host cell. Thus, any suitable method that provides for effective introduction of a nucleic acid into a cell or protoplast can be employed.

The engineered host cells can be cultured in conventional nutrient media modified as appropriate for such activities as, for example, activating promoters or selecting transformants. These cells can optionally be cultured into transgenic plants. In addition to Sambrook, Berger and Ausubel, Plant regeneration from cultured protoplasts is described in Evans et al. (1983) "Protoplast Isolation and Culture," Handbook of Plant Cell Cultures 1, 124-176 (MacMillan Publishing Co., New York; Davey (1983) "Recent Developments in the Culture and Regeneration of Plant Protoplasts," Protoplasts, pp. 12-29, (Birkhauser, Basel); Dale (1983) "Protoplast Culture and Plant Regeneration of Cereals and Other Recalcitrant Crops," Protoplasts pp. 31-41, (Birkhauser, Basel); Binding (1985) "Regeneration of Plants," Plant Protoplasts, pp. 21-73, (CRC Press, Boca Raton, Fla.). Additional details regarding plant cell culture and regeneration include Payne et al. (1992) Plant Cell and Tissue Culture in Liquid Systems John Wiley & Sons, Inc. New York, N.Y.; Gamborg and Phillips (eds) (1995) Plant Cell, Tissue and Organ Culture; Fundamental Methods Springer Lab Manual, Springer-Verlag (Berlin Heidelberg N.Y.) and Plant Molecular Biology (1993) R. R. D. Croy, Ed. Bios Scientific Publishers, Oxford, U.K. ISBN 0 12 198370 6. Cell culture media in general are also set forth in Atlas and Parks (eds), The Handbook of Microbiological Media (1993) CRC Press, Boca Raton, Fla. Additional information for cell culture is found in available commercial literature such as the Life Science Research Cell Culture Catalogue (1998) from Sigma-Aldrich, Inc (St Louis, Mo.) ("Sigma-LSRCCC") and the Plant Culture Catalogue and supplement (e.g., 1997 or later), also from Sigma-Aldrich, Inc (St Louis, Mo.) ("Sigma-PCCS").

The production of transgenic organisms is provided, which may be bacteria, yeast, fungi, animals or plants, transduced with the nucleic acids (e.g., nucleic acids comprising the marker loci and/or QTL noted herein). A thorough discussion of techniques relevant to bacteria, unicellular eukaryotes, and cell culture is found in references enumerated herein. Several well-known methods of introducing target nucleic acids into bacterial cells are available, any of which may be used. These include: fusion of the recipient cells with bacterial protoplasts containing the DNA, treatment of the cells with liposomes containing the DNA, electroporation, microinjection, cell fusions, projectile bombardment (biolistics), carbon fiber delivery, and infection with viral vectors (discussed further, below). Bacterial cells can be used to amplify the number of plasmids containing DNA constructs. The bacteria are grown to log phase and the plasmids within the bacteria can be isolated by a variety of methods known in the art (see, for instance, Sambrook). In addition, a plethora of kits are commercially available for the purification of plasmids from bacteria. For their proper use, follow the manufacturer's instructions (see, for example, EasyPrep™, FlexiPrep™, both from Pharmacia Biotech; StrataClean™, from Stratagene; and, QIAprep™ from Qiagen). The isolated and purified plasmids are then further manipulated to produce other plasmids, used to transfect plant cells or incorporated into *Agrobacterium tumefaciens* related vectors to infect plants. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors), and selection markers for both prokaryotic and eukaryotic systems. Vectors are suitable for replication and integration in prokaryotes, eukaryotes, or both. See, Giliman & Smith (1979) Gene 8:81; Roberts et al. (1987) Nature 328:731; Schneider et al. (1995) Protein Expr. Purif. 6435:10; Ausubel, Sambrook, Berger (all infra). A catalogue of bacteria and bacteriophages useful for cloning are well known in the art, e.g., The ATCC Catalogue of Bacteria and Bacteriophage (1992) Gherna et al. (eds), published by the ATCC.

Polynucleotide Constructs:

In specific embodiments, one or more of the herbicide-tolerant polynucleotides employed in the methods and compositions can be provided in an expression cassette for expression in the plant or other organism of interest. The cassette will include 5' and 3' regulatory sequences operably linked to an herbicide-tolerance polynucleotide. "Operably linked" is intended to mean a functional linkage between two or more elements. For example, an operable linkage between a polynucleotide of interest and a regulatory sequence (e.g., a promoter) is functional link that allows for expression of the polynucleotide of interest. Operably linked elements may be contiguous or non-contiguous. When used to refer to the joining of two protein coding regions, by "operably linked" is intended that the coding regions are in the same reading frame. When used to refer to the effect of an enhancer, "operably linked" indicates that the enhancer increases the expression of a particular polynucleotide or polynucleotides of interest. Where the polynucleotide or polynucleotides of interest encode a polypeptide, the encoded polypeptide is produced at a higher level.

The cassette may additionally contain at least one additional gene to be co-transformed into the organism. Alternatively, the additional gene(s) can be provided on multiple expression cassettes. Such an expression cassette is provided with a plurality of restriction sites and/or recombination sites for insertion of the herbicide-tolerance polynucleotide to be under the transcriptional regulation of the regulatory regions. The expression cassette may additionally contain other genes, including other selectable marker genes. Where a cassette contains more than one polynucleotide, the polynucleotides in the cassette may be transcribed in the same direction or in different directions (also called "divergent" transcription).

An expression cassette comprising an herbicide-tolerance polynucleotide will include, in the 5'-3' direction of transcription, a transcriptional and translational initiation region (i.e., a promoter), an herbicide-tolerance polynucleotide, and a transcriptional and translational termination region (i.e., termination region) functional in plants or the other organism of interest. Accordingly, plants having such expression cassettes are also provided. The regulatory regions (i.e., promoters, transcriptional regulatory regions, and translational termination regions) and/or the herbicide-tolerance polynucleotide may be native (i.e., analogous) to the host cell or to each other. Alternatively, the regulatory regions and/or the herbicide-tolerance polynucleotide may be heterologous to the host cell or to each other.

While it may be optimal to express polynucleotides using heterologous promoters, native promoter sequences may be used. Such constructs can change expression levels and/or expression patterns of the encoded polypeptide in the plant or plant cell. Expression levels and/or expression patterns of the encoded polypeptide may also be changed as a result of an additional regulatory element that is part of the construct, such as, for example, an enhancer. Thus, the phenotype of the plant or cell can be altered even though a native promoter is used.

The termination region may be native with the transcriptional initiation region, may be native with the operably linked herbicide-tolerance polynucleotide of interest, may be native with the plant host, or may be derived from another source (i.e., foreign or heterologous) to the promoter, the herbicide-tolerance polynucleotide of interest, the plant host, or any combination thereof. Convenient termination regions are available from the Ti-plasmid of *A. tumefaciens*, such as the octopine synthase and nopaline synthase termination regions, or can be obtained from plant genes such as the *Solanum tuberosum* proteinase inhibitor II gene. See Guerineau et al. (1991) Mol. Gen. Genet. 262: 141-144; Proudfoot (1991) Cell 64: 671-674; Sanfacon et al. (1991) Genes Dev. 5: 141-149; Mogen et al. (1990) Plant Cell 2: 1261-1272; Munroe et al. (1990) Gene 91: 151-158; Ballas et al. (1989) Nucleic Acids Res. 17: 7891-7903; and Joshi et al. (1987) Nucleic Acids Res. 15: 9627-9639.

A number of promoters can be used, including the native promoter of the polynucleotide sequence of interest. The promoters can be selected based on the desired outcome. The polynucleotides of interest can be combined with constitutive, tissue-preferred, or other promoters for expression in plants.

Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) Nature 313:810-812); rice actin (McElroy et al. (1990) Plant Cell 2:163-171); the maize actin promoter; the ubiquitin promoter (see, e.g., Christensen et al. (1989) Plant Mol. Biol. 12:619-632; Christensen et al. (1992) Plant Mol. Biol. 18:675-689; Callis et al. (1995) Genetics 139:921-39); pEMU (Last et al. (1991) Theor. Appl. Genet. 81:581-588); MAS (Velten et al. (1984) EMBO J. 3: 2723-2730); ALS promoter (U.S. Pat. No. 5,659,026), and the like. Other constitutive promoters include, for example, those described in U.S. Pat. Nos. 5,608,149; 5,608,144; 5,604,121; 5,569,597; 5,466,785; 5,399,680; 5,268,463; 5,608,142; and 6,177,611. Some promoters show improved expression when they are used in conjunction with a native 5' untranslated region and/or other elements such as, for example, an intron. For example, the maize ubiquitin promoter is often placed upstream of a polynucleotide of interest along with at least a portion of the 5' untranslated region of the ubiquitin gene, including the first intron of the maize ubiquitin gene.

Chemical-regulated promoters can be used to modulate the expression of a gene in a plant through the application of an exogenous chemical regulator. Depending upon the objective, the promoter may be a chemical-inducible promoter for which application of the chemical induces gene expression or the promoter may be a chemical-repressible promoter for which application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, e.g., the glucocorticoid-inducible promoter in Schena et al. (1991) Proc. Natl. Acad. Sci. USA 88:10421-10425 and McNellis et al. (1998) Plant J. 14:247-257) and tetracycline-inducible and tetracycline-repressible promoters (see, e.g., Gatz et al. (1991) Mol. Gen. Genet. 227:229-237, and U.S. Pat. Nos. 5,814,618 and 5,789,156), herein incorporated by reference.

Tissue-preferred promoters can be utilized to target enhanced herbicide-tolerance polypeptide expression within a particular plant tissue. Tissue-preferred promoters include Yamamoto et al. (1997) Plant J. 12:255-265; Kawamata et al. (1997) Plant Cell Physiol. 38:792-803; Hansen et al. (1997) Mol. Gen Genet. 254:337-343; Russell et al. (1997) Transgenic Res. 6:157-168; Rinehart et al. (1996) Plant Physiol. 112:1331-1341; Van Camp et al. (1996) Plant Physiol. 112:525-535; Canevascini et al. (1996) Plant Physiol. 112:513-524; Yamamoto et al. (1994) Plant Cell Physiol. 35:773-778; Lam (1994) Results Probl. Cell Differ. 20:181-196; Orozco et al. (1993) Plant Mol Biol. 23:1129-1138; Matsuoka et al. (1993) Proc Natl. Acad. Sci. USA 90:9586-9590; and Guevara-Garcia et al. (1993) Plant J. 4:495-505. Such promoters can be modified, if necessary, for weak expression.

Leaf-preferred promoters are known in the art. See, e.g., Yamamoto et al. (1997) Plant J. 12:255-265; Kwon et al. (1994) Plant Physiol. 105:357-67; Yamamoto et al. (1994) Plant Cell Physiol. 35:773-778; Gotor et al. (1993) Plant J. 3:509-18; Orozco et al. (1993) Plant Mol. Biol. 23:1129-1138; and Matsuoka et al. (1993) Proc. Natl. Acad. Sci. USA 90(20):9586-9590.

Root-preferred promoters are known and can be selected from the many available from the literature or isolated de novo from various compatible species. See, e.g., Hire et al. (1992) Plant Mol. Biol. 20:207-218 (soybean root-specific glutamine synthetase gene); Keller and Baumgartner (1991) Plant Cell 3:1051-1061 (root-specific control element in the GRP 1.8 gene of French bean); Sanger et al. (1990) Plant Mol. Biol. 14(3):433-443 (root-specific promoter of the mannopine synthase (MAS) gene of *Agrobacterium tumefaciens*); and Miao et al. (1991) Plant Cell 3:11-22 (full-length cDNA clone encoding cytosolic glutamine synthetase (GS), which is expressed in roots and root nodules of soybean). See also Bogusz et al. (1990) Plant Cell 2(7): 633-641, where two root-specific promoters are described. Leach and Aoyagi (1991) describe their analysis of the promoters of the highly expressed rolC and rolD root-inducing genes of *Agrobacterium rhizogenes* (see Plant Science (Limerick) 79:69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see EMBO J. 8:343-350). The TR1' gene, fused to nptII (neomycin phosphotransferase II) showed similar characteristics. Additional root-preferred promoters include the VfENOD-GRP3 gene promoter (Kuster et al. (1995) Plant Mol. Biol. 29:759-772); and rolB promoter (Capana et al. (1994) Plant Mol. Biol. 25:681-691. See also U.S. Pat. Nos. 5,837,876; 5,750,386; 5,633,363; 5,459,252; 5,401,836; 5,110,732; and 5,023,179.

Seed-preferred promoters include both seed-specific promoters (those promoters active during seed development such as promoters of seed storage proteins) as well as seed-germinating promoters (those promoters active during seed germination). See Thompson et al. (1989) BioEssays 10:108, herein incorporated by reference. Such seed-preferred promoters include, but are not limited to, Cim1 (cytokinin-induced message); cZ19B1 (maize 19 kDa zein); milps (myo-inositol-1-phosphate synthase) (see WO 00/11177 and U.S. Pat. No. 6,225,529; herein incorporated by reference). Gamma-zein is an endosperm-specific promoter. Globulin 1 (Glb-1) is a representative embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, gamma-zein, waxy, shrunken 1, shrunken 2, globulin 1, etc. See also WO 00/12733, where seed-preferred promoters from end1 and end2 genes are disclosed; herein incorporated by reference.

Additional promoters of interest include the SCP1 promoter (U.S. Pat. No. 6,072,050), the HB2 promoter (U.S. Pat. No. 6,177,611) and the SAMS promoter (US20030226166 and SEQ ID NO: 87 and biologically active variants and fragments thereof); each of which is herein incorporated by reference. In addition, as discussed elsewhere herein, various enhancers can be used with these promoters including, for example, the ubiquitin intron (i.e., the maize ubiquitin intron 1 (see, e.g., NCBI sequence S94464), the omega enhancer or the omega prime enhancer (Gallie et al. (1989) Molecular Biology of RNA ed. Cech (Liss, N.Y.) 237-256 and Gallie et al. Gene (1987) 60:217-25), or the 35S enhancer; each of which is incorporated by reference.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as beta-galactosidase and fluorescent proteins such as green fluorescent protein (GFP) (Su et al. (2004) Biotechnol Bioeng 85:610-9 and Fetter et al. (2004) Plant Cell 16:215-28), cyan florescent protein (CYP) (Bolte et al. (2004) J. Cell Science 117:943-54 and Kato et al. (2002) Plant Physiol 129:913-42), and yellow fluorescent protein (PhiYFP from Evrogen, see, Bolte et al. (2004) J. Cell Science 117:943-54). For additional selectable markers, see generally Yarranton (1992) Curr. Opin. Biotech. 3:506-511; Christopherson et al. (1992) Proc. Natl. Acad. Sci. USA 89:6314-6318; Yao et al. (1992) Cell 71:63-72; Reznikoff (1992) Mol. Microbiol. 6:2419-2422; Barkley et al. (1980) in The Operon, pp. 177-220; Hu et al. (1987) Cell 48:555-566; Brown et al. (1987) Cell 49:603-612; Figge et al. (1988) Cell 52:713-722; Deuschle et al. (1989) Proc. Natl. Acad. Aci. USA 86:5400-5404; Fuerst et al. (1989) Proc. Natl. Acad. Sci. USA 86:2549-2553; Deuschle et al. (1990) Science 248:480-483; Gossen (1993) Ph.D. Thesis, University of Heidelberg; Reines et al. (1993) Proc. Natl. Acad. Sci. USA 90:1917-1921; Labow et al. (1990) Mol. Cell. Biol. 10:3343-3356; Zambretti et al. (1992) Proc. Natl. Acad. Sci. USA 89:3952-3956; Bairn et al. (1991) Proc. Natl. Acad. Sci. USA 88:5072-5076; Wyborski et al. (1991) Nucleic Acids Res. 19:4647-4653; Hillenand-Wissman (1989) Topics Mol. Struc. Biol. 10:143-162; Degenkolb et al. (1991) Antimicrob. Agents Chemother. 35:1591-1595; Kleinschnidt et al. (1988) Biochemistry 27:1094-1104; Bonin (1993) Ph.D. Thesis, University of Heidelberg; Gossen et al. (1992) Proc. Natl. Acad. Sci. USA 89:5547-5551; Oliva et al. (1992) Antimicrob. Agents Chemother. 36:913-919; Hlavka et al. (1985) Handbook of Experimental Pharmacology, Vol. 78 (Springer-Verlag, Berlin); Gill et al. (1988) Nature 334:721-724. Such disclosures are herein incorporated by reference. The above list of selectable marker genes is not meant to be limiting. Any selectable marker gene can be used, including the GAT gene and/or HRA gene.

Methods are known in the art of increasing the expression level of a polypeptide in a plant or plant cell, for example, by inserting into the polypeptide coding sequence one or two G/C-rich codons (such as GCG or GCT) immediately adjacent to and downstream of the initiating methionine ATG codon. Where appropriate, the polynucleotides may be modified for increased expression in the transformed plant. That is, the polynucleotides can be synthesized substituting in the polypeptide coding sequence one or more codons which are less frequently utilized in plants for codons encoding the same amino acid(s) which are more frequently utilized in plants, and introducing the modified coding sequence into a plant or plant cell and expressing the modified coding sequence. See, e.g., Campbell and Gowri (1990) Plant Physiol. 92:1-11 for a discussion of host-preferred codon usage. Methods are available in the art for synthesizing plant-preferred genes. See, e.g., U.S. Pat. Nos. 5,380,831, and 5,436,391, and Murray et al. (1989) Nucleic Acids Res. 17:477-498, herein incorporated by reference. Embodiments comprising such modifications are also a feature disclosed.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures. Enhancers such as the CaMV 35S enhancer may also be used (see, e.g., Benfey et al. (1990) EMBO J. 9:1685-96), or other enhancers may be used. For example, the sequence set forth in SEQ ID NO: 1, 72, 79, 84, 85, 88, or 89 or a biologically active variant or fragment thereof can be used. See also published application US2007/061917. As used herein, an enhancer, when operably linked to an appropriate promoter, will modulate the level of transcription of an operably linked polynucleotide of interest. Biologically active fragments and variants of the enhancer domain may retain the biological activity of modulating (increase or decrease) the level of transcription when operably linked to an appropriate promoter. Generally, variants of a particular polynucleotides will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to another polynucleotides as determined by sequence alignment programs and parameters. Variants of a particular polynucleotides also include those encoding a polypeptide having at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to a reference polypeptide as determined by sequence alignment programs and parameters. Polypeptide variants include those encoded by variant polynucleotides, and those having at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to a reference polypeptide as determined by sequence alignment programs and parameters.

It is also recognized that the level and/or activity of a polypeptide of interest may be modulated by employing a polynucleotide that is not capable of directing, in a transformed plant, the expression of a protein or an RNA. For example, the polynucleotides may be used to design polynucleotide constructs that can be employed in methods for altering or mutating a genomic nucleotide sequence in an organism. Such polynucleotide constructs include, but are not limited to, RNA:DNA vectors, RNA:DNA mutational vectors, RNA:DNA repair vectors, mixed-duplex oligonucleotides, self-complementary RNA:DNA oligonucleotides, and recombinogenic oligonucleobases. Such nucleotide constructs and methods of use are known in the art. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al. (1999) Proc. Natl. Acad. Sci. USA 96: 8774-8778; herein incorporated by reference.

The expression cassette may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) Proc. Natl. Acad. Sci. USA 86: 6126-6130); potyvirus leaders, for example, TEV leader (Tobacco Etch Virus) (Gallie et al. (1995) Gene 165(2): 233-238), MDMV leader (Maize Dwarf Mosaic Virus) (Kong et al. (1988) Arch Virol 143:1791-1799), and human immunoglobulin heavy-chain binding protein (BiP) (Macejak et al. (1991) Nature 353: 90-94); untranslated leader from the coat protein mRNA of alfalfa mosaic virus (AMV RNA 4) (Jobling et al. (1987) Nature 325: 622-625); tobacco mosaic virus leader (TMV) (Gallie et al. (1989) in Molecular Biology of RNA, ed. Cech (Liss, N.Y.), pp. 237-256); and maize chlorotic mottle virus leader (MCMV) (Lommel et al. (1991) Virology 81: 382-385). See also, Della-Cioppa et al. (1987) Plant Physiol. 84: 965-968.

In preparing the expression cassette, the various polynucleotide fragments may be manipulated, so as to provide for sequences to be in the proper orientation and, as appropriate, in the proper reading frame. Toward this end, adapters or linkers may be employed to join the fragments or other manipulations may be involved to provide for convenient restriction sites, removal of superfluous material such as the removal of restriction sites, or the like. For this purpose, in vitro mutagenesis, primer repair, restriction, annealing, resubstitutions, e.g., transitions and transversions, may be involved. Standard recombinant DNA and molecular cloning techniques used herein are well known in the art and are described more fully, for example, in Sambrook et al. (1989) Molecular Cloning: A Laboratory Manual (Cold Spring Harbor Laboratory Press, Cold Spring Harbor) (also known as "Maniatis").

In some embodiments, the polynucleotide of interest is targeted to the chloroplast for expression. In this manner, where the polynucleotide of interest is not directly inserted into the chloroplast, the expression cassette will additionally contain a nucleic acid encoding a transit peptide to direct the gene product of interest to the chloroplasts. Such transit peptides are known in the art. See, e.g., Von Heijne et al. (1991) Plant Mol. Biol. Rep. 9: 104-126; Clark et al. (1989) J. Biol. Chem. 264: 17544-17550; Della-Cioppa et al. (1987) Plant Physiol. 84: 965-968; Romer et al. (1993) Biochem. Biophys. Res. Comm. 196: 1414-1421; and Shah et al. (1986) Science 233: 478-481.

Chloroplast targeting sequences are known in the art and include the chloroplast small subunit of ribulose-1,5-bisphosphate carboxylase (Rubisco) (de Castro Silva Filho et al. (1996) Plant Mol. Biol. 30: 769-780; Schnell et al. (1991) J. Biol. Chem. 266(5): 3335-3342); 5-(enolpyruvyl)shikimate-3-phosphate synthase (EPSPS) (Archer et al. (1990) J. Bioenerg Biomemb. 22(6): 789-810); tryptophan synthase (Zhao et al. (1995) J. Biol. Chem. 270(11): 6081-6087); plastocyanin (Lawrence et al. (1997) J. Biol. Chem. 272(33): 20357-20363); chorismate synthase (Schmidt et al. (1993) J. Biol. Chem. 268(36): 27447-27457); and the light harvesting chlorophyll a/b binding protein (LHBP) (Lamppa et al. (1988) J. Biol. Chem. 263: 14996-14999). See also Von Heijne et al. (1991) Plant Mol. Biol. Rep. 9: 104-126; Clark et al. (1989) J. Biol. Chem. 264: 17544-17550; Della-Cioppa et al. (1987) Plant Physiol. 84: 965-968; Romer et al. (1993) Biochem. Biophys. Res. Comm. 196: 1414-1421; and Shah et al. (1986) Science 233: 478-481.

Methods for transformation of chloroplasts are known in the art. See, e.g., Svab et al. (1990) Proc. Natl. Acad. Sci. USA 87: 8526-8530; Svab and Maliga (1993) Proc. Natl. Acad. Sci. USA 90: 913-917; Svab and Maliga (1993) EMBO J. 12: 601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) Proc. Natl. Acad. Sci. USA 91: 7301-7305.

The polynucleotides of interest to be targeted to the chloroplast may be optimized for expression in the chloroplast to account for differences in codon usage between the plant nucleus and this organelle. In this manner, the polynucleotide of interest may be synthesized using chloroplast-preferred codons. See, e.g., U.S. Pat. No. 5,380,831, herein incorporated by reference.

Introducing Nucleic Acids into Plants:

Methods for the production of transgenic plants comprising the cloned nucleic acids, e.g., isolated ORFs and cDNAs encoding tolerance genes, are provided. Techniques for transforming plant cells with nucleic acids are widely available and can be readily adapted. In addition to the Berger, Ausubel, and Sambrook references, useful general references for plant cell cloning, culture and regeneration include Jones (ed) (1995) Plant Gene Transfer and Expression Protocols—Methods in Molecular Biology, Volume 49 Humana Press Towata N.J.; Payne et al. (1992) Plant Cell and Tissue Culture in Liquid Systems John Wiley & Sons, Inc. New York, N.Y. (Payne); and Gamborg and Phillips (eds) (1995) Plant Cell, Tissue and Organ Culture; Fundamental Methods Springer Lab Manual, Springer-Verlag (Berlin Heidelberg N.Y.) (Gamborg). A variety of cell culture media are described in Atlas and Parks (eds) The Handbook of Microbiological Media (1993) CRC Press, Boca Raton, Fla. (Atlas). Additional information for plant cell culture is found in available commercial literature such as the Life Science Research Cell Culture Catalogue (1998) from Sigma-Aldrich, Inc (St Louis, Mo.) (Sigma-LSRCCC) and, e.g., the Plant Culture Catalogue and supplement (1997) also from Sigma-Aldrich, Inc (St Louis, Mo.) (Sigma-PCCS). Additional details regarding plant cell culture are found in Croy, (ed.) (1993) Plant Molecular Biology, Bios Scientific Publishers, Oxford, U.K.

The nucleic acid constructs, e.g., DNA molecules plasmids, cosmids, artificial chromosomes, DNA, and RNA polynucleotides, are introduced into plant cells, either in culture or in the organs of a plant by a variety of conventional techniques. Where the sequence is expressed, the sequence is optionally combined with transcriptional and translational initiation regulatory sequences which direct the transcription or translation of the sequence from the exogenous DNA in the intended tissues of the transformed plant.

Isolated nucleic acids can be introduced into plants according to any of a variety of techniques known in the art. Techniques for transforming a wide variety of higher plant species are also well known and described in widely available technical, scientific, and patent literature. See, e.g., Weising et al. (1988) Ann. Rev. Genet. 22:421-477.

Such methods for introducing polynucleotide or polypeptides into plants include stable transformation methods, transient transformation methods, virus-mediated methods, and breeding. "Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant.

The DNA constructs, for example DNA fragments, plasmids, phagemids, cosmids, phage, naked or variously conjugated-DNA polynucleotides, (e.g., polylysine-conjugated DNA, peptide-conjugated DNA, liposome-conjugated DNA, etc.), or artificial chromosomes, can be introduced directly into the genomic DNA of the plant cell using techniques such as electroporation and microinjection of plant cell protoplasts, or the DNA constructs can be introduced directly to plant cells using ballistic methods, such as DNA particle bombardment.

Transformation protocols as well as protocols for introducing polypeptides or polynucleotide sequences into plants may vary depending on the type of plant or plant cell (i.e., monocot or dicot) targeted for transformation. Suitable methods of introducing polypeptides and polynucleotides into plant cells include microinjection (Crossway et al. (1986) Biotechniques 4:320-334), electroporation (Riggs et al. (1986) Proc. Natl. Acad. Sci. USA 83: 5602-5606, Agrobacterium-mediated transformation (U.S. Pat. Nos. 5,563,055 and 5,981,840), direct gene transfer (Paszkowski et al. (1984) EMBO J. 3: 2717-2722), and ballistic particle acceleration (see, for example, U.S. Pat. Nos. 4,945,050; 5,879,918; 5,886,244; and, 5,932,782; Tomes et al. (1995) in Plant Cell, Tissue, and Organ Culture: Fundamental Methods, ed. Gamborg and Phillips (Springer-Verlag, Berlin); McCabe et al. (1988) Biotechnology 6: 923-926); and Lec1 transformation (WO 00/28058). Also see Weissinger et al. (1988) Ann. Rev. Genet. 22: 421-477; Sanford et al. (1987) Particulate Science and Technology 5: 27-37 (onion); Christou et al. (1988) Plant Physiol. 87: 671-674 (soybean); McCabe et al. (1988) Bio/Technology 6: 923-926 (soybean); Finer and McMullen (1991) In Vitro Cell Dev. Biol. 27P: 175-182 (soybean); Singh et al. (1998) Theor. Appl. Genet. 96:319-324 (soybean); Datta et al. (1990) Biotechnology 8: 736-740 (rice); Klein et al. (1988) Proc. Natl. Acad. Sci. USA 85:4305-4309 (maize); Klein et al. (1988) Biotechnology 6:559-563 (maize); U.S. Pat. Nos. 5,240,855; 5,322, 783; and, 5,324,646; Klein et al. (1988) Plant Physiol. 91: 440-444 (maize); Fromm et al. (1990) Biotechnology 8: 833-839 (maize); protocols published electronically by "IP.com" under the permanent publication identifiers IPCOM000033402D, IPCOM000033402D, and IPCOM000033402D and available at the "IP.com" website (cotton); Hooykaas-Van Slogteren et al. (1984) Nature (London) 311: 763-764; U.S. Pat. No. 5,736,369 (cereals); Bytebier et al. (1987) Proc. Natl. Acad. Sci. USA 84: 5345-5349 (Liliaceae); De Wet et al. (1985) in The Experimental Manipulation of Ovule Tissues, ed. Chapman et al. (Longman, N.Y.), pp. 197-209 (pollen); Kaeppler et al. (1990) Plant Cell Reports 9: 415-418 and Kaeppler et al. (1992) Theor. Appl. Genet. 84: 560-566 (whisker-mediated transformation); D'Halluin et al. (1992) Plant Cell 4: 1495-1505 (electroporation); Li et al. (1993) Plant Cell Reports 12: 250-255 and Christou and Ford (1995) Annals of Botany 75: 407-413 (rice); Osjoda et al. (1996) Nature Biotechnology 14: 745-750 (maize via *Agrobacterium tumefaciens*); all of which are herein incorporated by reference.

Microinjection techniques for injecting plant, e.g., cells, embryos, callus, and protoplasts, are known in the art and well described in the scientific and patent literature. For example, a number of methods are described in Jones (ed) (1995) Plant Gene Transfer and Expression Protocols—Methods in Molecular Biology, Volume 49 Humana Press, Towata, N.J., as well as in the other references noted herein and available in the literature.

For example, the introduction of DNA constructs using polyethylene glycol precipitation is described in Paszkowski et al., EMBO J. 3:2717 (1984). Electroporation techniques are described in Fromm et al., Proc. Natl. Acad. Sci. USA 82:5824 (1985). Ballistic transformation techniques are described in Klein et al., Nature 327:70-73 (1987). Additional details are found in Jones (1995) and Gamborg and Phillips (1995), supra, and in U.S. Pat. No. 5,990,387.

Alternatively, *Agrobacterium*-mediated transformation is employed to generate transgenic plants. *Agrobacterium*-mediated transformation techniques, including disarming and use of binary vectors, are also well described in the scientific literature. See, e.g., Horsch, et al. (1984) Science 233:496; and Fraley et al. (1984) Proc. Natl. Acad. Sci. USA 80:4803 and recently reviewed in Hansen and Chilton (1998) Current Topics in Microbiology 240:22 and Das (1998) Subcellular Biochemistry 29: Plant Microbe Interactions, pp 343-363.

DNA constructs are optionally combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616. Although *Agrobacterium* is useful primarily in dicots, certain monocots can be transformed by *Agrobacterium*. For instance, *Agrobacterium* transformation of maize is described in U.S. Pat. No. 5,550,318.

Other methods of transfection or transformation include (1) *Agrobacterium rhizogenes*-mediated transformation (see, e.g., Lichtenstein and Fuller (1987) In: Genetic Engineering, vol. 6, P W J Rigby, Ed., London, Academic Press; and Lichtenstein; C. P., and Draper (1985) In: DNA Cloning, Vol. II, D. M. Glover, Ed., Oxford, IRI Press; WO 88/02405, published Apr. 7, 1988, describes the use of *A. rhizogenes* strain A4 and its Ri plasmid along with *A. tumefaciens* vectors pARC8 or pARC16 (2) liposome-mediated DNA uptake (see, e.g., Freeman et al. (1984) Plant Cell Physiol. 25:1353), (3) the vortexing method (see, e.g., Kindle (1990) Proc. Natl. Acad. Sci., (USA) 87:1228.

DNA can also be introduced into plants by direct DNA transfer into pollen as described by Zhou et al. (1983) Methods in Enzymology, 101:433; D. Hess (1987) Intern Rev. Cytol. 107:367; Luo et al. (1988) Plant Mol. Biol. Reporter 6:165. Expression of polypeptide coding genes can be obtained by injection of the DNA into reproductive organs of a plant as described by Pena et al. (1987) Nature 325:274. DNA can also be injected directly into the cells of immature embryos and the desiccated embryos rehydrated as described by Neuhaus et al. (1987) Theor. Appl. Genet. 75:30; and Benbrook et al. (1986) in Proceedings Bio Expo Butterworth, Stoneham, Mass., pp. 27-54. A variety of plant viruses that can be employed as vectors are known in the art and include cauliflower mosaic virus (CaMV), geminivirus, brome mosaic virus, and tobacco mosaic virus.

Methods are known in the art for the targeted insertion of a polynucleotide at a specific location in the plant genome. In one embodiment, the insertion of the polynucleotide at a desired genomic location is achieved using a site-specific recombination system. See, e.g., WO99/25821, WO99/25854, WO99/25840, WO99/25855, and WO99/25853, all of which are herein incorporated by reference. Briefly, a polynucleotide can be contained in transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

Generation/Regeneration of Transgenic Plants:

Transformed plant cells which are derived by any of the above transformation techniques can be cultured to regenerate a whole plant that possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Payne et al. (1992) Plant Cell and Tissue Culture in Liquid Systems John Wiley & Sons, Inc. New York, N.Y.; Gamborg and Phillips (eds) (1995) Plant Cell, Tissue and Organ Culture; Fundamental Methods Springer Lab Manual, Springer-Verlag (Berlin Heidelberg N.Y.); Evans et al. (1983) Protoplasts Isolation and Culture, Handbook of Plant Cell Culture pp. 124-176, Macmillian Publishing Company, New York; and Binding (1985) Regeneration of Plants, Plant Protoplasts pp. 21-73, CRC Press, Boca Raton. Regeneration can also be obtained from plant callus, explants, somatic embryos (Dandekar et al. (1989) J. Tissue Cult. Meth. 12:145; McGranahan, et al. (1990) Plant Cell Rep. 8:512) organs, or parts thereof. Such regeneration techniques are described generally in Klee et al. (1987), Ann. Rev. of Plant Phys. 38:467-486. Additional details are found in Payne (1992) and Jones (1995), both supra, and Weissbach and Weissbach, eds. (1988) Methods for Plant Molecular Biology Academic Press, Inc., San Diego, Calif. This regeneration and growth process includes the steps of selection of transformant cells and shoots, rooting the transformant shoots and growth of the plantlets in soil. These methods are adapted to produce transgenic plants bearing QTLs and other genes isolated according to the methods.

In addition, the regeneration of plants containing the polynucleotides and introduced by *Agrobacterium* into cells of leaf explants can be achieved as described by Horsch et al. (1985) Science 227:1229-1231. In this procedure, transformants are grown in the presence of a selection agent and in a medium that induces the regeneration of shoots in the plant species being transformed as described by Fraley et al. (1983) Proc. Natl. Acad. Sci. (U.S.A.) 80:4803. This procedure typically produces shoots within two to four weeks and these transformant shoots are then transferred to an appropriate root-inducing medium containing the selective agent and an antibiotic to prevent bacterial growth. Transgenic plants may be fertile or sterile.

It is not intended that plant transformation and expression of polypeptides that provide herbicide tolerance be limited to soybean species. Indeed, it is contemplated that the polypeptides that provide tolerance in soybean can also provide a similar phenotype when transformed and expressed in other plants. Examples of plant genuses and species of interest include, but are not limited to, monocots and dicots such as corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats (*Avena*), barley (*Hordeum*), palm, legumes including beans and peas such as guar, locust bean, fenugreek, garden beans, cowpea, mungbean, lima bean, fava bean, lentils, chickpea, and castor, *Arabidopsis*, vegetables, ornamentals, grasses, conifers, crop and grain plants that provide seeds of interest, oil-seed plants, and other leguminous plants. Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

Promoters of bacterial origin that operate in plants include the octopine synthase promoter, the nopaline synthase promoter and other promoters derived from native Ti plasmids. See, Herrara-Estrella et al. (1983), Nature, 303:209. Viral promoters include the 35S and 19S RNA promoters of cauliflower mosaic virus. See, Odell et al. (1985) Nature, 313:810. Other plant promoters include Kunitz trypsin inhibitor promoter (KTI), SCP1, SUP, UCD3, the ribulose-1,3-bisphosphate carboxylase small subunit promoter and the phaseolin promoter. The promoter sequence from the E8 gene and other genes may also be used. The isolation and sequence of the E8 promoter is described in detail in Deikman and Fischer (1988) EMBO J. 7:3315. Many other promoters are in current use and can be coupled to an exogenous DNA sequence to direct expression of the nucleic acid.

If expression of a polypeptide from a cDNA is desired, a polyadenylation region at the 3'-end of the coding region is typically included. The polyadenylation region can be derived from the natural gene, from a variety of other plant genes, or from, e.g., T-DNA.

The vector comprising the sequences (e.g., promoters or coding regions) from genes encoding expression products and transgenes will typically include a nucleic acid subsequence, a marker gene which confers a selectable, or alternatively, a screenable, phenotype on plant cells. For example, the marker can encode biocide tolerance, particularly antibiotic tolerance, such as tolerance to kanamycin, G418, bleomycin, hygromycin, or herbicide tolerance, such as tolerance to chlorsulforon, or phosphinothricin (the active ingredient in the herbicides bialaphos or Basta). See, e.g., Padgette et al. (1996) In: Herbicide-Resistant Crops (Duke, ed.), pp 53-84, CRC Lewis Publishers, Boca Raton ("Padgette, 1996"). For example, crop selectivity to specific herbicides can be conferred by engineering genes into crops that encode appropriate herbicide metabolizing enzymes from other organisms, such as microbes. See Vasil (1996) In: Herbicide-Resistant Crops (Duke, ed.), pp 85-91, CRC Lewis Publishers, Boca Raton) ("Vasil", 1996).

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed. In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype. Parts obtained from the regenerated plant, such as flowers, seeds, leaves, branches, fruit, and the like are included, provided that these parts comprise cells comprising the isolated nucleic acid. Progeny and variants, and mutants of the regenerated plants are also included, provided that these parts comprise the introduced nucleic acid sequences.

Transgenic or introgressed plants expressing a polynucleotide can be screened for transmission of the nucleic acid by, for example, standard nucleic acid detection methods or by immunoblot protocols. Expression at the RNA level can be determined to identify and quantitate expression-positive plants. Standard techniques for RNA analysis can be employed and include RT-PCR amplification assays using oligonucleotide primers designed to amplify only heterologous or introgressed RNA templates and solution hybridization assays using marker or linked QTL specific probes. Plants can also be analyzed for protein expression, e.g., by Western immunoblot analysis using antibodies that recognize the encoded polypeptides. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

In one example a transgenic plant that is homozygous for the added heterologous nucleic acid; e.g., a transgenic plant that contains two added nucleic acid sequence copies, such as a gene at the same locus on each chromosome of a homologous chromosome pair, is provided. A homozygous transgenic plant can be obtained by sexually mating (self-fertilizing) a heterozygous transgenic plant that contains a single added heterologous nucleic acid, germinating some of the seed produced and analyzing the resulting plants produced for altered expression of a polynucleotide relative to a control plant (e.g., a native, non-transgenic plant). Backcrossing to a parental plant and out-crossing with a non-transgenic plant can be used to introgress the heterologous nucleic acid into a selected background (e.g., an elite or exotic soybean line).

Plants may be produced by any suitable method, including breeding. Plant breeding can be used to introduce desired characteristics (e.g., a stably incorporated transgene or a genetic variant or genetic alteration of interest) into a particular plant line of interest, and can be performed in any of several different ways. Pedigree breeding starts with the crossing of two genotypes, such as an elite line of interest and one other elite inbred line having one or more desirable characteristics (i.e., having stably incorporated a polynucleotide of interest, having a modulated activity and/or level of the polypeptide of interest, etc.) which complements the elite plant line of interest. If the two original parents do not provide all the desired characteristics, other sources can be included in the breeding population. In the pedigree method, superior plants are selfed and selected in successive filial generations. After a sufficient amount of inbreeding, successive filial generations will serve to increase seed of the developed inbred. In specific embodiments, the inbred line comprises homozygous alleles at about 95% or more of its loci. Various techniques known in the art can be used to facilitate and accelerate the breeding (e.g., backcrossing) process, including, for example, the use of a greenhouse or growth chamber with accelerated day/night cycles, the analysis of molecular markers to identify desirable progeny, and the like.

In addition to being used to create a backcross conversion, backcrossing can also be used in combination with pedigree breeding to modify an elite line of interest and a hybrid that is made using the modified elite line. As discussed previously, backcrossing can be used to transfer one or more specifically desirable traits from one line, the donor parent, to an inbred called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, an F1, such as a commercial hybrid, is created. This commercial hybrid may be backcrossed to one of its parent lines to create a BC1 or BC2. Progeny are selfed and selected so that the newly developed inbred has many of the attributes of the recurrent parent and yet several of the desired attributes of the non-recurrent parent. This approach leverages the value and strengths of the recurrent parent for use in new hybrids and breeding.

Therefore, a method of making a backcross conversion of an inbred line of interest comprising the steps of crossing a plant from the inbred line of interest with a donor plant comprising at least one mutant gene or transgene conferring a desired trait (e.g., herbicide tolerance), selecting an F1 progeny plant comprising the mutant gene or transgene conferring the desired trait, and backcrossing the selected F1 progeny plant to a plant of the inbred line of interest is provided. This method may further comprise the step of obtaining a molecular marker profile of the inbred line of interest and using the molecular marker profile to select for a progeny plant with the desired trait and the molecular marker profile of the inbred line of interest. In the same manner, this method may be used to produce an F1 hybrid seed by adding a final step of crossing the desired trait conversion of the inbred line of interest with a different plant to make F1 hybrid seed comprising a mutant gene or transgene conferring the desired trait.

Recurrent selection is a method used in a plant breeding program to improve a population of plants. The method entails individual plants cross pollinating with each other to form progeny. The progeny are grown and the superior progeny selected by any number of selection methods, which include individual plant, half-sib progeny, full-sib progeny, selfed progeny and topcrossing. The selected progeny are cross-pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain inbred lines to be used in hybrids or used as parents for a synthetic cultivar. A synthetic cultivar is the resultant progeny formed by the intercrossing of several selected inbreds.

Mass selection is a useful technique when used in conjunction with molecular marker enhanced selection. In mass selection seeds from individuals are selected based on phenotype and/or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Instead of self pollination, directed pollination could be used as part of the breeding program.

Mutation breeding is one of many methods that could be used to introduce new traits into an elite line. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation such as X-rays, gamma rays (e.g., cobalt 60 or cesium 137), neutrons, (product of nuclear fission of uranium 235 in an atomic reactor), Beta radiation (emitted from radioisotopes such as phosphorus 32 or carbon 14), or ultraviolet radiation (typically from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques, such as backcrossing. Details of mutation breeding can be found in "Principals of Cultivar Development" Fehr, 1993 Macmillan Publishing Company the disclosure of which is incorporated herein by reference. In addition, mutations created in other lines may be used to produce a backcross conversion of elite lines that comprises such mutations.

Methods of Modulating Expression:

In some embodiments, the activity and/or level of the polypeptide is modulated (i.e., increased or decreased). An increase in the level and/or activity of the polypeptide can be achieved by providing the polypeptide to the plant. As discussed elsewhere herein, many methods are known the art for providing a polypeptide to a plant including, but not limited to, direct introduction of the polypeptide into the plant, introducing into the plant (transiently or stably) a polynucleotide construct encoding a polypeptide having the desired activity.

Methods for Identifying Mesotrione or Isoxazole Tolerant or Susceptible Soybean Plants Experienced plant breeders can recognize tolerant soybean plants in the field, and can select the tolerant individuals or populations for breeding purposes or for propagation. In this context, the plant breeder recognizes tolerant, and non-tolerant soybean plants. In some examples, the tolerance is observed in the context of herbicide carryover from the previous crop season.

The screening and selection may also be performed by exposing plants containing said progeny germplasm to mesotrione and/or isoxazole in an assay and selecting those plants showing tolerance or sensitivity to mesotrione and/or isoxazole herbicides as containing soybean germplasm into which germplasm having tolerance or sensitivity to mesotrione and/or isoxazole herbicides derived from the QTL mapped to linkage group L has been introgressed. The live assay may be any such assay known to the art, e.g., Taylor-Lovell et al. (2001) Weed Tech 15:95-102.

However, plant tolerance is a phenotypic spectrum consisting of extremes of high tolerance to non-tolerance with a continuum of intermediate tolerance phenotypes. Evaluation of these intermediate phenotypes using reproducible assays are of value to scientists who seek to identify genetic loci that impart tolerance, conduct marker assisted selection for tolerant population, and for introgression techniques to breed a tolerance trait into an elite soybean line, for example. Describing the continuum of tolerance can be done using any known scoring system or derivative thereof, including the scoring systems described in the Examples.

Automated Detection/Correlation Systems

In some examples, the methods include an automated system for detecting markers and or correlating the markers with a desired phenotype (e.g., tolerance or susceptibility). Thus, a typical system can include a set of marker probes or primers configured to detect at least one favorable allele of one or more marker locus associated with tolerance or improved tolerance or sensitivity to mesotrione and/or isoxazole herbicides. These probes or primers are configured to detect the marker alleles noted in the tables and examples herein, e.g., using any available allele detection format, e.g., solid or liquid phase array based detection, microfluidic-based sample detection, etc.

In some examples markers involving linkage group L are used. In some examples a marker closely linked to the marker locus of SATT495, P10649C-3, SATT182, S03859-1, S00224-1, SATT388, SATT313, SATT613 (or another marker above SATT613), S03859-1-A, S08103-1-Q1, S08104-1-Q1, S08106-1-Q1, S08110-1-Q1, S08111-1-Q1, S08115-2-Q1, S08117-1-Q1, S08119-1-Q1, S08118-1-Q1, S08116-1-Q1, S08114-1-Q1, S08113-1-Q1, S08112-1-Q1, S08108-1-Q1, S08101-2-Q1, S08101-3-Q1, S08101-4-Q1, S08105-1-Q1, S08102-1-Q1, S08107-1-Q1, S08109-1-Q1, and S08101-1-Q1 is used, and the probe set is configured to detect the closely linked marker(s). In some examples, the marker locus is SATT495, P10649C-3, SATT182, S03859-1, S00224-1, SATT388, SATT313, SATT613 (or another marker above SATT613), S03859-1-A, S08103-1-Q1, S08104-1-Q1, S08106-1-Q1, S08110-1-Q1, S08111-1-Q1, S08115-2-Q1, S08117-1-Q1, S08119-1-Q1, S08118-1-Q1, S08116-1-Q1, S08114-1-Q1, S08113-1-Q1, S08112-1-Q1, S08108-1-Q1, S08101-2-Q1, S08101-3-Q1, S08101-4-Q1, S08105-1-Q1, S08102-1-Q1, S08107-1-Q1, S08109-1-Q1, and S08101-1-Q1, and the probe set is configured to detect the locus. Similarly, alleles of SATT495, P10649C-3, SATT182, S03859-1, S00224-1, SATT388, SATT313, SATT613 (or another marker above SATT613), S03859-1-A, S08103-1-Q1, S08104-1-Q1, S08106-1-Q1, S08110-1-Q1, S08111-1-Q1, S08115-2-Q1, S08117-1-Q1, S08119-1-Q1, S08118-1-Q1, S08116-1-Q1, S08114-1-Q1, S08113-1-Q1, S08112-1-Q1, S08108-1-Q1, S08101-2-Q1, S08101-3-Q1, S08101-4-Q1, S08105-1-Q1, S08102-1-Q1, S08107-1-Q1, S08109-1-Q1, and S08101-1-Q1 can be detected.

The typical system includes a detector that is configured to detect one or more signal outputs from the set of marker probes or primers, or amplicon thereof, thereby identifying the presence or absence of the allele. A wide variety of signal detection apparatus are available, including photo multiplier tubes, spectrophotometers, CCD arrays, arrays and array scanners, scanning detectors, phototubes and photodiodes, microscope stations, galvo-scans, microfluidic nucleic acid amplification detection appliances and the like. The precise configuration of the detector will depend, in part, on the type of label used to detect the marker allele, as well as the instrumentation that is most conveniently obtained for the user. Detectors that detect fluorescence, phosphorescence, radioactivity, pH, charge, absorbance, luminescence, temperature, magnetism or the like can be used. Typical detector examples include light (e.g., fluorescence) detectors or radioactivity detectors. For example, detection of a light emission (e.g., a fluorescence emission) or other probe label is indicative of the presence or absence of a marker allele. Fluorescent detection is generally used for detection of amplified nucleic acids (however, upstream and/or downstream operations can also be performed on amplicons, which can involve other detection methods). In general, the detector detects one or more label (e.g., light) emission from a probe label, which is indicative of the presence or absence of a marker allele. The detector(s) optionally monitors one or a plurality of signals from an amplification reaction. For example, the detector can monitor optical signals which correspond to "real time" amplification assay results.

System instructions that correlate the presence or absence of the favorable allele with the predicted tolerance are also provided. For example, the instructions can include at least one look-up table that includes a correlation between the presence or absence of the favorable alleles and the predicted tolerance or improved tolerance. The precise form of the instructions can vary depending on the components of the system, e.g., they can be present as system software in one or more integrated unit of the system (e.g., a microprocessor, computer or computer readable medium), or can be present in one or more units (e.g., computers or computer readable media) operably coupled to the detector. As noted, in one typical example, the system instructions include at least one look-up table that includes a correlation between the presence or absence of the favorable alleles and predicted tolerance or improved tolerance. The instructions also typically include instructions providing a user interface with the system, e.g., to permit a user to view results of a sample analysis and to input parameters into the system.

The system typically includes components for storing or transmitting computer readable data representing or designating the alleles detected, e.g., in an automated system. The computer readable media can include cache, main, and storage memory and/or other electronic data storage components (hard drives, floppy drives, storage drives, etc.) for storage of computer code. Data representing alleles detected can also be electronically, optically, magnetically o transmitted in a computer data signal embodied in a transmission medium over a network such as an intranet or internet or combinations thereof. The system can also or alternatively transmit data via wireless, IR, or other available transmission alternatives.

During operation, the system typically comprises a sample that is to be analyzed, such as a plant tissue, or material isolated from the tissue such as genomic DNA, amplified genomic DNA, cDNA, amplified cDNA, RNA, amplified RNA, or the like.

The phrase "allele detection/correlation system" refers to a system in which data entering a computer corresponds to physical objects or processes external to the computer, e.g., a marker allele, and a process that, within a computer, causes a physical transformation of the input signals to different output signals. In other words, the input data, e.g., amplification of a particular marker allele is transformed to output data, e.g., the identification of the allelic form of a chromosome segment. The process within the computer is a set of instructions, or "program," by which positive amplification or hybridization signals are recognized by the integrated system and attributed to individual samples as a genotype. Additional programs correlate the identity of individual samples with phenotypic values or marker alleles, e.g., statistical methods. In addition there are numerous e.g., C/C++ programs for computing, Delphi and/or Java programs for GUI interfaces, and productivity tools (e.g., Microsoft Excel and/or SigmaPlot) for charting or creating look up tables of relevant allele-trait correlations. Other useful software tools in the context of the integrated systems of the invention include statistical packages such as SAS, Genstat, Matlab, Mathematica, and S-Plus and genetic modeling packages such as QU-GENE. Furthermore, additional programming languages such as visual basic are also suitably employed in the integrated systems.

For example, tolerance marker allele values assigned to a population of progeny descending from crosses between elite lines are recorded in a computer readable medium, thereby establishing a database corresponding tolerance alleles with unique identifiers for members of the population of progeny. Any file or folder, whether custom-made or commercially available (e.g., from Oracle or Sybase) suitable for recording data in a computer readable medium is acceptable as a database. Data regarding genotype for one or more molecular markers, e.g., ASH, SSR, RFLP, RAPD, AFLP, SNP, isozyme markers or other markers as described herein, are similarly recorded in a computer accessible database. Optionally, marker data is obtained using an integrated system that automates one or more aspects of the assay (or assays) used to determine marker(s) genotype. In such a system, input data corresponding to genotypes for molecular markers are relayed from a detector, e.g., an array, a scanner, a CCD, or other detection device directly to files in a computer readable medium accessible to the central processing unit. A set of system instructions (typically embodied in one or more programs) encoding the correlations between tolerance and the alleles of the invention is then executed by the computational device to identify correlations between marker alleles and predicted trait phenotypes.

Typically, the system also includes a user input device, such as a keyboard, a mouse, a touchscreen, or the like, for, e.g., selecting files, retrieving data, reviewing tables of maker information, etc., and an output device (e.g., a monitor, a printer, etc.) for viewing or recovering the product of the statistical analysis.

Integrated systems comprising a computer or computer readable medium comprising set of files and/or a database with at least one data set that corresponds to the marker alleles herein are provided. The systems optionally also includes a user interface allowing a user to selectively view one or more of these databases. In addition, standard text manipulation software such as word processing software (e.g., Microsoft Word™ or Corel Wordperfect™) and database or spreadsheet software (e.g., spreadsheet software such as Microsoft Excel™ Corel Quattro Pro™, or database programs such as Microsoft Access™ or Paradox™) can be used in conjunction with a user interface (e.g., a GUI in a standard operating system such as a Windows, Macintosh, Unix or Linux system) to manipulate strings of characters corresponding to the alleles or other features of the database.

The systems optionally include components for sample manipulation, e.g., incorporating robotic devices. For example, a robotic liquid control armature for transferring solutions (e.g., plant cell extracts) from a source to a destination, e.g., from a microtiter plate to an array substrate, is optionally operably linked to the digital computer (or to an additional computer in the integrated system). An input device for entering data to the digital computer to control high throughput liquid transfer by the robotic liquid control armature and, optionally, to control transfer by the armature to the solid support is commonly a feature of the integrated system. Many such automated robotic fluid handling systems are commercially available. For example, a variety of automated systems are available from Caliper Technologies (Hopkinton, Mass.), which utilize various Zymate systems, which typically include, e.g., robotics and fluid handling modules. Similarly, the common ORCA® robot, which is used in a variety of laboratory systems, e.g., for microtiter tray manipulation, is also commercially available, e.g., from Beckman Coulter, Inc. (Fullerton, Calif.). As an alternative to conventional robotics, microfluidic systems for performing fluid handling and detection are now widely available, e.g., from Caliper Technologies Corp. (Hopkinton, Mass.) and Agilent technologies (Palo Alto, Calif.).

Systems for molecular marker analysis can include a digital computer with one or more of high-throughput liquid control software, image analysis software for analyzing data from marker labels, data interpretation software, a robotic liquid control armature for transferring solutions from a source to a destination operably linked to the digital computer, an input device (e.g., a computer keyboard) for entering data to the digital computer to control high throughput liquid transfer by the robotic liquid control armature and, optionally, an image scanner for digitizing label signals from labeled probes hybridized, e.g., to markers on a solid support operably linked to the digital computer. The image scanner interfaces with the image analysis software to provide a measurement of, e.g., nucleic acid probe label intensity upon hybridization to an arrayed sample nucleic acid population (e.g., comprising one or more markers), where the probe label intensity measurement is interpreted by the data interpretation software to show whether, and to what degree, the labeled probe hybridizes to a marker nucleic acid (e.g., an amplified marker allele). The data so derived is then correlated with sample identity, to determine the identity of a plant with a particular genotype(s) for particular markers or alleles, e.g., to facilitate marker assisted selection of soybean plants with favorable allelic forms of chromosome segments involved in agronomic performance (e.g., tolerance or improved tolerance).

Optical images, e.g., hybridization patterns viewed (and, optionally, recorded) by a camera or other recording device (e.g., a photodiode and data storage device) are optionally further processed in any of the embodiments herein, e.g., by digitizing the image and/or storing and analyzing the image on a computer. A variety of commercially available peripheral equipment and software is available for digitizing, storing and analyzing a digitized video or digitized optical image.

Stacking of Traits and Additional Traits of Interest

In some embodiments, the polynucleotide conferring the tolerance in the plants are engineered into a molecular stack with at least one additional polynucleotide. The additional polynucleotide may confer any additional trait of interest, such as tolerance to an additional herbicide, insects, disease, or any other desirable trait. A trait, as used herein, refers to the phenotype derived from a particular sequence or groups of sequences. For example, herbicide-tolerance polynucleotides may be stacked with any other polynucleotides encoding polypeptides having pesticidal and/or insecticidal activity, such as *Bacillus thuringiensis* toxic proteins (described in U.S. Pat. Nos. 5,366,892; 5,747,450; 5,737,514; 5,723,756; 5,593,881; Geiser et al. (1986) Gene 48:109; Lee et al. (2003) Appl. Environ. Microbiol. 69:4648-4657 (Vip3A); Galitzky et al. (2001) Acta Crystallogr. D. Biol. Crystallogr. 57:1101-1109 (Cry3Bb1); and Herman et al. (2004) J. Agric. Food Chem. 52:2726-2734 (Cry1F)), lectins (Van Damme et al. (1994) Plant Mol. Biol. 24: 825, pentin (described in U.S. Pat. No. 5,981,722), and the like. The combinations generated can also include multiple copies of any one of the polynucleotides of interest.

In some embodiments, an herbicide-tolerance polynucleotide described herein may be stacked with other herbicide-tolerance traits to create a transgenic plant with further improved properties. Other herbicide-tolerance polynucleotides that could be used in such embodiments include those conferring tolerance to the same herbicide by other modes of action, or a different herbicide. Other traits that could be combined with herbicide-tolerance polynucleotides include those derived from polynucleotides that confer on the plant the capacity to produce a higher level of 5-enolpyruvylshikimate-3-phosphate synthase (EPSPS), for example, as more fully described in U.S. Pat. Nos. 6,248,876 B1; 5,627, 061; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; U.S. Pat. No. Re. 36,449; U.S. Pat. Nos. RE 37,287 E; and 5,491,288; and WO 97/04103; WO 00/66746; WO 01/66704; and WO 00/66747. Other traits that could be combined with herbicide-tolerance polynucleotides include those conferring tolerance to sulfonylurea and/or imidazolinone, for example, as described more fully in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270.

In some embodiments, herbicide-tolerance polynucleotides of the plants may be stacked with, for example, hydroxyphenylpyruvatedioxygenases which are enzymes that catalyze the reaction in which para-hydroxyphenylpyruvate (HPP) is transformed into homogentisate. Molecules which inhibit this enzyme and which bind to the enzyme in order to inhibit transformation of the HPP into homogentisate are useful as herbicides. Traits conferring tolerance to such herbicides in plants are described in U.S. Pat. Nos. 6,245,968 B1; 6,268,549; and 6,069,115; and WO 99/23886. Other examples of suitable herbicide-tolerance traits that could be stacked with herbicide-tolerance polynucleotides include aryloxyalkanoate dioxygenase polynucleotides (which reportedly confer tolerance to 2,4-D and other phenoxy auxin herbicides as well as to aryloxyphenoxypropionate herbicides as described, for example, in WO2005/107437) and dicamba-tolerance polynucleotides as described, for example, in Herman et al. (2005) J. Biol. Chem. 280: 24759-24767.

Other examples of herbicide-tolerance traits that could be combined with herbicide-tolerance polynucleotides include those conferred by polynucleotides encoding an exogenous phosphinothricin acetyltransferase, as described in U.S. Pat. Nos. 5,969,213; 5,489,520; 5,550,318; 5,874,265; 5,919,675; 5,561,236; 5,648,477; 5,646,024; 6,177,616; and 5,879,903. Plants containing an exogenous phosphinothricin acetyltransferase can exhibit improved tolerance to glufosinate herbicides, which inhibit the enzyme glutamine synthase. Other examples of herbicide-tolerance traits that could be combined with the herbicide-tolerance polynucleotides include those conferred by polynucleotides conferring altered protoporphyrinogen oxidase (protox) activity, as described in U.S. Pat. Nos. 6,288,306 B1; 6,282,837 B1; and 5,767,373; and WO 01/12825. Plants containing such polynucleotides can exhibit improved tolerance to any of a variety of herbicides which target the protox enzyme (also referred to as protox inhibitors).

Other examples of herbicide-tolerance traits that could be combined with herbicide-tolerance polynucleotides include those conferring tolerance to at least one herbicide in a plant such as, for example, a maize plant or horseweed. Herbicide-tolerant weeds are known in the art, as are plants that vary in their tolerance to particular herbicides. See, e.g., Green and Williams (2004) "Correlation of Corn (Zea mays) Inbred Response to Nicosulfuron and Mesotrione," poster presented at the WSSA Annual Meeting in Kansas City, Mo., Feb. 9-12, 2004; Green (1998) Weed Technology 12:474-477; Green and Ulrich (1993) Weed Science 41:508-516. The trait(s) responsible for these tolerances can be combined by breeding or via other methods with herbicide-tolerance polynucleotides to provide a plant as well as methods of use thereof.

In this manner, plants that are more tolerant to multiple herbicides are disclosed. Accordingly, methods for growing a crop (i.e., for selectively controlling weeds in an area of cultivation) that comprise treating an area of interest (e.g., a field or area of cultivation) with at least one herbicide to which the plant is tolerant are likewise disclosed. In some embodiments, methods further comprise treatment with additional herbicides to which the plant is tolerant. In such embodiments, generally the methods permit selective control of weeds without significantly damaging the crop. As used herein, an "area of cultivation" comprises any region in which one desires to grow a plant. Such areas of cultivations include, but are not limited to, a field in which a plant is cultivated (such as a crop field, a sod field, a tree field, a managed forest, a field for culturing fruits and vegetables, etc), a greenhouse, a growth chamber, etc.

Herbicide-tolerant traits can also be combined with at least one other trait to produce plants that further comprise a variety of desired trait combinations including, but not limited to, traits desirable for animal feed such as high oil content (e.g., U.S. Pat. No. 6,232,529); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)); the disclosures of which are herein incorporated by reference. Desired trait combinations also include LLNC (low linolenic acid content; see, e.g., Dyer et al. (2002) Appl. Microbiol. Biotechnol. 59:224-230) and OLCH (high oleic acid content; see, e.g., Fernandez-Moya et al. (2005) J. Agric. Food Chem. 53:5326-5330).

Herbicide-tolerant traits of interest can also be combined with other desirable traits such as, for example, fumonisim detoxification genes (U.S. Pat. No. 5,792,931), avirulence and disease resistance genes (Jones et al. (1994) Science 266:789; Martin et al. (1993) Science 262:1432; Mindrinos et al. (1994) Cell 78:1089), and traits desirable for processing or process products such as modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) J. Bacteriol. 170:5837-5847) facilitate expression of polyhydroxyalkanoates (PHAs)); the disclosures of which are herein incorporated by reference. One could also combine herbicide-tolerant polynucleotides with polynucleotides providing agronomic traits such as male sterility (e.g., see U.S. Pat. No. 5,583,210), stalk strength, flowering time, or transformation technology traits such as cell cycle regulation or gene targeting (e.g., WO 99/61619, WO 00/17364, and WO 99/25821); the disclosures of which are herein incorporated by reference.

In another embodiment, the herbicide-tolerant traits of interest can also be combined with the Rcg1 sequence or biologically active variant or fragment thereof. The Rcg1 sequence is an anthracnose stalk rot resistance gene in corn. See, e.g., U.S. patent application Ser. Nos. 11/397,153, 11/397,275, and 11/397,247, each of which is herein incorporated by reference.

These stacked combinations can be created by any method including, but not limited to, breeding plants by any conventional or TopCross methodology, or genetic transformation. If the sequences are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, e.g., WO99/25821, WO99/25854, WO99/25840, WO99/25855, and WO99/25853, all of which are herein incorporated by reference.

Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,736,514; 5,723,756; 5,593,881; and Geiser et al. (1986) Gene 48: 109); and the like.

Genes encoding disease resistance traits include detoxification genes, such as against fumonosin (U.S. Pat. No. 5,792,931); avirulence (avr) and disease resistance (R) genes (Jones et al. (1994) Science 266: 789; Martin et al. (1993) Science 262: 1432; and Mindrinos et al. (1994) Cell 78: 1089); and the like.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

Methods of Controlling Weeds

Methods are provided for controlling weeds in an area of cultivation, preventing the development or the appearance of herbicide resistant weeds in an area of cultivation, producing a crop, and increasing crop safety. The term "controlling," and derivations thereof, for example, as in "controlling weeds" refers to one or more of inhibiting the growth, germination, reproduction, and/or proliferation of; and/or killing, removing, destroying, or otherwise diminishing the occurrence and/or activity of a weed.

The mesotrione and/or isoxazole tolerant plants display a modified tolerance to herbicides and therefore allow for the application of one or more herbicides at rates that would significantly damage control plants and further allow for the application of combinations of herbicides at lower concentrations than normally applied which still continue to selectively control weeds. The mesotrione and/or isoxazole tolerant plants may also display tolerance to HPPD-inhibitor herbicide carryover from a previous crop growing season. In addition, the mesotrione and/or isoxazole tolerant plants can be used in combination with herbicide blends technology and thereby make the application of chemical pesticides more convenient, economical, and effective for the producer.

The methods comprise planting the area of cultivation with mesotrione and/or isoxazole tolerant crop seeds or plants, and applying to any crop, crop part, weed or area of cultivation thereof an effective amount of a mesotrione and/or isoxazole herbicide of interest. It is recognized that the herbicide can be applied before or after the crop is planted in the area of cultivation. Such herbicide applications can include an application of a mesotrione and/or an isoxazole chemistry, or any combination thereof.

In certain examples, the combination of herbicides comprises a glyphosate, a glufosinate, a dicamba, a bialaphos, a phosphinothricin, a protox inhibitor, a sulfonylurea, an imidazolinone, a chlorsulfuron, an imazapyr, a chlorimuron-ethyl, a quizalofop, an HPPD, a PPO, and/or a fomesafen, or combinations thereof, wherein said effective amount is tolerated by the crop and controls weeds. Any effective amount of these herbicides can be applied, wherein the effective amount is any amount that differentiates between plant cells, plants, and/or seed comprising a mesotrione and/or isoxazole tolerance allele, a mesotrione and/or isoxazole tolerance polynucleotide, and/or a polynucleotide encoding an ABC transporter protein that confers tolerance to herbicide formulations comprising a mesotrione and/or isoxazole. In some examples the herbicides are applied simultaneously, in some examples the herbicides are applied sequentially, in some examples the herbicides are applied as pre-emergent treatments, in some examples the herbicides are applied as post-emergent treatments, in some examples the herbicides are applied as a combination of pre- and post-emergent treatments.

In some examples, the method of controlling weeds comprises planting the area with mesotrione and/or isoxazole tolerant crop seeds or plants and applying to the crop, crop part, seed of said crop or the area under cultivation, an effective amount of a herbicide, wherein said effective amount comprises an amount that is not tolerated by a control crop when applied to the control crop, crop part, seed or the area of cultivation, wherein the control crop does not express a polynucleotide that encodes an herbicide-tolerance polypeptide. In specific embodiments, combinations of herbicides may be used, such as when an additional tolerance trait is incorporated into the plant.

In another embodiment, the method of controlling weeds comprises planting the area with a mesotrione and/or isoxazole tolerant crop seeds or plant and applying to the crop, crop part, seed of said crop or the area under cultivation, an effective amount of a herbicide, wherein said effective amount comprises a level that is above the recommended label use rate for the crop, wherein said effective amount is tolerated when applied to the mesotrione and/or isoxazole tolerant crop, crop part, seed, or the area of cultivation thereof.

Any herbicide can be applied to the tolerant crop, crop part, or the area of cultivation containing said crop plant. Classifications of herbicides (i.e., the grouping of herbicides into classes and subclasses) is well-known in the art and includes classifications by HRAC (Herbicide Resistance Action Committee) and WSSA (the Weed Science Society of America) (see also, Retzinger and Mallory-Smith (1997) Weed Technology 11: 384-393). An abbreviated version of the HRAC classification (with notes regarding the corresponding WSSA group) is set forth in Table 1.

TABLE 1

Abbreviated HRAC classification table.

| HRAC Group | Mode of Action | Chemical Family | Active Ingredient | WSSA Group |
|---|---|---|---|---|
| A | Inhibition of acetyl CoA carboxylase (ACCase) | Aryloxyphenoxy-propionate "FOPs" | clodinafop-propargyl cyhalofop-butyl diclofop-methyl fenoxaprop-P-ethyl fluazifop-P-butyl haloxyfop-R-methyl propaquizafop quizalofop-P-ethyl | 1 |
| | | Cyclohexanedione "DIMs" | alloxydim butroxydim clethodim cycloxydim profoxydim sethoxydim tepraloxydin tralkoxydim | |
| B | Inhibition of acetolactate synthase ALS (acetohydroxyacid synthase AHAS) | Phenylpyrazoline "DEN" Sulfonylurea | pinoxaden amidosulfuron azimsulfuron bensulfuron-methyl chlorimuron-ethyl chlorsulfuron cinosulfuron cyclosulfamuron ethametsulfuron-methyl ethoxysulfuron flazasulfuron flupyrsulfuron-methyl-Na foramsulfuron halosulfuron-methyl imazosulfuron iodosulfuron mesosulfuron metsulfuron-methyl nicosulfuron oxasulfuron primisulfuron-methyl prosulfuron pyrazosulfuron-ethyl rimsulfuron sulfometuron-methyl sulfosulfuron thifensulfuron-methyl triasulfuron tribenuron-methyl trifloxysulfuron triflusulfuron-methyl tritosulfuron | 2 |
| | | Imidazolinone | imazapic imazamethabenz-methyl imazamox imazapyr imazaquin imazethapyr | |
| | | Triazolopyrimidine | cloransulam-methyl diclosulam florasulam flumetsulam metosulam penoxsulam | |
| | | Pyrimidinyl(thio)benzoate | bispyribac-Na pyribenzoxim pyriftalid pyrithiobac-Na | |

TABLE 1-continued

Abbreviated HRAC classification table.

| HRAC Group | Mode of Action | Chemical Family | Active Ingredient | WSSA Group |
|---|---|---|---|---|
| | | Sulfonylaminocarbonyl-triazolinone | pyriminobac-methyl flucarbazone-Na propoxycarbazone-Na | |
| C1 | Inhibition of photosynthesis at photosystem II | Triazine | ametryne atrazine cyanazine desmetryne dimethametryne prometon prometryne propazine simazine simetryne terbumeton terbuthylazine terbutryne trietazine | 5 |
| | | Triazinone | hexazinone metamitron metribuzin | |
| | | Triazolinone | amicarbazone | |
| | | Uracil | bromacil lenacil terbacil | |
| | | Pyridazinone | pyrazon = chloridazon | |
| | | Phenyl-carbamate | desmedipham phenmedipham | |
| C2 | Inhibition of photosynthesis at photosystem II | Urea | chlorobromuron chlorotoluron chloroxuron dimefuron diuron ethidimuron fenuron fluometuron (see F3) isoproturon isouron linuron methabenzthiazuron metobromuron metoxuron monolinuron neburon siduron tebuthiuron | 7 |
| | | Amide | propanil pentanochlor | |
| C3 | Inhibition of photosynthesis at photosystem II | Nitrile | bromofenoxim bromoxynil ioxynil | 6 |
| | | Benzothiadiazinone | bentazon | |
| | | Phenyl-pyridazine | pyridate pyridafol | |
| D | Photosystem-I-electron diversion | Bipyridylium | diquat paraquat | 22 |
| E | Inhibition of protoporphyrinogen oxidase (PPO) | Diphenylether | acifluorfen-Na bifenox chlomethoxyfen fluoroglycofen-ethyl fomesafen halosafen lactofen oxyfluorfen | 14 |
| | | Phenylpyrazole | fluazolate pyraflufen-ethyl | |
| | | N-phenylphthalimide | cinidon-ethyl flumioxazin flumiclorac-pentyl | |
| | | Thiadiazole | fluthiacet-methyl thidiazimin | |

TABLE 1-continued

Abbreviated HRAC classification table.

| HRAC Group | Mode of Action | Chemical Family | Active Ingredient | WSSA Group |
|---|---|---|---|---|
| | | Oxadiazole | oxadiazon | |
| | | | oxadiargyl | |
| | | Triazolinone | azafenidin | |
| | | | carfentrazone-ethyl | |
| | | | sulfentrazone | |
| | | Oxazolidinedione | pentoxazone | |
| | | Pyrimidindione | benzfendizone | |
| | | | butafenacil | |
| | | Other | pyraclonil | |
| | | | profluazol | |
| | | | flufenpyr-ethyl | |
| F1 | Bleaching: Inhibition of carotenoid biosynthesis at the phytoene desaturase step (PDS) | Pyridazinone | norflurazon | 12 |
| | | Pyridinecarboxamide | diflufenican | |
| | | | picolinafen | |
| | | Other | beflubutamid | |
| | | | fluridone | |
| | | | flurochloridone | |
| | | | flurtamone | |
| F2 | Bleaching: Inhibition of 4-hydroxyphenyl-pyruvate-dioxygenase (4-HPPD) | Triketone | mesotrione | 27 |
| | | | sulcotrione | |
| | | Isoxazole | isoxachlortole | |
| | | | isoxazole | |
| | | Pyrazole | benzofenap | |
| | | | pyrazolynate | |
| | | | pyrazoxyfen | |
| | | Other | benzobicyclon | |
| F3 | Bleaching: Inhibition of carotenoid biosynthesis (unknown target) | Triazole | amitrole (in vivo inhibition of lycopene cyclase | 11 |
| | | Isoxazolidinone | clomazone | 13 |
| | | Urea | fluometuron (see C2) | |
| | | Diphenylether | aclonifen | |
| G | Inhibition of EPSP synthase | Glycine | glyphosate | 9 |
| | | | sulfosate | |
| H | Inhibition of glutamine synthetase | Phosphinic acid | glufosinate-ammonium | 10 |
| | | | bialaphos = bilanaphos | |
| I | Inhibition of DHP (dihydropteroate) synthase | Carbamate | asulam | 18 |
| K1 | Microtubule assembly inhibition | Dinitroaniline | benefin = benfluralin | 3 |
| | | | butralin | |
| | | | dinitramine | |
| | | | ethalfluralin | |
| | | | oryzalin | |
| | | | pendimethalin | |
| | | | trifluralin | |
| | | Phosphoroamidate | amiprophos-methyl | |
| | | | butamiphos | |
| | | Pyridine | dithiopyr | |
| | | | thiazopyr | |
| | | Benzamide | propyzamide = pronamide | |
| | | | tebutam | |
| | | Benzoic acid | DCPA = chlorthal-dimethyl | |
| K2 | Inhibition of mitosis/microtubule organisation | Carbamate | chlorpropham | 23 |
| | | | propham | |
| | | | carbetamide | |

TABLE 1-continued

Abbreviated HRAC classification table.

| HRAC Group | Mode of Action | Chemical Family | Active Ingredient | WSSA Group |
|---|---|---|---|---|
| K3 | Inhibition of VLCFAs (Inhibition of cell division) | Chloroacetamide | acetochlor alachlor butachlor dimethachlor dimethanamid metazachlor metolachlor pethoxamid pretilachlor propachlor propisochlor thenylchlor | 15 |
| | | Acetamide | diphenamid napropamide naproanilide | |
| | | Oxyacetamide | flufenacet mefenacet | |
| | | Tetrazolinone | fentrazamide | |
| | | Other | anilofos cafenstrole piperophos | |
| L | Inhibition of cell wall (cellulose) synthesis | Nitrile | dichlobenil chlorthiamid | 20 |
| | | Benzamide | isoxaben | 21 |
| | | Triazolocarboxamide | flupoxam | |
| | | Quinoline carboxylic acid | quinclorac (for monocots) (also group O) | 26 |
| M | Uncoupling (Membrane disruption) | Dinitrophenol | DNOC dinoseb dinoterb | 24 |
| N | Inhibition of lipid synthesis—not ACCase inhibition | Thiocarbamate | butylate cycloate dimepiperate EPTC esprocarb molinate orbencarb pebulate prosulfocarb thiobencarb = benthiocarb tiocarbazil triallate vernolate | 8 |
| | | Phosphorodithioate | bensulide | |
| | | Benzofuran | benfuresate ethofumesate | |
| | | Chloro-Carbonic-acid | TCA dalapon flupropanate | 26 |
| O | Action like indole acetic acid (synthetic auxins) | Phenoxy-carboxylic-acid | clomeprop 2,4-D 2,4-DB dichlorprop = 2,4-DP MCPA MCPB mecoprop = MCPP = CMPP | 4 |
| | | Benzoic acid | chloramben dicamba TBA | |
| | | Pyridine carboxylic acid | clopyralid fluroxypyr picloram triclopyr | |
| | | Quinoline carboxylic acid | quinclorac (also group L) quinmerac | |
| | | Other | benazolin-ethyl | |
| P | Inhibition of auxin transport | Phthalamate | naptalam | 19 |
| | | Semicarbazone | diflufenzopyr-Na | |

TABLE 1-continued

Abbreviated HRAC classification table.

| HRAC Group | Mode of Action | Chemical Family | Active Ingredient | WSSA Group |
|---|---|---|---|---|
| Z | Unknown (actual mode of action unknown, but likely that they differ in mode of action between themselves and from other groups) | Arylaminopropionic acid | Flamprop-M-methyl/-isopropyl | 25 |
| | | Pyrazolium | difenzoquat | 26 |
| | | Organoarsenical | DSMA<br>MSMA | 17 |
| | | Other | bromobutide<br>(chloro)-flurenol<br>cinmethylin<br>cumyluron<br>dazomet<br>dymron = daimuron<br>methyl-dimuron = methyl-dymron<br>etobenzanid<br>fosamine<br>indanofan<br>metam<br>oxaziclomefone<br>oleic acid<br>pelargonic acid<br>pyributicarb | 27 |

Herbicides can be classified by their mode of action and/or site of action and can also be classified by the time at which they are applied (e.g., pre-emergent or post-emergent), by the method of application (e.g., foliar application or soil application), or by how they are taken up by or affect the plant. Mode of action generally refers to the metabolic or physiological process within the plant that the herbicide inhibits or otherwise impairs, whereas site of action generally refers to the physical location or biochemical site within the plant where the herbicide acts or directly interacts. Herbicides can be classified in various ways, including by mode of action and/or site of action. Often, an herbicide-tolerance gene that confers tolerance to a particular herbicide or other chemical on a plant expressing it will also confer tolerance to other herbicides or chemicals in the same class or subclass, for example, a class or subclass set forth in the table above. Thus, in some examples, a transgenic plant is tolerant to more than one herbicide or chemical in the same class or subclass, such as, for example, an inhibitor of PPO, a sulfonylurea, a glyphosate, or a synthetic auxin. In some examples the plant is transgenic for one or more of the herbicide tolerance traits, non-transgenic for one of more of the tolerance traits, or any combination thereof Typically, the plants provided can tolerate treatment with different types of herbicides (i.e., herbicides having different modes of action and/or different sites of action) as well as with higher amounts of herbicides than previously known plants, thereby permitting improved weed management strategies that are recommended in order to reduce the incidence and prevalence of herbicide-tolerant weeds. Specific herbicide combinations can be employed to effectively control weeds.

A transgenic crop plant which can be selected for use in crop production based on the prevalence of herbicide-tolerant weed species in the area where the transgenic crop is to be grown is provided. Methods are known in the art for assessing the herbicide tolerance of various weed species.

Weed management techniques are also known in the art, such as for example, crop rotation using a crop that is tolerant to an herbicide to which the local weed species are not tolerant. A number of entities monitor and publicly report the incidence and characteristics of herbicide-tolerant weeds, including the Herbicide Resistance Action Committee (HRAC), the Weed Science Society of America, and various state agencies (see, e.g., herbicide tolerance scores for various broadleaf weeds from the 2004 Illinois Agricultural Pest Management Handbook), and one of skill in the art would be able to use this information to determine which crop and herbicide combinations should be used in a particular location.

These entities also publish advice and guidelines for preventing the development and/or appearance of and controlling the spread of herbicide tolerant weeds (see, e.g., Owen and Hartzler (2004), 2005 Herbicide Manual for Agricultural Professionals, Pub. WC 92 Revised (Iowa State University Extension, Iowa State University of Science and Technology, Ames, Iowa); Weed Control for Corn, Soybeans, and Sorghum, Chapter 2 of "2004 Illinois Agricultural Pest Management Handbook" (University of Illinois Extension, University of Illinois at Urbana-Champaign, Ill.); Weed Control Guide for Field Crops, MSU Extension Bulletin E434 (Michigan State University, East Lansing, Mich.)).

Also included are plant cells, plants, and/or seeds produced by any of the foregoing methods.

The present invention is illustrated by the following examples. The foregoing and following description of the present invention and the various embodiments are not intended to be limiting of the invention but rather are illustrative thereof. Hence, it will be understood that the invention is not limited to the specific details of these examples.

EXAMPLES

Example 1: Identification of Isoxafutole Tolerant and Sensitive Soybean Lines—Herbicide Screening Bioassay and Intergroup Association Marker Based Diagnostic Two soybean mapping populations were used to confirm significant QTLs related to tolerance and susceptibility to mesotrione and/or isoxazole herbicides, to identify any potential QTLs associated with the tolerance or susceptibility to these herbicides, and to identify any varietal variation due to differences between the two herbicide chemistries used in the study. The mesotrione herbicide used in this study was Callisto® (referred to as Herbicide B); the isoxazole herbicide used in this study was Balance Pro® (referred to as Herbicide A).

Part 1:

Studies were conducted using herbicides A and B and were performed at two locations, Princeton, Ill. and Johnston, Iowa Herbicide screening protocols developed in the summer of 2008 determined the optimum herbicide rate, application timing and the best time to evaluate soybean injury following application.

Herbicide A and B were applied as a pre-plant incorporated herbicide. The application rate for Herbicide A was based on soil organic matter and was applied at half the recommended labeled rate. Herbicide B was applied at half the pre-plant incorporated label rate. Both herbicides were applied using an ATV sprayer outfitted with a 10-foot boom, GPS and a Raven control system. The herbicides were applied at a rate of 30 gallons of water per acre and a spray pressure of 35-40 psi. An agitation system was used to maintain herbicide suspension in the water spray solution. Since both herbicides A and B were used in the same field, the sprayer was cleaned out between applications and a 10-foot buffer strip was used to help separate the two herbicides in the field to ensure no spray overlap.

The herbicides were incorporated into the soil to a depth of 1-2 inches using a field cultivator with rolling baskets 2-5 days following application (Table 2). Incorporation was performed in two directions to ensure even distribution of the herbicide in the soil.

The soybeans were planted into the soil to a depth of 1-1.5 inches using an Almaco 4-row index planter set on 30-inch row spacing. All plots were planted as single row plots with 25 seeds for 4.5 feet of planted row with a three-foot alleyway. The planted population was approximately 90,000 seeds per acre. Both Princeton and Johnston locations were planted on June 4. The herbicide application, planting, and rating dates for both Princeton and Johnston locations are presented in Table 2.

Soybean varietal herbicide reactions were evaluated using visual scores for plant growth reduction (STNT) and crop injury rating (HERSC) using descriptions defined below. Two ratings were conducted at both locations; the initial rating (V3) was based off of the clearest distinction of symptoms across the experiments. A second rating (V5 or V6) was conducted to ensure accuracy and note any varietal variation over time. An untreated check was used as a guide for the expected plant growth and development over time.

Plant Growth Reduction Rating (STNT)

1-9 herbicide reaction scale for plant growth reduction:
  9=no plant growth reduction from the herbicide
  8=<5% plant growth reduction
  7=>5% and <20% plant growth reduction
  6=>20% and <35% plant growth reduction
  5=>35% and <50% plant growth reduction
  4=>50 and <65% plant growth reduction
  3=>65 and <80% plant growth reduction
  2=>80 and <95% plant growth reduction
  1=>95% plant growth reduction Crop Injury Rating (HERSC)

1-9 herbicide reaction scale for crop injury (both chlorotic and necrotic tissue):
  9=no crop injury
  8=<5% crop injury
  7=>5% and <20% crop injury
  6=>20% and <35% crop injury
  5=>35% and <50% crop injury
  4=>50 and <65% crop injury
  3=>65 and <80% crop injury
  2=>80 and <95% crop injury
  1=>95% crop injury Two mapping populations were used that contained known susceptible and tolerant parents that were fixed and carried different alleles for two QTLs identified on linkage group L. The mapping populations were screened using herbicide A and the herbicide screening protocol described above. Two populations (Pop A and Pop B) of 90 randomly selected F3:F5 lines were used in the study. Four replications of the populations were placed in a row by column design to help adjust means due to field variation. The parents of each population were replicated 3 times per replication for a total of 12 times per location. An analysis of variance (ANOVA) was conducted to identify significant differences between the varieties within the populations.

A variety trial was conducted using 144 varieties with herbicides A and B and the herbicide screening protocol described above. Four replications of the varieties were placed in a row by column design to help adjust means due to field variation for both herbicides. The 144 lines included 52 susceptible and 61 tolerant lines identified previously as well as lines identified as moderate but containing the susceptible or tolerant allele for the QTLs.

An ANOVA was run on the STNT and HERSC data to determine any significant differences between soybean varieties. The herbicide response and the varieties were classified into tolerant and susceptible groups to be analyzed using available SSR and SNP markers for identification of other potential QTLs associated with the trait. The tolerant and susceptible classes were analyzed to observe marker trait

TABLE 2

| | | Herbicide Application, tillage, planting and rating dates | | | | | |
|---|---|---|---|---|---|---|---|
| Location | Herbicide Application | Tilled In | Planting Date | 1st Rating | Untreated Crop Stage | 2nd Rating | Untreated Crop Stage |
| Princeton, IL | May 29, 2009 | Jun. 4, 2009 | Jun. 4, 2009 | Jun. 29, 2009 | V3 | Jul. 8, 2009 | V6 |
| Johnston, IA | Jun. 2, 2009 | Jun. 4, 2009 | Jun. 4, 2009 | Jun. 30, 2009 | V3 | Jul. 7, 2009 | V5 | associations by comparing the allelic frequencies of tolerant and susceptible varieties. This analysis used all available genome wide data produced for the markers and the varieties to run the analysis. Significant markers were then identified and potential QTL regions were recognized for candidates causing tolerant reactions. This data was used to help identify additional polymorphic markers within the mapping populations. Table 3 indicates the results of the various varieties tested.

TABLE 3

Mapping population analysis

| Grouping | HERSC score | Adjusted mean |
|---|---|---|
| SUS | 1 | 2.2915 |
| SUS | 1 | 2.3105 |
| SUS | 1 | 2.333 |
| SUS | 1 | 2.3955 |
| SUS | 1 | 2.4045 |
| SUS | 1 | 2.4155 |
| SUS | 2 | 2.4825 |
| SEG | 2 | 2.547 |
| SUS | 2 | 2.577 |
| SUS | 2 | 2.888 |
| SUS | 2 | 2.9185 |
| SUS | 3 | 3.083 |
| SEG | 3 | 3.091 |
| SUS | 3 | 3.1775 |
| SEG | 3 | 3.207 |
| SUS | 3 | 3.252 |
| SUS | 3 | 3.3115 |
| SEG | 4 | 3.427 |
| SEG? | 4 | 3.5305 |
| SEG | 4 | 3.544 |
| SUS | 4 | 3.5845 |
| SEG | 4 | 3.589 |
| SUS | 4 | 3.6135 |
| SUS | 4 | 3.6575 |
| SEG | 4 | 3.662 |
| SEG | 5 | 3.729 |
| SEG | 5 | 3.73 |
| SUS | 5 | 3.7435 |
| SEG | 5 | 3.843 |
| TOL | 5 | 3.89 |
| SEG | 5 | 3.9255 |
| SEG | 5 | 3.9925 |
| SEG | 5 | 4.0415 |
| SEG | 5 | 4.0755 |
| SEG | 5 | 4.1025 |
| TOL | 5 | 4.1315 |
| TOL | 5 | 4.171 |
| SEG | 6 | 4.273 |
| SEG | 6 | 4.276 |
| SEG | 6 | 4.325 |
| SEG? | 4 | 4.331 |
| SEG | 4 | 4.375 |
| TOL | 6 | 4.4225 |
| SEG | 6 | 4.436 |
| SEG | 6 | 4.456 |
| SEG | 6 | 4.4955 |
| TOL | 6 | 4.5525 |
| TOL | 6 | 4.5905 |
| TOL | 6 | 4.6135 |
| SEG | 6 | 4.627 |
| TOL | 6 | 4.652 |
| SEG | 6 | 4.652 |
| SEG | 6 | 4.7305 |
| TOL | 6 | 4.7785 |
| TOL | 6 | 4.7805 |
| TOL | 6 | 4.814 |
| SEG? | 6 | 4.815 |
| TOL | 6 | 4.827 |
| TOL | 6 | 4.883 |
| SEG | 6 | 4.955 |
| SEG | 7 | 5.005 |
| SEG | 7 | 5.018 |
| TOL | 7 | 5.0185 |
| SEG | 7 | 5.048 |

TABLE 3-continued

Mapping population analysis

| Grouping | HERSC score | Adjusted mean |
|---|---|---|
| TOL | 7 | 5.053 |
| TOL | 7 | 5.0635 |
| TOL | 7 | 5.0895 |
| TOL | 7 | 5.151 |
| TOL | 6 | 5.239 |
| SEG | 7 | 5.2525 |
| TOL | 7 | 5.258 |
| SEG | 7 | 5.263 |
| TOL | 5 | 5.312 |
| TOL | 7 | 5.357 |
| TOL | 7 | 5.358 |
| SEG? | 8 | 5.4165 |
| TOL | 8 | 5.4475 |
| SEG? | 8 | 5.512 |
| TOL | 8 | 5.5645 |
| TOL | 8 | 5.5975 |
| TOL | 8 | 5.6185 |
| TOL | 8 | 5.707 |
| TOL | 8 | 5.713 |
| TOL | 9 | 5.8935 |
| TOL | 9 | 5.904 |
| TOL | 9 | 6.022 |
| TOL | 7 | 6.0235 |
| SEG? | 9 | 6.1865 |
| TOL | 9 | 6.591 |
| TOL | 9 | 6.842 |
| SUS | 1 | 2.049 |
| TOL | 9 | 5.9145 |
| SUS | 2 | 2.733 |
| SUS | 2 | 2.748 |
| SUS | 2 | 2.801 |
| SUS | 2 | 2.883 |
| SUS | 2 | 2.938 |
| SUS | 2 | 2.9515 |
| SUS | 2 | 2.9955 |
| SEG? | 2 | 3.0555 |
| SUS | 1 | 2.4295 |
| SUS | 1 | 2.5185 |
| SUS | 1 | 2.6205 |
| SUS | 1 | 2.6395 |
| SUS | 3 | 3.1315 |
| SEG? | 3 | 3.1925 |
| SUS | 3 | 3.193 |
| SEG | 3 | 3.216 |
| SEG | 3 | 3.267 |
| SUS | 3 | 3.2875 |
| SUS | 3 | 3.2885 |
| SUS | 3 | 3.3375 |
| SUS | 4 | 3.3435 |
| SUS | 4 | 3.3555 |
| SUS | 4 | 3.361 |
| SUS | 4 | 3.428 |
| SUS | 4 | 3.449 |
| SUS | 4 | 3.539 |
| SUS | 4 | 3.5505 |
| SUS | 4 | 3.6335 |
| SUS | 5 | 3.681 |
| SUS | 5 | 3.793 |
| SUS | 5 | 3.8215 |
| SUS | 4 | 3.8395 |
| SUS | 5 | 4.01 |
| SEG? | 5 | 4.0635 |
| SUS | 5 | 4.072 |
| SEG | 5 | 4.1245 |
| SUS | 5 | 4.1535 |
| TOL | 5 | 4.239 |
| SEG | 6 | 4.3385 |
| SEG | 6 | 4.489 |
| TOL | 6 | 4.5315 |
| SEG | 6 | 4.5915 |
| SEG | 6 | 4.721 |
| TOL | 6 | 4.7345 |
| TOL | 6 | 4.8215 |
| TOL | 6 | 4.8495 |
| TOL | 6 | 4.8625 |
| TOL | 6 | 4.867 |

TABLE 3-continued

Mapping population analysis

| Grouping | HERSC score | Adjusted mean |
|---|---|---|
| TOL | 6 | 4.944 |
| TOL | 4 | 4.973 |
| TOL | 7 | 5.0845 |
| TOL | 7 | 5.0885 |
| TOL | 5 | 5.0955 |
| TOL | 7 | 5.1245 |
| TOL | 7 | 5.1505 |
| TOL | 7 | 5.1695 |
| TOL | 4 | 5.1885 |
| TOL | 7 | 5.221 |
| TOL | 7 | 5.228 |
| SEG | 7 | 5.2285 |
| SEG | 7 | 5.2805 |
| TOL | 7 | 5.3305 |
| SEG | 7 | 5.3345 |
| TOL | 8 | 5.381 |
| TOL | 8 | 5.3835 |
| TOL | 8 | 5.414 |
| TOL | 8 | 5.5165 |
| TOL | 8 | 5.535 |
| TOL | 8 | 5.55 |
| TOL | 8 | 5.5925 |
| TOL | 8 | 5.6125 |
| TOL | 8 | 5.617 |
| TOL | 8 | 5.6275 |
| TOL | 8 | 5.6435 |
| TOL | 8 | 5.67 |
| TOL | 8 | 5.7255 |
| TOL | 8 | 5.7645 |
| TOL | 8 | 5.8155 |
| TOL | 8 | 5.8245 |
| TOL | 8 | 5.8835 |
| TOL | 9 | 5.885 |
| TOL | 9 | 5.8885 |
| TOL | 9 | 5.9165 |
| TOL | 9 | 5.964 |
| TOL | 9 | 6.0095 |
| TOL | 9 | 6.2345 |
| TOL | 9 | 6.2655 |
| TOL | 9 | 6.286 |
| TOL | 7 | 6.3875 |
| TOL | 9 | 6.599 |
| SUS | 3 | 3.069 |
| TOL | 7 | 5.359 |

The experimental means for Herbicide A across both locations for HERSC2 was 4.695 with a standard deviation of 1.94. The coefficient of variation across the locations was 26.7.

Example 2: Determination of QTL and Marker Associations/Intergroup Analysis

There was significant (P<0.001) difference across varieties for Herbicide A. The LSD was 1.316 across all varieties. Predicted means by location were calculated using a linear model for the locations. The varieties were looked at individually by the adjusted means by location, the LSD value, the average score by location, and the 2008 data for each variety. This gave an overall view of each variety and allowed for a simple classification across all varieties. Any variety that showed a high rate of variability across the data was automatically placed in the segregating group.

The results of the ANOVA for both Herbicides A and B are reported in Table 4. The model used for the analysis was the incomplete block design and the affect of the model is described through the relative efficiency and the Czekanowski Coefficient (Czek Coeff). The relative efficiency is comparing the error terms of the more complex block (incomplete block, ICB) to the less complex model (randomized complete block, RCB). The relative efficiency for the variety trial using herbicide A was 111% and herbicide B was 123%. The Czek Coeff which reports the top 10 and 20 percent of the entries that were the same for both the RCB and ICB designs was 73 and 83% for the top 10% of entries and 86 and 90% for the top 20% of the entries for the variety trials using herbicides A and B, respectfully.

TABLE 4

Analysis of variance for the variety trial

|  | Herbicide A HERSC | Herbicide B HERSC |
|---|---|---|
| Experiment Mean | 4.695 | 4.585 |
| CV (%) | 26.7 | 26.6 |
| Model | IB | IB |
| Rel Eff | 111 | 123 |
| Czek Coeff .10 | 0.73 | 0.87 |
| Czek Coeff .20 | 0.86 | 0.9 |
| # Environments | 2 | 2 |
| Total Blocks | 8 | 8 |
| p.val (Entry) | 0 | 0 |
| % V | 85.7 | 82.9 |
| % VL | 0.8 | 2.9 |
| % E | 13.5 | 14.1 |
| SED between 2 entry means | 0.658 | 0.637 |
| 2'SED between 2 entry means (LSD) | 1.316 | 1.274 |

Using this method of classification the varieties were grouped according to their reactions to herbicides A and B. For herbicide A there were 32 tolerant, 67 moderate, 37 susceptible and 8 segregating lines. For herbicide B there were 29 tolerant, 75 moderate, 32 susceptible and 8 segregating lines.

An Intergroup Allele Frequency Distribution analysis was conducted using GeneFlow™ version 7.0 software. An intergroup allele frequency distribution analysis provides a method for finding non-random distributions of alleles between two phenotypic groups.

During processing, a contingency table of allele frequencies was constructed and from this a G-statistic and probability were calculated. The G-statistic was adjusted by using the William's correction factor. The probability value was adjusted to take into account the fact that multiple tests are being done (thus, there is some expected rate of false positives). The adjusted probability is proportional to the probability that the observed allele distribution differences between the two classes would occur by chance alone. The lower that probability value, the greater the likelihood that the tolerance phenotype and the marker will co-segregate. A more complete discussion of the derivation of the probability values can be found in the GeneFlow™ version 7.0 software documentation. See also Sokal and Rolf (1981), Biometry: The Principles and Practices of Statistics in Biological Research, 2nd ed., San Francisco, W. H. Freeman and Co.

The underlying logic is that markers with significantly different allele distributions between the tolerant and non-tolerant groups (i.e., non-random distributions) might be associated with the trait and can be used to separate them for purposes of marker assisted selection of soybean lines with previously uncharacterized tolerance or non-tolerance or sensitivity to mesotrione and/or isoxazole herbicides. The present analysis examined one marker locus at a time and determined if the allele distribution within the tolerant group is significantly different from the allele distribution within the non-tolerant group. A statistically different allele distribution is an indication that the marker is linked to a locus that is associated with tolerance or non-tolerance or sensitivity to mesotrione and/or isoxazole herbicides. In this analysis, unadjusted probabilities less than one are considered significant (the marker and the phenotype show linkage disequilibrium), and adjusted probabilities less than approximately 0.05 are considered highly significant. Allele classes represented by less than 5 observations across both groups were not included in the statistical analysis. In this analysis, 1043 marker loci had enough observations for analysis.

This analysis compares the plants' phenotypic score with the genotypes at the various loci. This type of intergroup analysis neither generates nor requires any map data. Subsequently, map data (for example, a composite soybean genetic map) is relevant in that multiple significant markers that are also genetically linked can be considered as collaborating evidence that a given chromosomal region is associated with the trait of interest.

For the herbicide A variety trial, the analysis identified 275 markers (P<0.05), of these 275 markers identified, 243 of the markers had been previously mapped to a particular genomic position. This allowed for further analysis to identify potential genomic regions for genes and to eliminate marker regions that are likely not associated with the native tolerance to the herbicide. There were a total of 6 regions identified where multiple markers were pointing to a particular genomic region (Table 5). The regions identified included regions on B2, D2, E, G, L and 7 unmapped (UM) markers. Of the original 275 markers identified, 112 markers were used to identify the 6 genomic regions.

TABLE 5

Potential genomic regions for Herbicide A

| Linkage group | cM (position) | Markers | Comment |
| --- | --- | --- | --- |
| B2 | 92.2-111.86 | 31 | |
| D2 | 88.11-92.58 | 6 | |
| E | 82.16-100.51 | 37 | |
| G | 78.6-85.82 | 22 | |
| L | 10.1-14.31 | 4 | Highest significance |
| L | 41.09-46.35 | 5 | |
| UM | | 7 | Highly significant < .008 |

A similar analysis was conducted for the tolerant and susceptible classes to Herbicide B where 274 markers were identified (P<0.05). Of the 274 markers identified 239 markers had been previously mapped to a particular genomic position. Similar regions to Herbicide A were identified that included B2, E, G, L, and 10 UM markers (Table 6). A potential region on N was added and the region on D2 was taken off for Herbicide B tolerance. Of the original 274 markers identified 116 markers were used to help identify the 6 regions.

TABLE 6

Potential genomic regions for Herbicide B

| Linkage group | cM (position) | Markers | Comment |
| --- | --- | --- | --- |
| B2 | 92.2-111.86 | 20 | |
| E | 82.16-100.51 | 41 | |
| G | 77.87-85.82 | 17 | |
| L | 10.1-14.31 | 4 | Highest significance |
| L | 41.09-42.17 | 3 | |
| N | 37.11-53.27 | 21 | |
| UM | | 10 | Highly significant < .008 |

Additional observations were made through looking at the tolerant, moderate, susceptible and segregating classes to each herbicide as assigned through the variety trial. Of the 144 varieties in the herbicide trial, 21 were tolerant to both herbicides, 54 displayed moderate tolerance to both herbicides, and 28 displayed susceptible reactions to both herbicides. There were a total of 31 varieties that were classified one class higher or lower to herbicide A or B. For example 11 varieties were tolerant to herbicide A and moderate to herbicide B, where they were lowered 1 class from herbicide A classification to herbicide B classification. There were zero lines that were tolerant to one herbicide and susceptible to the other. This is summarized in Table 7.

TABLE 7

Variety reactions to both herbicides

| | | Herbicide B (mesotrione) | | | |
| --- | --- | --- | --- | --- | --- |
| | Class | Tol | Moderate | Sus | Seg |
| Herbicide A (isoxazole) | Tol | 21 | 11 | 0 | 0 |
| | Moderate | 8 | 54 | 3 | 2 |
| | Sus | 0 | 9 | 28 | 0 |
| | Seg | 0 | 1 | 1 | 6 |

The significant markers were observed for both variety classes to each of the chemistries. Of the 275 and 274 markers that were significant for the Herbicide A and Herbicide B reactions, 144 markers were significant for both variety reactions. As observed in the variety trial analysis, the regions of potential QTLs were observed for both classes on B2, E, G, and L; with the most significant markers on L from 10.1-14.31 cM (Tables 5 and 6).

Table 8 shows the allele distribution for marker S03859, which is closely linked to this region, among the 144 lines analyzed; 32 tolerant lines, 37 non-tolerant (susceptible) lines, 67 moderate, and 8 segregating lines analyzed. Marker calls for the 503859 locus were available for 111 of the 144 lines.

TABLE 8

Allele distribution

| S03859 allele (LG-L) | Phenotype | Adjusted mean |
| --- | --- | --- |
| 1, 1 | Susceptible | 1.6085 |
| 1, 1 | Susceptible | 1.7085 |
| 1, 1 | Susceptible | 1.8675 |
| | Susceptible | 1.9175 |
| 1, 1 | Susceptible | 2.006 |
| 1, 1 | Susceptible | 2.212 |
| | Susceptible | 2.272 |
| | Susceptible | 2.283 |
| 1, 1 | Susceptible | 2.2845 |
| 1, 1 | Susceptible | 2.327 |
| 1, 1 | Susceptible | 2.4255 |
| 1, 1 | Susceptible | 2.643 |
| | Susceptible | 2.6815 |
| 1, 1 | Susceptible | 2.781 |
| 1, 1 | Susceptible | 2.8325 |
| 1, 1 | Susceptible | 2.838 |
| 1, 1 | Susceptible | 2.881 |
| 1, 1 | Susceptible | 2.883 |
| 1, 1 | Susceptible | 2.9005 |
| 1, 1 | Susceptible | 2.927 |
| 1, 1 | Susceptible | 2.992 |
| 1, 1 | Susceptible | 2.994 |
| | Susceptible | 3.056 |
| 1, 1 | Susceptible | 3.1475 |
| 3, 3 | Susceptible | 3.215 |
| 1, 1 | Susceptible | 3.2835 |
| 1, 3 | Susceptible | 3.3085 |
| | Susceptible | 3.3385 |

TABLE 8-continued

Allele distribution

| S03859 allele (LG-L) | Phenotype | Adjusted mean |
|---|---|---|
| 1, 1 | Susceptible | 3.3875 |
| 1, 1 | Susceptible | 3.3885 |
| 1, 1 | Susceptible | 3.4085 |
| 1, 1 | Segregating | 3.5095 |
| 1, 1 | Susceptible | 3.6345 |
| 1, 1 | Susceptible | 3.711 |
| 1, 1 | Susceptible | 3.7595 |
| 1, 3 | Moderate | 3.851 |
|  | Moderate | 3.919 |
|  | Susceptible | 3.9385 |
| 1, 1 | Moderate | 3.967 |
| 3, 3 | Moderate | 4.067 |
|  | Moderate | 4.107 |
| 3, 3 | Susceptible | 4.1605 |
| 1, 1 | Susceptible | 4.1645 |
| 1, 3 | Moderate | 4.17 |
| 3, 3 | Moderate | 4.179 |
| 3, 3 | Moderate | 4.3415 |
| 3, 3 | Moderate | 4.35 |
| 1, 1 | Moderate | 4.357 |
| 3, 3 | Moderate | 4.4295 |
| 3, 3 | Moderate | 4.4495 |
|  | Moderate | 4.4765 |
| 3, 3 | Moderate | 4.524 |
| 1, 1 | Moderate | 4.555 |
|  | Moderate | 4.6375 |
| 3, 3 | Moderate | 4.6615 |
| 3, 3 | Moderate | 4.676 |
| 3, 3 | Moderate | 4.678 |
|  | Segregating | 4.723 |
|  | Moderate | 4.7575 |
| 3, 3 | Segregating | 4.7645 |
| 3, 3 | Moderate | 4.7675 |
|  | Moderate | 4.771 |
|  | Moderate | 4.7875 |
| 3, 3 | Moderate | 4.797 |
| 1, 3 | Moderate | 4.846 |
|  | Tolerant | 4.85 |
|  | Moderate | 4.891 |
| 1, 1 | Moderate | 4.9085 |
| 3, 3 | Moderate | 4.9095 |
| 3, 3 | Moderate | 4.9395 |
| 3, 3 | Tolerant | 4.943 |
| 1, 1 | Moderate | 4.961 |
| 1, 1 | Moderate | 5.015 |
| 3, 3 | Moderate | 5.0195 |
| 3, 3 | Moderate | 5.051 |
| 3, 3 | Moderate | 5.1305 |
|  | Tolerant | 5.1475 |
| 3, 3 | Moderate | 5.1495 |
|  | Moderate | 5.2105 |
| 3, 3 | Tolerant | 5.2125 |
| 3, 3 | Moderate | 5.214 |
| 3, 3 | Tolerant | 5.215 |
| 3, 3 | Moderate | 5.2565 |
| 3, 3 | Moderate | 5.2795 |
| 3, 3 | Moderate | 5.2945 |
| 3, 3 | Moderate | 5.3125 |
| 3, 3 | Moderate | 5.3145 |
| 3, 3 | Moderate | 5.3345 |
| 3, 3 | Moderate | 5.335 |
| 3, 3 | Tolerant | 5.3365 |
|  | Tolerant | 5.377 |
| 3, 3 | Moderate | 5.39 |
| 3, 3 | Segregating | 5.3905 |
| 3, 3 | Segregating | 5.4675 |
| 3, 3 | Moderate | 5.4835 |
| 3, 3 | Segregating | 5.4925 |
| 3, 3 | Moderate | 5.4975 |
| 3, 3 | Tolerant | 5.518 |
| 3, 3 | Moderate | 5.524 |
|  | Segregating | 5.541 |
|  | Tolerant | 5.574 |
| 1, 1 | Moderate | 5.5895 |
| 3, 3 | Moderate | 5.6025 |
|  | Moderate | 5.616 |
| 3, 3 | Tolerant | 5.6685 |
| 3, 3 | Tolerant | 5.6925 |
| 3, 3 | Moderate | 5.7005 |
| 3, 3 | Moderate | 5.7095 |
|  | Tolerant | 5.7165 |
| 3, 3 | Moderate | 5.7315 |
|  | Moderate | 5.741 |
|  | Moderate | 5.75 |
| 3, 3 | Tolerant | 5.7545 |
| 3, 3 | Moderate | 5.7625 |
| 3, 3 | Moderate | 5.7705 |
| 3, 3 | Moderate | 5.7715 |
| 3, 3 | Moderate | 5.7835 |
| 3, 3 | Segregating | 5.7875 |
| 3, 3 | Moderate | 5.798 |
| 3, 3 | Moderate | 5.851 |
| 3, 3 | Moderate | 5.852 |
| 3, 3 | Tolerant | 5.857 |
| 3, 3 | Tolerant | 5.87 |
| 3, 3 | Moderate | 5.8705 |
|  | Tolerant | 5.914 |
|  | Tolerant | 5.948 |
| 3, 3 | Tolerant | 5.9525 |
| 3, 3 | Tolerant | 5.9675 |
|  | Tolerant | 6.0245 |
| 3, 3 | Moderate | 6.026 |
| 3, 3 | Moderate | 6.0275 |
| 3, 3 | Tolerant | 6.034 |
| 3, 3 | Tolerant | 6.042 |
| 3, 3 | Tolerant | 6.054 |
|  | Tolerant | 6.092 |
|  | Tolerant | 6.1295 |
| 3, 3 | Moderate | 6.2395 |
| 3, 3 | Tolerant | 6.2475 |
| 3, 3 | Tolerant | 6.2695 |
|  | Tolerant | 6.275 |
| 3, 3 | Tolerant | 6.387 |
| 3, 3 | Tolerant | 6.431 |
| 3, 3 | Tolerant | 6.6535 |
|  | Tolerant | 6.674 |

The non-random distribution of alleles between the tolerant and non-tolerant plant groups at the marker loci in Table 8 is good evidence that a QTL influencing tolerance or sensitivity to mesotrione and/or isoxazole herbicides is linked to these marker loci.

QTLs related to tolerance and susceptibility to mesotrione and/or isoxazole herbicides were found to essentially co-localize with QTLs related to tolerance to PPO inhibitor herbicides to linkage group L, as shown in the Examples below. Thus, PPO tolerance could be used to fine map the QTL and to identify putative candidate genes as shown below.

Example 3: Identification of Sulfentrazone Tolerant and Sensitive Soybean Lines—Herbicide Screening Bioassay and Intergroup Association Marker Based Diagnostic Sulfentrazone is a PPO inhibitor and is the active ingredient in Authority® herbicide. Authority® 75DF (FMC Corp., Philadelphia, Pa., USA) is a 75% active ingredient formulation of sulfentrazone containing no other active ingredients.

Part 1: Herbicide Bioassay

One hundred sixteen (116) elite soybean lines were screened for sulfentrazone tolerance using the following protocol. Seed of soybean varieties with adequate seed quality, having greater than 85% warm germination were used.

Design and Replication:

After planting, entries were set up in a randomized complete block design, blocked by replication. Three replications per experiment were used. One or more of well established check variety were included in the experiment, such as available public sector check lines.

Non-tolerant check: Pioneer 9692, Asgrow A4715
Tolerant check: Pioneer 9584, Syngenta 55960

Growing conditions were as follows (greenhouse/growth chamber): 16 hr photoperiod @ 85° F. (w/75° nighttime set back). Lighting is critical to the success of the screening as stated below.

Method of Screening:

Four inch plastic pots were filled with a high quality universal potting soil. Entries were planted 1 inch deep at the rate of 5 seeds/pot. A bar-coded plastic stake was used to identify each entry. After planting the pots were allowed to sit in greenhouse overnight to acclimate to soil and improve germination. The following day a sulfentrazone herbicide solution was slowly poured over each pot and allowed to evenly soak through entire soil profile. This ensured that each seed was exposed to an equal amount of sulfentrazone. Pots were placed on aluminum trays and placed in a greenhouse or growth chamber under high intensity light conditions with photosynthetic photon flux density (PPFD) of at least 500 mol/m/s. Proper lighting conditions were necessary for this screening due to the nature of the PPO inhibitor used. Pots were lightly watered so that herbicide was not leached from the soil profile. After soybean emergence the pots were watered by keeping aluminum trays filled with ¾" of water under each pot.

Herbicide Solution:

A) Mix a stock solution of 0.926 g Authority® 75DF (FMC Corp.), thoroughly dissolved in 1000 ml of water.
B) Mix 10 ml of STOCK SOLUTION in 1000 ml of water to create final solution.
C) Pour 100 ml of FINAL SOLUTION over each pot.

Recording Data:

10-14 days after treatment, plants were ready to be scored. All scores were based on a comparison to the checks and evaluated as follows:

9=Equivalent or better when compared to the tolerant check
7=Very little damage or response noted.
5=Intermediate response or damage
3=Major damage, including stunting and foliar necrosis
1=Severe damage, including severe stunting and necrosis; equivalent or worse when compared to the non-tolerant check Of the 116 soybean lines screened, 102 showed at least some tolerance to sulfentrazone based herbicides and 11 showed high sensitivity. A reference relevant to this protocol would be: Dayan et al. (1997) 'Soybean (*Glycine max*) cultivar differences in response to sulfentrazone' Weed Science 45:634-641.

Part 2: Intergroup Analysis

An "Intergroup Allele Frequency Distribution" analysis was conducted using GeneFlow™ version 7.0 software as described above. An intergroup allele frequency distribution analysis provides a method for finding non-random distributions of alleles between two phenotypic groups.

During processing, a contingency table of allele frequencies was constructed and from this a G-statistic and probability were calculated. The G statistic was adjusted by using the William's correction factor. The probability value was adjusted to take into account the fact that multiple tests are being done (thus, there is some expected rate of false positives). The adjusted probability is proportional to the probability that the observed allele distribution differences between the two classes would occur by chance alone. The lower that probability value, the greater the likelihood that the tolerance phenotype and the marker will co-segregate. A more complete discussion of the derivation of the probability values can be found in the GeneFlow™ version 7.0 software documentation. See also Sokal and Rolf (1981), Biometry: The Principles and Practices of Statistics in Biological Research, 2nd ed., San Francisco, W. H. Freeman and Co.

The underlying logic is that markers with significantly different allele distributions between the tolerant and non-tolerant groups (i.e., non-random distributions) might be associated with the trait and can be used to separate them for purposes of marker assisted selection of soybean lines with previously uncharacterized tolerance or non-tolerance to protoporphyrinogen oxidase inhibitors. The present analysis examined one marker locus at a time and determined if the allele distribution within the tolerant group is significantly different from the allele distribution within the non-tolerant group. A statistically different allele distribution is an indication that the marker is linked to a locus that is associated with tolerance or non-tolerance to protoporphyrinogen oxidase inhibitors. In this analysis, unadjusted probabilities less than one are considered significant (the marker and the phenotype show linkage disequilibrium), and adjusted probabilities less than approximately 0.05 are considered highly significant. Allele classes represented by less than 5 observations across both groups were not included in the statistical analysis. In this analysis, 1043 marker loci had enough observations for analysis.

This analysis compares the plants' phenotypic score with the genotypes at the various loci. This type of intergroup analysis neither generates nor requires any map data. Subsequently, map data (for example, a composite soybean genetic map) is relevant in that multiple significant markers that are also genetically linked can be considered as collaborating evidence that a given chromosomal region is associated with the trait of interest.

Results:

Table 9 lists the soybean markers that demonstrated linkage disequilibrium with the tolerance to protoporphyrinogen oxidase inhibitor phenotype. There were 1043 markers used in this analysis. Also indicated in that table are the chromosomes on which the markers are located and their approximate map position relative to other known markers, given in cM, with position zero being the first (most distal) marker known at the beginning of the chromosome. These map positions are not absolute, and represent an estimate of map position. The statistical probabilities that the marker allele and tolerance phenotype are segregating independently are reflected in the Adjusted Probability values. Out of 584 loci studied in 38 sensitive and 160 tolerant soybean lines, QTLs on Lg-L were highly significant, as shown in the table below.

TABLE 9

Intergroup analysis results for Lg-L markers

| Locus | Test | Linkage Group | Position | G-value | df | Prob(G) | Adj Prob |
|---|---|---|---|---|---|---|---|
| S00224-1 | GW | L | 12.03 | 89.87 | −1 | 0 | 0 |
| P10649C-3 | ASH | L | 3.6 | 86.01 | −1 | 0 | 0 |
| SATT523 | SSR | L | 32.4 | 24.02 | −1 | 0.000001 | 0.000592 |

Table 10 shows the allele distribution between 101 tolerant lines and 32/33 non-tolerant lines analyzed. Lines exhibiting tolerance are indicated in the first column as "TOL," and lines exhibiting non-tolerance are indicated in the first column as "NON." Marker calls for the P10649C-3 locus and the S60167-TB locus were available for 132 and 63 of the lines respectively.

TABLE 10

| Allele distribution | |
|---|---|
| Phenotype | P10649C-3 allele LG-L |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | |
| TOL | 1 |
| TOL | 1 |
| TOL | 2 |
| TOL | 1 |
| TOL | 1 |
| TOL | 1 |
| NON | 3 |
| NON | 3 |
| NON | 1 |
| NON | 1_2 |
| NON | 3 |
| NON | 3 |
| NON | 1 |
| NON | 3 |
| NON | 2 |
| NON | 3 |
| NON | 2 |
| NON | 2 |
| NON | 2 |
| NON | 1 |
| NON | 2_3 |
| NON | 3 |
| NON | 3 |
| NON | 2_3 |
| NON | 3 |
| NON | 3 |
| NON | 1 |
| NON | 2 |
| NON | 3 |
| NON | 3 |
| NON | 3 |
| NON | 2 |
| NON | 3 |
| NON | 1_3 |
| NON | 3 |
| NON | 2 |
| NON | 1 |
| NON | 3 |

The non-random distribution of alleles between the tolerant and non-tolerant plant groups at the marker loci in Table 10 is good evidence that a QTL influencing tolerance to protoporphyrinogen oxidase inhibitors is linked to these marker loci.

Example 4: Predication and Confirmation of Marker Based Selection for Response to PPO Chemistries in a Set of Diverse Public Soybean Lines Marker haplotype data for a set of 17 diverse public soybean lines was determined for two QTL identified in Example 3 for Linkage Group L molecular markers P10649C-3 (approximate position 3.6) and S00224-1 (approximate position 12.0). The response of these lines to sulfentrazone herbicide was published by Hulting et al. (Soybean (*Glycine max* (L.) Merr.) cultivar tolerance to sulfentrazone. 2001 Science Direct, Vol. 20(8): 679-683). The phenotypic response was reported as a growth reduction index: plant height and visual injury as expressed as a percentage of check plot of each cultivar. Data for the marker haplotype on Linkage Group L and the herbicide bioassay results are presented in Table 11. Use of the molecular diagnostic P10649C-3 (linked QTL on Linkage Group L, approximate position 3.6) for this set of phentoyped soybean lines is 92% predictive of tolerance to sulfentrazone when injury is set at 39% or less GRI and is 100% predictive of non-tolerance to sulfentrazone when injury is set at 40% or higher GRI. Use of the S00224-1 marker (approximate position 12.0) for this set of soybean lines is 88% predictive of tolerance to sulfentrazone when injury is set at 39% or less GRI and is 100% predictive of non-tolerance to sulfentrazone when injury is set at 40% or more GRI.

TABLE 11

Marker haplotype at/near QTL on Linkage Group L for PPO herbicide (sulfentrazone) response and phenotypic measure of crop response, expressed in terms of Growth Reduction Index, for soybean cultivars (italicized items indicate deviations from expected)

| Cultivar | Growth Reduction Index* | Linkage Group L QTLs Position 3.6 P10649C-3 | Position 12.0 S00224-1 |
|---|---|---|---|
| PI88788 | 2 | 1, 1 | 3, 3 |
| Richland | 4 | 1, 1 | 3, 3 |
| Lincoln | 5 | 1, 1 | 3, 3 |
| PI180501 | 8 | 1, 1 | 3, 3 |
| Illini | 8 | 1, 1 | 3, 3 |
| S100 | 8 | 1, 1 | 3, 3 |
| Mukden | 8 | 1, 1 | 3, 3 |
| Arksoy | 10 | 1, 1 | 3, 3 |
| Capital | 10 | 1, 1 | 3, 3 |
| Haberlandt | 10 | *3, 3* | *2, 2* |
| Ralsoy | 13 | 1, 1 | *2, 3* |
| Dunfield | 16 | 1, 1 | 3, 3 |
| Peking | 22 | 1, 1 | 3, 3 |
| Roanoke | 40 | 3, 3 | 2, 2 |
| Ogden | 42 | 3, 3 | 2, 2 |
| Hutcheson | 46 | 3, 3 | 2, 2 |
| Ransom | 52 | 3, 3 | 2, 2 |

| allele call load percent accuracy | | | |
|---|---|---|---|
| correct tolerant | (alleles 1) 24/26 = 92% | (allele 3) 23/26 = 88% | |
| correct non-tolerant | (allele 3) 8/8 = 100% | (allele 2) = 8/8 = 100% | |

*growth reduction index (plant height and visual injury as expressed as a percentage of check plot of each cultivar); Pre-emergence sulfentrazone application of 0.28 kg ai/ha, from Hulting, et al. (supra)

Example 5: Predication and Confirmation of Marker Based Selection for Response to PPO Chemistries in a Set of Soybean Commercial Lines Haplotype data for a set of 7 commercial soybean lines was determined for two QTL identified in the previous example for Linkage Group L molecular markers P10649C-3 (position 3.6) and S00224-1 (position 12.0). The response of these lines to sulfentrazone herbicide was determined by method used in Example 3. In addition, the same scale was used for scoring such that:

9=Equivalent or better when compared to the tolerant check
7=Very little damage or response noted.
5=Intermediate response or damage
3=Major damage, including stunting and foliar necrosis
1=Severe damage, including severe stunting and necrosis; equivalent or worse when compared to the non-tolerant check Data for the marker haplotype on Linkage Group L and the herbicide bioassay results are presented in Table 12. Use of either/both of these markers for this set of phentoyped soybean lines is 100% predictive of both tolerance (score of a 7 or 9) and non-tolerance (score of a 1 for the non-tolerant check).

TABLE 12

Prediction and confirmation of marker based selection at QTL for linkage group L for response to PPO chemistry (sulfentrazone) in a set of commercial soybean varieties.

| Variety | sulfentrazone injury score | Position 3.6 P10649C-3 | Position 12.0 S00224-1 |
|---|---|---|---|
| 93B41 | 9 | 1, 1 | 3, 3 |
| 93B82 | 9 | 1, 1 | 3, 3 |
| 9281 | 9 | 1, 1 | 3, 3 |
| 9584 | 9 | 1, 1 | 3, 3 |
| 92B52 | 7 | 1, 1 | 3, 3 |
| 92B61 | 7 | 1, 1 | 3, 3 |
| 9692 | 1 | 3, 3 | 2, 2 |

Example 6: Predication and Confirmation of Marker Based Selection for Response to PPO Chemistries (Sulfentrazone) in Ten Lines from a Set of Soybean Lines Phenotyped at the University of Illinois A comparison for the marker predictiveness of PPO response was conducted. The herbicide bioassay experiment used is described in Phytoxic Response and Yield of Soybean (*Glycine max*) Varieties Treated with Sulfentrazone or Flumioxazin (Taylor-Lovell et al., 2001 Weed Technology 15:96-102). Phenotypic data was taken from Table 2 of the publication for those varieties for which in-house marker data was available. Phenotypic score and haplotype data for a set of 10 soybean lines (1 public and 9 commercial) in the chromosomal regions around the QTL for Linkage group L is presented in Table 13. The phenotypic score was determined as percent injury which is defined as visible injury ratings including stunting, chlorosis, and bronzing symptomology (0=no injury; 100=complete death) with 448 g ai/ha field application. Ratings were taken 12 days after treatment. Use of marker P10649C (linked QTL on Linkage Group L, approximate position 3.6, allele call 1) for this set of phentoyped soybean lines is 100% predictive of tolerance (allele call 1) to sulfentrazone when injury is 21% or less and is 100% predictive of non-tolerance (allele call 2 or 3) to sulfentrazone when injury is 43% or greater. The predictiveness of marker S00224-1 is also 100% accurate for tolerance (allele 3) and non-tolerance (allele 2) for this set of material.

TABLE 13

Marker haplotype at/near QTL on Linkage Group L for PPO herbicide (sulfentrazone) response and phenotypic measure of crop injury

| Variety | sulfentrazone injury score | Position 3.6 P10649C-3 | Position 12.0 S00224-1 |
|---|---|---|---|
| P9584 | 5 | 1, 1 | 3, 3 |
| P9671 | 5 | 1, 1 | 3, 3 |
| P9151 | 8 | 1, 1 | 3, 3 |
| P9306 | 15 | 1, 1 | 3, 3 |
| Elgin | 18 | 1, 1 | 3, 3 |
| P9282 | 19 | 1, 1 | 3, 3 |
| P9352 | 21 | 1, 1 | 3, 3 |
| P9362 | 43 | 2, 2 | 2, 2 |
| 91B01 | 58 | 3, 3 | 2, 2 |
| P9552 | 61 | 3, 3 | 2, 2 |
| LSD (0.05) | 8 | | |

| | allele call load percent accuracy | |
|---|---|---|
| correct tolerant | (alleles 1 or 2) 14/14 = 100% | (allele 3) 14/14 = 100% |
| correct non-tolerant | (allele 3) 8/8 = 100% | (allele 2) = 8/8 = 100% |

Example 7: Fine Mapping of the LG-L Herbicide Tolerance QTL

The herbicide tolerance QTL on LG-L was initially mapped in two different soybean mapping populations: GEID1653063×GEID3495695 (F4-derived F6) and GEID4520632×GEID7589905 (F3-derived F5). From these populations, 184 and 180 lines respectively were genotyped and scored for PPO herbicide tolerance as described above. This data was used to map the herbicide tolerance QTL to chromosome GM19 near the closely linked marker S03859-1-A, which explains 80% of the phenotypic variation. From these two populations, lines with recombination breakpoints near S03859-1-A were identified to define the borders of the QTL and to facilitate fine-mapping.

Subsequent analysis of the recombinants indicated that the closely linked marker S03859-1-A was actually the left flanking marker. The GEID1653063×GEID3495695 population had 37 recombinants that set the flanking markers for the herbicide tolerance QTL as S04867-1-A (GM19: 841543-841958) and S03859-1-A (GM19: 1634882-1635399) (Table 17). The GEID4520632×GEID7589905 population had 42 recombinants that delimit the QTL to the same interval (Table 18).

Because S03859-1-A was determined to be closely linked to the herbicide tolerance QTL, annotated loci in the vicinity of this marker were targeted for SNP discovery and marker development. Primers were designed from target loci using Primer3 (open source software available from SourceForge.net) and checked for uniqueness using bioinformatics software. A panel composed of 20 PPO tolerant and 8 PPO susceptible lines, including the four mapping parents from the mapping population, was re-sequenced at the target loci to identify informative SNPs. DNA was extracted using the urea extraction protocol below and PCR amplified using standard lab protocols (see Tables 14-15). The PCR was then cleaned up using the ExoSAP-IT® protocol (USB-Cleveland, Ohio, USA) (Table 15) before being sequenced by Sanger sequencing.

In total, 104 loci were re-sequenced and 235 informative SNPs were identified. From these SNPs, 22 Taqman® probe markers were designed to distinguish between tolerant versus susceptible alleles in the mapping populations. Taqman® assays were designed generally following ABI suggested parameters. These markers were then run on 86 select recombinants combined from the two mapping populations to facilitate fine-mapping and to further delimit the herbicide tolerance QTL interval (Table 19).

Urea Extraction Protocol

1. Grind 2 g fresh tissue or .5 g lyophilized tissue and add it to 6 mL Urea Extraction Buffer and mix well.
2. Add RNase A (100 mg/mL) and incubate @ 37° C. for 20 min.
    a. 3 uL - Leaf
    b. 12 uL - Seed
3. Add 4-5 mL Phenol:Chloroform:Isoamyl 25:24:1. Mix well. (Sigma P3803)
4. Put on rocker inside hood.
    a. Fresh - 15 min
    b. Lyophilized - 30 min
5. Centrifuge @ 8000 rpm at 10° C. for 10 min.
6. Transfer supernatant to clean tube.
7. Add 700 uL of 3M NaOAC (pH 5.0) and 5 mL cold isopropanol. Mix well.
8. Hook DNA and wash in 70% EtOH.
9. Repeat 70% wash.
10. Transfer pellet to 1.5 mL tube and allow to dry.
11. Dissolve pellet in 1 mL 10 mM Tris.

7M Urea Extraction Buffer

| | |
|---|---|
| Water | 350 mL |
| Urea | 336 g |
| 5M NaCl | 50 mL (14.61 g) |
| 1M Tris | 40 mL (pH 8.0) |
| .5M EDTA | 32 mL (pH 8.0) |
| 20% Sarcosine Sol. | 40 mL (8 g) |
| Adjust volume to 800 mL with ddH2O | |

TABLE 14

PCR Reaction Mix for SNP Discovery

| | 1X (uL) | 24 plate (ul) | 36 plate (uL) | 48 plate (uL) |
|---|---|---|---|---|
| gDNA (~50-100 ng) | 2.0 | — | — | — |
| 10x PCR Buffer | 2.0 | 5,952 | 7,680 | 10,944 |
| 1 mM dNTP | 2.0 | 5,952 | 7,680 | 10,944 |
| Taq | 0.1 | 297.6 | 384 | 547.2 |
| 0.5 uM Primer (F + R) | 4.0 | — | — | — |
| ddH2O | 9.9 | 29,462 | 38,016 | 54,173 |
| Total | 20.0 | 41,664 | 53,760 | 76,608 |

TABLE 15

PCR Setup for SNP Discovery

Dipper Setup

| PCR conditions | Temp | Time | #Cycles |
|---|---|---|---|
| initial denature | 94 C. | 3 min | 1X |
| denature | 94 C. | 45 sec | 35X |
| anneal | 65 C. | 60 sec | |
| extension | 72 C. | 75 sec | |
| final extension end | 72 C. | 5 min | 1X |

TABLE 16

Protocol for PCR clean up
PCR clean up Exo/SAP Mix (pre-sequencing)
add 3.6 ul of mastermix to 7 μl final PCR product

|  | 24 plate (μl) | 36 plate (μl) | 48 plate (μl) |
|---|---|---|---|
| ddH2O | 4,285.4 | 5,944.3 | 7,326.7 |
| SAP | 4,285.4 | 5,944.3 | 7,326.7 |
| Exo | 2,142.7 | 2,972.2 | 3,663.4 |
| total | 10,714 | 14,861 | 18,317 |

TABLE 17

Initial recombinants identified from GEID1653063 × GEID3495695 mapping population that delimited herbicide tolerance QTL to interval between S04867-1-A and S03859-1-A

| SAMPLE | S04867-1-A | S03859-1-A | Call | Average | Comment |
|---|---|---|---|---|---|
| Genetic Pos | 7.81 | 10.00 | | | |
| GEID1653063 | A | A | SUS | 1 | Control |
| GEID3495695 | B | B | TOL | 9 | Control |
| SJ22185567 | A | B | TOL | 9 | L border |
| SJ22185980 | A | B | TOL | 9 | L border |
| SJ22186045 | A | B | TOL | 9 | L border |
| SJ22186929 | A | B | TOL | 9 | L border |
| SJ22186019 | B | H | TOL | 9 | R border |
| SJ22185608 | H | B | TOL | 9 | L border |
| SJ22186913 | H | B | TOL | 9 | L border |
| SJ22185928 | H | B | TOL | 9 | L border |
| SJ22186923 | H | B | TOL | 8.333333 | L border |
| SJ22185569 | A | H | SEG | 5 | L border |
| SJ22186052 | A | H | SEG | 6.333333 | L border |
| SJ22186882 | A | H | SEG | 5 | L border |
| SJ22186919 | B | H | SEG | 5.666667 | L border |
| SJ22186968 | B | H | SEG | 6.333333 | L border |
| SJ22186824 | B | H | SEG | 6.333333 | L border |
| SJ22185604 | H | B | SEG | 6.333333 | R border |
| SJ22185573 | H | A | SEG? | 3.666667 | R border |
| SJ22185983 | A | B | SUS | 1 | R border |
| SJ22186894 | A | B | SUS | 2.333333 | R border |
| SJ22185562 | A | H | SUS | 1.666667 | R border |
| SJ22185941 | A | H | SUS | 1 | R border |
| SJ22185534 | B | A | SUS | 3 | L border |
| SJ22185545 | B | A | SUS | 1.666667 | L border |
| SJ22185559 | B | A | SUS | 2.333333 | L border |
| SJ22186023 | B | A | SUS | 3 | L border |
| SJ22186057 | B | A | SUS | 1 | L border |
| SJ22186065 | B | A | SUS | 1 | L border |
| SJ22186837 | B | A | SUS | 3 | L border |
| SJ22185957 | B | A | SUS | 1 | L border |
| SJ22186846 | B | A | SUS | 1.666667 | L border |
| SJ22186840 | H | A | SUS | 1 | L border |
| SJ22186950 | H | A | SUS | 1 | L border |
| SJ22186872 | H | A | SUS | 2.333333 | L border |
| SJ22186836 | H | A | SUS | 1.666667 | L border |
| SJ22186074 | H | A | SUS | 1 | L border |
| SJ22186906 | H | A | SUS | 1 | L border |
| SJ22185984 | H | A | SUS | 1 | L border |

TABLE 18

Initial recombinants identified from GEID4520632 × GEID7589905 mapping population that delimited herbicide tolerance QTL to interval between S04867-1-A and S03859-1-A

| SAMPLE | S04867-1-A | S03859-1-A | Call | Average | Comment |
|---|---|---|---|---|---|
| Genetic Pos | 7.81 | 10.00 | | | |
| GEID7589905 | A | A | SUS | 1 | Control |
| GEID4520632 | B | B | TOL | 9 | Control |
| SP21669231 | A | B | TOL | 9 | L border |

TABLE 18-continued

Initial recombinants identified from GEID4520632 × GEID7589905 mapping population that delimited herbicide tolerance QTL to interval between S04867-1-A and S03859-1-A

| SAMPLE | S04867-1-A | S03859-1-A | Call | Average | Comment |
|---|---|---|---|---|---|
| SP21669401 | A | B | TOL | 9 | L border |
| SP21669240 | A | B | TOL | 9 | L border |
| SP21669613 | A | B | TOL | 9 | L border |
| SP21669249 | H | B | TOL | 9 | L border |
| SP21669645 | H | B | TOL | 9 | L border |
| SP21669670 | H | B | TOL | 9 | L border |
| SP21669563 | H | B | TOL | 9 | L border |
| SP21669592 | H | B | TOL | 9 | L border |
| SP21669260 | B | A | SUS | 1 | L border |
| SP21669265 | B | A | SUS | 1 | L border |
| SP21669778 | B | A | SUS | 1.666667 | L border |
| SP21669590 | B | A | SUS | 1 | L border |
| SP21669751 | A | H | SUS | 1 | R border |
| SP21669380 | H | A | SUS | 2.666667 | L border |
| SP21669679 | H | A | SUS | 1 | L border |
| SP21669708 | H | A | SUS | 1 | L border |
| SP21669755 | H | A | SUS | 1 | L border |
| SP21669214 | H | A | SUS | 1 | L border |
| SP21669573 | H | A | SUS | 1.666667 | L border |
| SP21669612 | H | A | SUS | 2.333333 | L border |
| SP21669336 | H | A | SUS | 3.666667 | L border |
| SP21669201 | B | H | SEG | 5 | L border |
| SP21669503 | B | H | SEG | 5 | L border |
| SP21669664 | B | H | SEG | 5 | L border |
| SP21669540 | B | H | SEG | 5 | L border |
| SP21669752 | B | H | SEG | 5.666667 | L border |
| SP21669230 | B | H | SEG | 5.666667 | L border |
| SP21669331 | A | H | SEG | 6.333333 | L border |
| SP21669371 | A | H | SEG | 5 | L border |
| SP21669542 | A | H | SEG | 6.333333 | L border |
| SP21669584 | A | H | SEG | 5 | L border |
| SP21669694 | A | H | SEG | 5.666667 | L border |
| SP21669763 | A | H | SEG | 5 | L border |
| SP21669533 | A | H | SEG | 5 | L border |
| SP21669417 | A | H | SEG | 6.333333 | L border |
| SP21669647 | A | H | SEG? | 7.666667 | L border |
| SP21669651 | A | H | SEG? | 7.666667 | L border |
| SP21669541 | H | B | SEG? | 7.666667 | R border |
| SP21669749 | H | A | SEG | 5 | R border |
| SP21669356 | H | A | SEG | 5 | R border |
| SP21669674 | H | A | SEG? | 3.666667 | R border |

In an initial analysis of the GEID1653063×GEID3495695 mapping population, four key recombinants were identified which served to further fine-map the herbicide tolerance QTL interval (Table 20). A recombination breakpoint at S08110-1-Q1 in line 5J22186052 set the left border, while breakpoints at S08105-1-Q1 in SJ22186019, SJ22186894, and SJ22185941 set the right border. These recombinants delimit the herbicide tolerance QTL to an ~70 kb interval. Initial analysis of the GEID4520632×GEID7589905 mapping population identified eight key recombinants (Table 13). A recombination breakpoint in line SP21669503 at S08117-1-Q1 set the left border, while breakpoints in SP21669249, SP21669332, SP21669615, SP21669616, SP21669670, SP21669458, and SP21669760 set the right border at S08010-1-Q1. These recombinants delimit the herbicide tolerance QTL to a ~526 kb interval. However, when the data from these two mapping populations are combined into a single set, the herbicide tolerance QTL interval was delimited to a ~56 kb interval between S08117-1-Q1 and S08105-1-Q1 (Table 19 and Table 20).

To facilitate higher resolution mapping of the herbicide tolerance QTL interval, lines from the initial set of 86 recombinants were re-scored for herbicide tolerance to confirm their phenotype. Moreover, new markers were developed and used to genotype these recombinants. Consequently, this further analysis resulted in the identification of a key recombinant (SP21669417) from the GEID4520632× GEID7589905 mapping population which set the left border of the herbicide tolerance QTL interval at S08113-1-Q1 (Table 13). In summary, key recombinants from the two mapping populations, scored in two fine-mapping experiments, define the herbicide tolerance QTL to a ~44 kb interval between S08113-1-Q1 and S08105-1-Q1 (Table 19 and Table 20).

TABLE 19

Summary of SNP markers used for initial QTL mapping and fine-mapping of herbicide tolerance QTL. Combined data from the two populations delimits the QTL to a ~44 kb interval between S08113-1-Q1 and S8105-1-Q1

| Marker | Amplicon | Loci | First Base Coordinate | Last base coordinate | Population | Fine-mapping | Comment |
| --- | --- | --- | --- | --- | --- | --- | --- |
| S04867-1-A | | Glyma19g01220.1 | 841543 | 841958 | Both | | |
| S08102-1-Q1 | PPO_Gm19_1487k3-1 | Glyma19g01860.1 | 1489113 | 1489545 | Both | | |
| S08103-1-Q1 | PPO_Gm19_1491k1-1 | X | 1491603 | 1492136 | Both | | |
| S08104-1-Q1 | PPO_Gm19_1491k2-1 | Glyma19g01870.1 | 1492364 | 1492948 | Both | | |
| S08106-1-Q1 | PPO_Gm19_1499k2-1 | Glyma19g01880.1 | 1500732 | 1501392 | A | | |
| S08107-1-Q1 | PPO_Gm19_1541k3-1 | Glyma19g01900.1 | 1542880 | 1543693 | A | | |
| S08109-1-Q1 | PPO_Gm19_1541k4-1 | Glyma19g01900.1 | 1543868 | 1544588 | A | | |
| S08110-1-Q1 | PPO_Gm19_1548k1-1 | Glyma19g01910.1 | 1548367 | 1548822 | A | L border Pop A | |
| S08111-1-Q1 | PPO_Gm19_1548k2-1 | Glyma19g01910.1 | 1548902 | 1549558 | A | | |
| S08115-2-Q1 | PPO_Gm19_1563k1-1 | X | 1563958 | 1564512 | Both | | |
| S08117-1-Q1 | PPO_Gm19_1563k2-1 | X | 1564563 | 1564960 | Both | L border Pop B | |
| S08119-1-Q1 | PPO_Gm19_1566k2-1 | Glyma19g01920.1 | 1567791 | 1568282 | Both | | histone deacetylase |
| S08118-1-Q1 | PPO_Gm19_1566k4-1 | Glyma19g01920.1 | 1569273 | 1569748 | Both | | histone deacetylase |
| S08116-1-Q1 | PPO_Gm19_1566k5-1 | Glyma19g01920.1 | 1570198 | 1570729 | Both | | histone deacetylase |
| S08101-1-Q1 | PPO_Gm19_1586k1-1 | Glyma19g01940.1 | 1587051 | 1587687 | Both | | multidrug/pheromone exporter, ABC superfamily |
| S08112-1-Q1 | PPO_Gm19_1586k1-1 | Glyma19g01940.1 | 1587051 | 1587687 | Both | | multidrug/pheromone exporter, ABC superfamily |
| S08108-1-Q1 | PPO_Gm19_1586k2-1 | Glyma19g01940.1 | 1587805 | 1588500 | Both | | multidrug/pheromone exporter, ABC superfamily |
| S08101-1-Q1 | PPO_Gm19_1586k4-1 | Glyma19g01940.1 | 1589409 | 1590062 | Both | | multidrug/pheromone exporter, ABC superfamily |
| S08101-2-Q1 | PPO_Gm19_1586k4-1 | Glyma19g01940.1 | 1589409 | 1590062 | Both | | multidrug/pheromone exporter, ABC superfamily |
| S08101-3-Q1 | PPO_Gm19_1586k4-1 | Glyma19g01940.1 | 1589409 | 1590062 | Both | | multidrug/pheromone exporter, ABC superfamily |
| S08101-4-Q1 | PPO_Gm19_1586k4-1 | Glyma19g01940.1 | 1589409 | 1590062 | Both | | multidrug/pheromone exporter, ABC superfamily |
| S08105-1-Q1 | PPO_Gm19_1618k2-1 | X | 1619657 | 1620279 | Both | R border Pop A | |
| S03859-1-A | sbacm.pk005.c3.f | X | 1634882 | 1635399 | Both | | |
| S08010-1-Q1 | PPO_Gm19_2089k4-1 | Glyma19g02370.1 | 2091644 | 2092359 | Both | R border Pop B | |
| S08010-2-Q2 | PPO_Gm19_2089k4-1 | Glyma19g02370.1 | 2091644 | 2092359 | Both | | |

*Population A = GEID1653063/GEID3495695; Population B = GEID4520632/GEID7589905

Tables 20A-20H. Fine-Mapping of the Herbicide Tolerance QTL Interval with Recombinants from the GEID1653063× GEID3495695 Population. Key Recombinants Delimit the QTL to the ~70 kb Interval Between S08110-1-Q1 and S08105-1-Q1.

TABLE 20A

| Marker | S04867-1-A | S08102-1-Q1 | S08103-1-Q1 | S08104-1-Q1 |
|---|---|---|---|---|
| Amplicon/Pos | Gm19:841750 | PPO_Gm19_1487k3-1 | PPO_Gm19_1491k1-1 | PPO_Gm19_1491k2-1 |
| Sample | | | | |
| SJ22185925 | B | B | B | B |
| SJ22186974 | B | B | B | B |
| SJ22185946 | B | B | B | B |
| SJ22186019 | B | B | B | B |
| SJ22186923 | H | H | H | H |
| SJ22185604 | H | H | H | H |
| SJ22186029 | H | H | H | H |
| SJ22186052 | A | A | A | A |
| SJ22185534 | B | A | A | A |
| SJ22185552 | A | A | A | A |
| SJ22186842 | A | A | — | A |
| SJ22186924 | A | A | A | A |
| SJ22186873 | A | A | A | A |
| SJ22186894 | A | A | A | A |
| SJ22185957 | B | A | A | A |
| SJ22185941 | A | A | A | A |
| SJ22186872 | H | A | A | A |
| SJ22185984 | H | H | H | H |
| SJ22186045 | — | — | H | H |
| SJ22186913 | — | — | H | H |
| SJ22186891 | — | — | H | H |
| SJ22186879 | — | — | H | H |
| SJ22186841 | — | — | H | H |
| SJ22186057 | — | — | H | H |
| SJ22186065 | — | — | H | H |
| SJ22186951 | — | — | H | H |
| SJ22186840 | — | — | H | H |
| SJ22186070 | — | — | A | A |

TABLE 20B

| Marker | S08106-1-Q1 | S08107-1-Q1 | S08109-1-Q1 | S08110-1-Q1 |
|---|---|---|---|---|
| Amplicon/Pos | PPO_Gm19_1499k2-1 | PPO_Gm19_1541k3-1 | PPO_Gm19_1541k4-1 | PPO_Gm19_1548k1-1 |
| Sample | | | | |
| SJ22185925 | B2 | B | B | B |
| SJ22186974 | B1 | B | B | B |
| SJ22185946 | B2 | B | B | B |
| SJ22186019 | B2 | B | B | B |
| SJ22186923 | H | B | — | B |
| SJ22185604 | H | H | H | H |
| SJ22186029 | H | H | H | H |
| SJ22186052 | A | A | A | A |
| SJ22185534 | A | A | A | A |
| SJ22185552 | A | A | A | A |
| SJ22186842 | A | A | A | A |
| SJ22186924 | A | A | A | A |
| SJ22186873 | A | A | A | A |
| SJ22186894 | H | A | A | A |
| SJ22185957 | A | A | A | A |
| SJ22185941 | A | A | A | A |
| SJ22186872 | A | A | A | A |
| SJ22185984 | H | A | A | A |
| SJ22186045 | H | — | — | H |
| SJ22186913 | H | — | — | B |
| SJ22186891 | H | — | — | H |
| SJ22186879 | H | — | — | H |
| SJ22186841 | H | — | — | H |
| SJ22186057 | H | — | — | H |
| SJ22186065 | H | — | — | H |
| SJ22186951 | H | — | — | H |
| SJ22186840 | H | — | — | A |
| SJ22186070 | A | — | — | A |

TABLE 20C

| Marker | S08111-1-Q1 | S08115-2-Q1 | S08117-1-Q1 | S08119-1-Q1 |
|---|---|---|---|---|
| Amplicon/Pos | PPO_Gm19_1548k2-1 | PPO_Gm19_1563k1-1 | PPO_Gm19_1563k2-1 | PPO_Gm19_1566k2-1 |
| Sample | | | | |
| SJ22185925 | B | B | B | B |
| SJ22186974 | B | B/H | B | B |
| SJ22185946 | B | B | B | B |
| SJ22186019 | B | B | B | B |
| SJ22186923 | B | B | B | B |
| SJ22185604 | H | H | H | H |
| SJ22186029 | H | H | H | H |
| SJ22186052 | — | H | H | H |
| SJ22185534 | A | A | A | A |
| SJ22185552 | A | A | A | A |
| SJ22186842 | A | A | A | A |
| SJ22186924 | A | A | A | A |
| SJ22186873 | A | A | A | A |
| SJ22186894 | A | A | A | A |
| SJ22185957 | A | A | A | — |
| SJ22185941 | A | A | A | A |
| SJ22186872 | A | A | A | — |
| SJ22185984 | A | A | A | A |
| SJ22186045 | H | B | B | B |
| SJ22186913 | B | B | B | B |
| SJ22186891 | H | H | H | H |
| SJ22186879 | H | H | H | H |
| SJ22186841 | H | H | H | H |
| SJ22186057 | H | H | H | H |
| SJ22186065 | H | H | H | H |
| SJ22186951 | H | H | H | H |
| SJ22186840 | A | A | A | A |
| SJ22186070 | A | A | A | A |

TABLE 20D

| Marker | S08118-1-Q1 | S08116-1-Q1 | S08114-1-Q1 | S08113-1-Q1 |
|---|---|---|---|---|
| Amplicon/Pos | PPO_Gm19_1566k4-1 | PPO_Gm19_1566k5-1 | PPO_Gm19_1571k3-1 | PPO_Gm19_1571k3-1 |
| Sample | | | | |
| SJ22185925 | B | B | — | — |
| SJ22186974 | — | B | — | — |
| SJ22185946 | B | B | — | — |
| SJ22186019 | — | B | B | B |
| SJ22186923 | B | B | B | B |
| SJ22185604 | H | H | — | — |
| SJ22186029 | H | H | — | — |
| SJ22186052 | — | H | — | — |
| SJ22185534 | A | A | — | — |
| SJ22185552 | A | A | — | — |
| SJ22186842 | A | A | — | — |
| SJ22186924 | A | A | — | — |
| SJ22186873 | A | A | — | — |
| SJ22186894 | A | A | A | A |
| SJ22185957 | A | A | A | A |
| SJ22185941 | A | A | A | A |
| SJ22186872 | A | A | — | — |
| SJ22185984 | A | A | A | A |
| SJ22186045 | B | B | B | B |
| SJ22186913 | B | B | B | B |
| SJ22186891 | H | H | H | H |
| SJ22186879 | H | H | H | H |
| SJ22186841 | H | H | — | — |
| SJ22186057 | H | H | H | H |
| SJ22186065 | H | H | H | H |
| SJ22186951 | H | H | H | H |
| SJ22186840 | A | A | A | A |
| SJ22186070 | A | A | A | A |

TABLE 20E

| Marker | S08101-1-Q1 | S08112-1-Q1 | S08108-1-Q1 | S08101-2-Q1 |
|---|---|---|---|---|
| Amplicon/Pos | PPO_Gm19_1586k1-1 | PPO_Gm19_1586k1-1 | PPO_Gm19_1586k2-1 | PPO_Gm19_1586k4-1 |
| Sample | | | | |
| SJ22185925 | B | B | B | B |
| SJ22186974 | B | B | B | B |
| SJ22185946 | B | B | B | B |
| SJ22186019 | B | B | B | B |
| SJ22186923 | B | B | B | B |
| SJ22185604 | H | H | H | H |
| SJ22186029 | H | H | H | H |
| SJ22186052 | H | H | H | H |
| SJ22185534 | A | A | A | A |
| SJ22185552 | A | A | A | A |
| SJ22186842 | A | A | A | A |
| SJ22186924 | A | A | A | A |
| SJ22186873 | A | A | A | A |
| SJ22186894 | A | A | A | A |
| SJ22185957 | A | A | A | A |
| SJ22185941 | A | A | A | A |
| SJ22186872 | A | A | A | A |
| SJ22185984 | A | A | A | A |
| SJ22186045 | — | B | B | B |
| SJ22186913 | — | B | B | B |
| SJ22186891 | — | H | H | H |
| SJ22186879 | — | H | H | H |
| SJ22186841 | — | H | H | H |
| SJ22186057 | — | H | H | H |
| SJ22186065 | — | H | H | H |
| SJ22186951 | — | H | H | H |
| SJ22186840 | — | A | A | A |
| SJ22186070 | — | A | A | A |

TABLE 20F

| Marker | S08101-1-Q1 | S08101-2-Q1 | S08101-3-Q1 | S08101-4-Q1 |
|---|---|---|---|---|
| Amplicon/Pos | PPO_Gm19_1586k4-1 | PPO_Gm19_1586k4-1 | PPO_Gm19_1586k4-1 | PPO_Gm19_1586k4-1 |
| Sample | | | | |
| SJ22185925 | B | — | B | B |
| SJ22186974 | B | — | B | B |
| SJ22185946 | B | — | B | B |
| SJ22186019 | B | B | B | B |
| SJ22186923 | B | B | B | B |
| SJ22185604 | H | — | H | H |
| SJ22186029 | H | — | H | H |
| SJ22186052 | H | — | H | H |
| SJ22185534 | A | — | A | A |
| SJ22185552 | A | — | A | A |
| SJ22186842 | A | — | A | A |
| SJ22186924 | A | — | A | A |
| SJ22186873 | A | — | A | A |
| SJ22186894 | A | A | A | A |
| SJ22185957 | A | A | A | A |
| SJ22185941 | A | A | A | A |
| SJ22186872 | A | — | A | A |
| SJ22185984 | A | A | A | A |
| SJ22186045 | — | B | B | B |
| SJ22186913 | — | B | B | B |
| SJ22186891 | — | H | H | H |
| SJ22186879 | — | H | H | H |
| SJ22186841 | — | H | H | H |
| SJ22186057 | — | H | H | H |
| SJ22186065 | — | H | H | H |
| SJ22186951 | — | H | H | H |
| SJ22186840 | — | A | A | A |
| SJ22186070 | — | A | A | A |

TABLE 20G

| Marker | S08105-1-Q1 | S08007-1-Q1 | S03859-1-A | S08010-1-Q1 |
|---|---|---|---|---|
| Amplicon/Pos | PPO_Gm19_1618k2-1 | PPO_Gm19_2089k3-1 | PPO_Gm19_1635140 | PPO_Gm19_2089k4-1 |
| Sample | | | | |
| SJ22185925 | B | — | B | A |
| SJ22186974 | B | — | B | A |
| SJ22185946 | B | — | B | A |
| SJ22186019 | H | H | H | H |
| SJ22186923 | B | B | B | B |
| SJ22185604 | B | — | B | B |
| SJ22186029 | H | — | H | B |
| SJ22186052 | H | — | H | H |
| SJ22185534 | A | — | A | B |
| SJ22185552 | A | — | A | B |
| SJ22186842 | A | — | A | B |
| SJ22186924 | A | — | A | B |
| SJ22186873 | A | — | A | B |
| SJ22186894 | B | B | B | B |
| SJ22185957 | A | B | A | B |
| SJ22185941 | H | H | H | H |
| SJ22186872 | A | — | A | B |
| SJ22185984 | A | A | A | A |
| SJ22186045 | B | B | — | B |
| SJ22186913 | B | B | — | B |
| SJ22186891 | H | A | — | A |
| SJ22186879 | H | B | — | B |
| SJ22186841 | H | A | — | A |
| SJ22186057 | H | A | — | A |
| SJ22186065 | H | H | — | A |
| SJ22186951 | H | H | — | A |
| SJ22186840 | A | A | — | A |
| SJ22186070 | A | H | — | H |

TABLE 20H

| Marker Amplicon/Pos | S08010-2-Q2 PPO_Gm19_2089k4-1 | Comment | Phenotype |
|---|---|---|---|
| SJ22185925 | A | | TOL |
| SJ22186974 | A | | TOL |
| SJ22185946 | H | | TOL |
| SJ22186019 | H | R Border | TOL |
| SJ22186923 | B | | TOL |
| SJ22185604 | B | | SEG |
| SJ22186029 | B | | SEG |
| SJ22186052 | H | L Border | SEG |
| SJ22185534 | B | | SUS |
| SJ22185552 | B | | SUS |
| SJ22186842 | B | | SUS |
| SJ22186924 | B | | SUS |
| SJ22186873 | B | | SUS |
| SJ22186894 | B | R Border | SUS |
| SJ22185957 | B | | SUS |
| SJ22185941 | H | R Border | SUS |
| SJ22186872 | B | | SUS |
| SJ22185984 | A | | SUS |
| SJ22186045 | B | | TOL |
| SJ22186913 | B | | TOL |
| SJ22186891 | A | | SEG |
| SJ22186879 | B | | SEG |
| SJ22186841 | A | | SEG |
| SJ22186057 | A | | SEG |
| SJ22186065 | A | | SEG |
| SJ22186951 | A | | SEG |
| SJ22186840 | A | | SUS |
| SJ22186070 | H | | SUS |

Tables 20I-20L. Fine-Mapping of the Herbicide Tolerance QTL Interval with Recombinants from the GEID4520632× GEID7589905 Population

TABLE 20I

| | | | Marker | | | | | |
|---|---|---|---|---|---|---|---|---|
| Sample | Comment | Phenotype | S04867-1-A | S08102-1-Q1 | S08103-1-Q1 | S08104-1-Q1 | S08115-2-Q1 | S08115-1-Q1 | S08117-1-Q1 |
| SP21669249 | R Border | TOL | H | B | B | B | B | — | B |
| SP21669332 | R Border | TOL | B | B | — | B | B | — | B |
| SP21669615 | R Border | TOL | B | — | B | B | B | — | B |
| SP21669616 | R Border | TOL | B | B | — | B | B/H | — | B |
| SP21669670 | R Border | TOL | H | B | B | B | — | — | B |
| SP21669503 | L Border | SEG | B | B | B | B | B | — | B |
| SP21669458 | R Border | SUS | A | A | A | A | A | — | A |
| SP21669760 | R Border | SUS | A | A | A | A | A | — | A |
| SP21669417 | L Border | SEG | — | — | A | A | — | A | A |
| SP21669560 | | SEG | — | — | B | B | — | H | H |
| SP21669331 | | SEG | — | — | H | H | — | H | H |

TABLE 20J

| Sample | Comment | Phenotype | Marker S08119-1-Q1 | S08118-1-Q1 | S08116-1-Q1 | S08114-1-Q1 | S08113-1-Q1 | S08101-1-Q1 | S08112-1-Q1 |
|---|---|---|---|---|---|---|---|---|---|
| SP21669249 | R Border | TOL | B | B | B | — | — | B | B |
| SP21669332 | R Border | TOL | B | B | B | — | — | B | B |
| SP21669615 | R Border | TOL | B | B | B | — | — | B | B |
| SP21669616 | R Border | TOL | B | B | B | — | — | B | B/H |
| SP21669670 | R Border | TOL | B | B | B | — | — | B | B |
| SP21669503 | L Border | SEG | H | H | H | — | — | H | H |
| SP21669458 | R Border | SUS | A | A | A | — | — | A | A |
| SP21669760 | R Border | SUS | A | A | A | — | — | A | A |
| SP21669417 | L Border | SEG | A | A | A | A | A | — | H |
| SP21669560 | | SEG | — | H | H | H | H | — | H |
| SP21669331 | | SEG | H | H | H | H | H | — | H |

TABLE 20K

| Sample | Comment | Phenotype | Marker S08108-1-Q1 | S08101-1-Q1 | S08101-2-Q1 | S08101-3-Q1 | S08101-4-Q1 | S08105-1-Q1 | S03859-1-A |
|---|---|---|---|---|---|---|---|---|---|
| SP21669249 | R Border | TOL | B | B | B | B | B | B | B |
| SP21669332 | R Border | TOL | B | B | B | B | — | B | B |
| SP21669615 | R Border | TOL | B | B | B | B | B | B | B |
| SP21669616 | R Border | TOL | B | B | B | B | B | B | B |
| SP21669670 | R Border | TOL | B | B | B | B | B | B | B |
| SP21669503 | L Border | SEG | H | H | H | H | H | H | H |
| SP21669458 | R Border | SUS | A | A | A | A | A | A | A |
| SP21669760 | R Border | SUS | A | A | A | A | A | A | A |
| SP21669417 | L Border | SEG | H | — | H | H | H | H | — |
| SP21669560 | | SEG | H | — | H | H | H | H | — |
| SP21669331 | | SEG | H | — | H | H | H | H | — |

TABLE 20L

| Sample | Comment | Marker Phenotype | S08007-1-Q1 | S08010-1-Q1 | S08010-2-Q2 |
|---|---|---|---|---|---|
| SP21669249 | R Border | TOL | — | H | H |
| SP21669332 | R Border | TOL | — | H | H |
| SP21669615 | R Border | TOL | — | B | B |
| SP21669616 | R Border | TOL | — | H | H |
| SP21669670 | R Border | TOL | — | B | B |
| SP21669503 | L Border | SEG | — | H | H |
| SP21669458 | R Border | SUS | — | H | H |
| SP21669760 | R Border | SUS | — | H | H |
| SP21669417 | L Border | SEG | H | H | H |
| SP21669560 | | SEG | H | — | H |
| SP21669331 | | SEG | A | A | A |

Example 8: SNP Haplotype Association Analysis

Association analysis of SNP haplotypes across the herbicide tolerance QTL region provides an independent method of validating the herbicide tolerance interval. From the panel of susceptible and tolerant lines used to identify SNPs for Taqman® probe development, 235 SNPs from 49 amplicons were identified in the vicinity of the closely linked marker S03859-1-A. The resulting SNP haplotype data was analyzed to identify an interval in which all of the haplotypes from the susceptible and tolerant lines co-segregated with each other (Table 21).

TABLE 21

SNP haplotype association analysis of the herbicide tolerance QTL interval. Perfect association between haplotype and phenotype between amplicons 1563k1 and 1618k2 defines the QTL interval

| GEID | Amplicon | 1563k1 | 1563k1 | 1563k1 | 1563k1 | 1618k2 | 1618k2 |
|---|---|---|---|---|---|---|---|
| 627002 | TOL (PPO) | G | G | A | C | * | C |
| 3911338 | TOL (PPO) | G | G | A | C | * | C |
| 1564727 | TOL (PPO) | G | G | A | C | * | C |
| 4230314 | TOL (PPO) | G | G | A | C | * | C |
| 4135359 | TOL (PPO) | G | G | A | C | * | C |
| 4611588 | TOL (PPO) | G | G | A | C | * | C |
| 1590166 | TOL (PPO) | G | G | A | C | * | C |
| 3395451 | TOL (PPO) | G | G | A | C | * | C |
| 2322432 | TOL (PPO) | G | G | A | C | * | C |
| 4520632 | TOL (PPO) | G | G | A | C | * | C |
| 632343 | TOL (PPO) | G | G | A | C | * | C |
| 1770139 | TOL (PPO) | G | G | A | C | * | C |
| 3587853 | TOL (PPO) | G | G | A | C | * | C |
| 4553991 | TOL (PPO) | G | G | A | C | * | C |
| 5183219 | TOL (PPO) | G | G | A | C | * | C |
| 2636517 | TOL (PPO) | G | G | A | C | * | C |
| 3495695 | TOL (PPO) | G | G | A | C | * | C |
| 1737165 | SUS (PPO) | A | * | G | T | A | A |
| 1653063 | SUS (PPO) |   |   |   |   | A | A |
| 4501774 | SUS (PPO) | A | * | G | T | A | A |
| 7589905 | SUS (PPO) | A | * | G | T | N | A |
| 4832982 | SUS (PPO) | A | * | G | T | N | A |
| 2839548 | SUS (PPO) | A | * | G | T |   |   |
| 3958440 | SUS (PPO) | A | * | G | T | A | A |
| 6116656 | SUS (PPO) | A | * | G | T | A | A |

Although it is difficult to definitively define the co-segregating region, it can conservatively be estimated to reside between amplicons PPO_Gm19_1563k1 and PPO_Gm19_1618k2-1. Within the borders defined by these loci, there are 38 SNP differences that are shared between all of the susceptible lines as compared to all the tolerant lines. This interval overlaps with the ~44 kb QTL interval identified by fine-mapping.

Example 9: QTL Analysis

The F2 population derived from GEID1653063× GEID6461257 consisting of 251 progeny and segregating for the herbicide tolerance trait was used for mapping. The trait has been previously mapped to LG-L. The population was screened with a total of 15 polymorphic markers from LG-L (Ch 19). Five of these 19 markers showed severe segregation distortion and were excluded in the mapping analysis. A significant QTL for herbicide tolerance was detected on the LG-L (LRS=364) which was closely linked with the PPO production marker S08101-2-Q1 and flanked by markers S04867-1-A (7.81 cM) and S03859-1-A (10.00 cM). The QTL explained around 76% of phenotypic variation.

Material and Methods

Population: An F2 mapping population GEID1653063/ GEID6461257 consisting of 251 F2 progeny was used. DNA extraction of the tissue was prepared using a citrate extraction protocol and quantified using the GW DNA quantification protocol.

Phenotype: The herbicide tolerance phenotypes were for each line were evaluated using chi-square analysis to establish a goodness to fit to the expected 1:2:1 genetic segregation ratio. The goodness of fit test indicated that the phenotypic data for the 251 progeny follows the expected 1:2:1 genetic ratio (p-value=0.769).

Genotype: PolyM was used to identify polymorphic markers between the two parents. A total of 15 polymorphic markers from LG-L were assayed. Allele nomenclature used were maternal alleles were assigned "A" and paternal alleles "B", and heterozygous "H". The 10 of 15 markers were linked together on LG-L with 5 markers showing severe segregation distortion in the population. The 5 markers showing severe segregation distortion were excluded for mapping analysis.

Linkage Analysis: Map Manager QTX.b20 (Manly et al. (2001) Mammalian Genome 12:930-932) was used to construct the linkage map and perform the QTL analysis. A 1000 permutation test was used to establish the threshold for statistical significance (LOD ratio statistic—LRS) to declare a putative QTL.

Map Manager parameters were set to:
1) Linkage Evaluation: Intercross
2) Search Criteria: P=1e-5
3) Map Function: Kosambi
4) Cross Type: Line Cross QTL Analysis Permutation Test: The thresholds at, 0.01 and 0.05 level based on a 1000 permutation test for herbicide tolerance trait are 7.0 and 17.3, respectively. The marker regression analysis showed that the QTL associated with herbicide tolerance could locate on the LG-L. Interval mapping showed a highly significant region on LG L (LRS=346). The QTL was closely linked with marker S08101-2-Q1 and flanked by markers S04867-1-A (7.81 cM) and S03859-1-A (10.00 cM). This region was estimated to explain ~76% of the phenotypic variation.

It will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

All publications referred to herein are incorporated by reference herein for the purpose cited to the same extent as if each was specifically and individually indicated to be incorporated by reference herein.

What is claimed is:

1. A method for selectively screening soybean plants for tolerance to one or more herbicides selected from the group consisting of a mesotrione herbicide and an isoxazole herbicide, the method comprising:
   (a) crossing a first soybean plant with a second soybean plant to form a soybean plant or soybean germ plasm population;
   (b) isolating nucleic acids from the soybean plant or soybean germplasm of the population;
   (c) detecting in the nucleic acids at least one allele of one or more marker loci associated with tolerance or improved tolerance to the one or more herbicides, wherein the one or more marker loci localize within a chromosome interval selected from the group consisting of:
      (i) the chromosomal interval flanked by and including markers S04867-1-A and S03859-1-A on linkage group L;
      (ii) the chromosomal interval flanked by and including markers S08110-1-Q1 and S08010-1-Q1 on linkage group L;
      (iii) the chromosomal interval flanked by and including markers S08117-1-Q1 and S08010-1-Q1 on linkage group L;
      (iv) the chromosomal interval flanked by and including markers S08110-1-Q1 and S08105-1-Q1 on linkage group L;
      (v) the chromosomal interval flanked by and including markers S08117-1-Q1 and S08105-1-Q1 on linkage group L; and
      (vi) the chromosomal interval flanked by and including markers S08113-1-Q1 and S08105-1-Q1 on linkage group L;
   (d) selecting the soybean plant or soybean germplasm comprising the at least one allele of one or more marker loci thereby selecting a plant with tolerance or improved tolerance to the one or more herbicides.

2. The method of claim 1, wherein the one or more marker loci are selected from the group consisting of SATT723, Sat_408, A169_1, EV2_1, Sle3_4s, BLT010_2, BLT007_1, SATT232, S04867-1-A, S08102-1-Q1, S08103-1-Q1, S08104-1-Q1, S08106-1-Q1, S08107-1-Q1, S08109-1-Q1, S08110-1-Q1, SO8111-1-Q1, S08115-2-Q1, S08117-1-Q1, S08119-1-Q1, S08116-1-Q1, S08112-1-Q1, S08108-1-Q1, S08101-4-Q1, S08101-1-Q1, S08101-2-Q1, S08101-3-Q1, SO8118-1-Q1, S08114-1-Q1, S08113-1-Q1, S03859-1-A, Sat_301, SATT446, SATT232, S08105-1-Q1, S08010-1-Q1, S08010-2-Q1, R176_1, JUBC090, SATT238, Sat_071, BLT039_1, Bng071_1, A264_1, RGA_7, RGA7, SATT523, Sat_134, S00224-1, S01659-1, LbA, i8_2, A450_2, A106_1, Sat_405, SATT143, B124_2, A459_1, SATT398, SATT694, Sat_195, Sat_388, SATT652, SATT711, Sat_187, SATT418, SATT278, Sat_397, Sat_191, Sat_320, 0109_1, A204_2, SATT497, G214_17, B164_1, G214_16, A023_1, SATT284, AW508247, SATT462, L050_7, E014_1, A071_5, B046_1, L1, and B162_2.

3. The method of claim 1, wherein the screening occurs as part of further breeding to improve a soybean variety's tolerance to one or more mesotrione herbicides or one or more isoxazole herbicides, and wherein the further breeding comprises crosses with other lines, crosses with hybrids, backcrossing, selfcrossing, or combinations thereof.

* * * * *

SEQUENCE LISTING

```
<160> NUMBER OF SEQ ID NOS: 121

<210> SEQ ID NO 1
<211> LENGTH: 30
<212> TYPE: DNA
<213> ORGANISM: Artificial Sequence
<220> FEATURE:
<223> OTHER INFORMATION: Primer/Probe Sequence

<400> SEQUENCE: 1
gagggctatg ttttcttctc cagatgtgag                              30

<210> SEQ ID NO 2
<211> LENGTH: 26
<212> TYPE: DNA
<213> ORGANISM: Artificial Sequence
<220> FEATURE:
<223> OTHER INFORMATION: Primer/Probe Sequence

<400> SEQUENCE: 2
aaggtcggct tggtggttaa aggcag                                  26

<210> SEQ ID NO 3
<211> LENGTH: 13
<212> TYPE: DNA
<213> ORGANISM: Artificial Sequence
<220> FEATURE:
<223> OTHER INFORMATION: Primer/Probe Sequence

<400> SEQUENCE: 3
tcatctgtga taa                                                13

<210> SEQ ID NO 4
<211> LENGTH: 13
<212> TYPE: DNA
<213> ORGANISM: Artificial Sequence
<220> FEATURE:
<223> OTHER INFORMATION: Primer/Probe Sequence

<400> SEQUENCE: 4
tcatgtgtga taa                                                13

<210> SEQ ID NO 5
<211> LENGTH: 13
<212> TYPE: DNA
<213> ORGANISM: Artificial Sequence
<220> FEATURE:
<223> OTHER INFORMATION: Primer/Probe Sequence
```

```
<400> SEQUENCE: 5
tcatctctga taa                                                          13

<210> SEQ ID NO 6
<211> LENGTH: 22
<212> TYPE: DNA
<213> ORGANISM: Artificial Sequence
<220> FEATURE:
<223> OTHER INFORMATION: Primer/Probe Sequence

<400> SEQUENCE: 6
ctggacctac ccgggatgaa aa                                                22

<210> SEQ ID NO 7
<211> LENGTH: 22
<212> TYPE: DNA
<213> ORGANISM: Artificial Sequence
<220> FEATURE:
<223> OTHER INFORMATION: Primer/Probe Sequence

<400> SEQUENCE: 7
tcttcctctc ccttcctctc gc                                                22

<210> SEQ ID NO 8
<211> LENGTH: 13
<212> TYPE: DNA
<213> ORGANISM: Artificial Sequence
<220> FEATURE:
<223> OTHER INFORMATION: Primer/Probe Sequence

<400> SEQUENCE: 8
cgcgactctc ctc                                                          13

<210> SEQ ID NO 9
<211> LENGTH: 13
<212> TYPE: DNA
<213> ORGANISM: Artificial Sequence
<220> FEATURE:
<223> OTHER INFORMATION: Primer/Probe Sequence

<400> SEQUENCE: 9
cgcgagtctc ctc                                                          13

<210> SEQ ID NO 10
<211> LENGTH: 27
<212> TYPE: DNA
<213> ORGANISM: Artificial Sequence
<220> FEATURE:
<223> OTHER INFORMATION: Primer/Probe Sequence

<400> SEQUENCE: 10
tcccaggtta gattttctga acgaaga                                           27

<210> SEQ ID NO 11
<211> LENGTH: 24
<212> TYPE: DNA
<213> ORGANISM: Artificial Sequence
<220> FEATURE:
<223> OTHER INFORMATION: Primer/Probe Sequence

<400> SEQUENCE: 11
catcagcaca aaagggcatc ctca                                              24

<210> SEQ ID NO 12
<211> LENGTH: 16
```

```
<212> TYPE: DNA
<213> ORGANISM: Artificial Sequence
<220> FEATURE:
<223> OTHER INFORMATION: Primer/Probe Sequence

<400> SEQUENCE: 12
cactccttaa ggtaat                                                    16

<210> SEQ ID NO 13
<211> LENGTH: 16
<212> TYPE: DNA
<213> ORGANISM: Artificial Sequence
<220> FEATURE:
<223> OTHER INFORMATION: Primer/Probe Sequence

<400> SEQUENCE: 13
cactccttaa gataat                                                    16

<210> SEQ ID NO 14
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 14
gttatcgtca ccaccaccaa                                                20

<210> SEQ ID NO 15
<211> LENGTH: 21
<212> TYPE: DNA
<213> ORGANISM: Artificial Sequence
<220> FEATURE:
<223> OTHER INFORMATION: Primer/Probe Sequence

<400> SEQUENCE: 15
cacaacacga gtagccgtag g                                              21

<210> SEQ ID NO 16
<211> LENGTH: 16
<212> TYPE: DNA
<213> ORGANISM: Artificial Sequence
<220> FEATURE:
<223> OTHER INFORMATION: Primer/Probe Sequence

<400> SEQUENCE: 16
aacggatcat cacaac                                                    16

<210> SEQ ID NO 17
<211> LENGTH: 15
<212> TYPE: DNA
<213> ORGANISM: Artificial Sequence
<220> FEATURE:
<223> OTHER INFORMATION: Primer/Probe Sequence

<400> SEQUENCE: 17
aacggctcat cacaa                                                     15

<210> SEQ ID NO 18
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 18
```
cgacaatggc ctttacacct                                              20

<210> SEQ ID NO 19
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 19
tcgatatgga cgaaggagga                                              20

<210> SEQ ID NO 20
<211> LENGTH: 16
<212> TYPE: DNA
<213> ORGANISM: Artificial Sequence
<220> FEATURE:
<223> OTHER INFORMATION: Primer/Probe Sequence

<400> SEQUENCE: 20 acaccattt tcatcc                                                   16

<210> SEQ ID NO 21
<211> LENGTH: 16
<212> TYPE: DNA
<213> ORGANISM: Artificial Sequence
<220> FEATURE:
<223> OTHER INFORMATION: Primer/Probe Sequence

<400> SEQUENCE: 21 acacccttt tcatcc                                                   16

<210> SEQ ID NO 22
<211> LENGTH: 22
<212> TYPE: DNA
<213> ORGANISM: Artificial Sequence
<220> FEATURE:
<223> OTHER INFORMATION: Primer/Probe Sequence

<400> SEQUENCE: 22
gcaatcacat ttgcattcct ta                                           22

<210> SEQ ID NO 23
<211> LENGTH: 21
<212> TYPE: DNA
<213> ORGANISM: Artificial Sequence
<220> FEATURE:
<223> OTHER INFORMATION: Primer/Probe Sequence

<400> SEQUENCE: 23
tctgaacgag ttgtgcaaga a                                            21

<210> SEQ ID NO 24
<211> LENGTH: 16
<212> TYPE: DNA
<213> ORGANISM: Artificial Sequence
<220> FEATURE:
<223> OTHER INFORMATION: Primer/Probe Sequence

<400> SEQUENCE: 24
actgctgctt tgtcta                                                  16

<210> SEQ ID NO 25
<211> LENGTH: 16
<212> TYPE: DNA
<213> ORGANISM: Artificial Sequence

```
<220> FEATURE:
<223> OTHER INFORMATION: Primer/Probe Sequence

<400> SEQUENCE: 25
ctactgctac tttgtc                                                        16

<210> SEQ ID NO 26
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 26
acctcgtatt ggtggtggtg                                                    20

<210> SEQ ID NO 27
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 27
gaatgttcag tgcgagcaac                                                    20

<210> SEQ ID NO 28
<211> LENGTH: 15
<212> TYPE: DNA
<213> ORGANISM: Artificial Sequence
<220> FEATURE:
<223> OTHER INFORMATION: Primer/Probe Sequence

<400> SEQUENCE: 28
acttccctcg tttcg                                                         15

<210> SEQ ID NO 29
<211> LENGTH: 14
<212> TYPE: DNA
<213> ORGANISM: Artificial Sequence
<220> FEATURE:
<223> OTHER INFORMATION: Primer/Probe Sequence

<400> SEQUENCE: 29
cttccctcat ttcg                                                          14

<210> SEQ ID NO 30
<211> LENGTH: 22
<212> TYPE: DNA
<213> ORGANISM: Artificial Sequence
<220> FEATURE:
<223> OTHER INFORMATION: Primer/Probe Sequence

<400> SEQUENCE: 30
caaaaggaaa gaagaaccgt gt                                                 22

<210> SEQ ID NO 31
<211> LENGTH: 21
<212> TYPE: DNA
<213> ORGANISM: Artificial Sequence
<220> FEATURE:
<223> OTHER INFORMATION: Primer/Probe Sequence

<400> SEQUENCE: 31
tccaacctat gtgttggtgt g                                                  21
```

```
<210> SEQ ID NO 32
<211> LENGTH: 17
<212> TYPE: DNA
<213> ORGANISM: Artificial Sequence
<220> FEATURE:
<223> OTHER INFORMATION: Primer/Probe Sequence

<400> SEQUENCE: 32
atgattgaag caggaaa                                                  17

<210> SEQ ID NO 33
<211> LENGTH: 18
<212> TYPE: DNA
<213> ORGANISM: Artificial Sequence
<220> FEATURE:
<223> OTHER INFORMATION: Primer/Probe Sequence

<400> SEQUENCE: 33
tcatgattga agcagcaa                                                 18

<210> SEQ ID NO 34
<211> LENGTH: 27
<212> TYPE: DNA
<213> ORGANISM: Artificial Sequence
<220> FEATURE:
<223> OTHER INFORMATION: Primer/Probe Sequence

<400> SEQUENCE: 34
ggagacttga cttaaagaga aagaaaa                                       27

<210> SEQ ID NO 35
<211> LENGTH: 26
<212> TYPE: DNA
<213> ORGANISM: Artificial Sequence
<220> FEATURE:
<223> OTHER INFORMATION: Primer/Probe Sequence

<400> SEQUENCE: 35
cggaaagaaa aacaatagat tgaatg                                        26

<210> SEQ ID NO 36
<211> LENGTH: 19
<212> TYPE: DNA
<213> ORGANISM: Artificial Sequence
<220> FEATURE:
<223> OTHER INFORMATION: Primer/Probe Sequence

<400> SEQUENCE: 36
cttgttctag actgatcat                                                19

<210> SEQ ID NO 37
<211> LENGTH: 16
<212> TYPE: DNA
<213> ORGANISM: Artificial Sequence
<220> FEATURE:
<223> OTHER INFORMATION: Primer/Probe Sequence

<400> SEQUENCE: 37
ctagactgat aattca                                                   16

<210> SEQ ID NO 38
<211> LENGTH: 26
<212> TYPE: DNA
<213> ORGANISM: Artificial Sequence
<220> FEATURE:
<223> OTHER INFORMATION: Primer/Probe Sequence
```

```
<400> SEQUENCE: 38
tcattcaaga ctacatgaaa gacaaa                                          26

<210> SEQ ID NO 39
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 39
caagggagag caatccttga                                                 20

<210> SEQ ID NO 40
<211> LENGTH: 16
<212> TYPE: DNA
<213> ORGANISM: Artificial Sequence
<220> FEATURE:
<223> OTHER INFORMATION: Primer/Probe Sequence

<400> SEQUENCE: 40
atagtctccc aaacac                                                     16

<210> SEQ ID NO 41
<211> LENGTH: 17
<212> TYPE: DNA
<213> ORGANISM: Artificial Sequence
<220> FEATURE:
<223> OTHER INFORMATION: Primer/Probe Sequence

<400> SEQUENCE: 41
atagtctctc aaacacc                                                    17

<210> SEQ ID NO 42
<211> LENGTH: 22
<212> TYPE: DNA
<213> ORGANISM: Artificial Sequence
<220> FEATURE:
<223> OTHER INFORMATION: Primer/Probe Sequence

<400> SEQUENCE: 42
gaaactttcc attttgccct tc                                              22

<210> SEQ ID NO 43
<211> LENGTH: 18
<212> TYPE: DNA
<213> ORGANISM: Artificial Sequence
<220> FEATURE:
<223> OTHER INFORMATION: Primer/Probe Sequence

<400> SEQUENCE: 43
agaacgcagg ggagaagc                                                   18

<210> SEQ ID NO 44
<211> LENGTH: 16
<212> TYPE: DNA
<213> ORGANISM: Artificial Sequence
<220> FEATURE:
<223> OTHER INFORMATION: Primer/Probe Sequence

<400> SEQUENCE: 44
cttcttccac tcttac                                                     16

<210> SEQ ID NO 45
```

```
<211> LENGTH: 17
<212> TYPE: DNA
<213> ORGANISM: Artificial Sequence
<220> FEATURE:
<223> OTHER INFORMATION: Primer/Probe Sequence

<400> SEQUENCE: 45
ccttcttaca ctcttac                                                    17

<210> SEQ ID NO 46
<211> LENGTH: 28
<212> TYPE: DNA
<213> ORGANISM: Artificial Sequence
<220> FEATURE:
<223> OTHER INFORMATION: Primer/Probe Sequence

<400> SEQUENCE: 46
tgatatgaca ctctactaag atgtgttg                                         28

<210> SEQ ID NO 47
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 47
tgattcatcc gcaaacttga                                                 20

<210> SEQ ID NO 48
<211> LENGTH: 17
<212> TYPE: DNA
<213> ORGANISM: Artificial Sequence
<220> FEATURE:
<223> OTHER INFORMATION: Primer/Probe Sequence

<400> SEQUENCE: 48
cactctccta tattgtc                                                    17

<210> SEQ ID NO 49
<211> LENGTH: 16
<212> TYPE: DNA
<213> ORGANISM: Artificial Sequence
<220> FEATURE:
<223> OTHER INFORMATION: Primer/Probe Sequence

<400> SEQUENCE: 49
ctctcctaca ttgtca                                                     16

<210> SEQ ID NO 50
<211> LENGTH: 22
<212> TYPE: DNA
<213> ORGANISM: Artificial Sequence
<220> FEATURE:
<223> OTHER INFORMATION: Primer/Probe Sequence

<400> SEQUENCE: 50
agatccttgt tccaaattcc aa                                              22

<210> SEQ ID NO 51
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 51
```

```
ccttggctta atgggtgtgt                                                    20

<210> SEQ ID NO 52
<211> LENGTH: 16
<212> TYPE: DNA
<213> ORGANISM: Artificial Sequence
<220> FEATURE:
<223> OTHER INFORMATION: Primer/Probe Sequence

<400> SEQUENCE: 52
ccaacacaat ctaact                                                        16

<210> SEQ ID NO 53
<211> LENGTH: 14
<212> TYPE: DNA
<213> ORGANISM: Artificial Sequence
<220> FEATURE:
<223> OTHER INFORMATION: Primer/Probe Sequence

<400> SEQUENCE: 53
ccaacacaat cgaa                                                          14

<210> SEQ ID NO 54
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 54
atggaggcaa gcttgtgttt                                                    20

<210> SEQ ID NO 55
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 55
catgctacca gcatctgcaa                                                    20

<210> SEQ ID NO 56
<211> LENGTH: 17
<212> TYPE: DNA
<213> ORGANISM: Artificial Sequence
<220> FEATURE:
<223> OTHER INFORMATION: Primer/Probe Sequence

<400> SEQUENCE: 56
cttcataaac gccaaag                                                       17

<210> SEQ ID NO 57
<211> LENGTH: 16
<212> TYPE: DNA
<213> ORGANISM: Artificial Sequence
<220> FEATURE:
<223> OTHER INFORMATION: Primer/Probe Sequence

<400> SEQUENCE: 57
cataaatgcc aaagca                                                        16

<210> SEQ ID NO 58
<211> LENGTH: 20
<212> TYPE: DNA
```

```
<213> ORGANISM: Artificial Sequence
<220> FEATURE:
<223> OTHER INFORMATION: Primer/Probe Sequence

<400> SEQUENCE: 58
aatgagcaag ggagaggaca                                               20

<210> SEQ ID NO 59
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 59
tcgccgctgc tatttaattt                                               20

<210> SEQ ID NO 60
<211> LENGTH: 18
<212> TYPE: DNA
<213> ORGANISM: Artificial Sequence
<220> FEATURE:
<223> OTHER INFORMATION: Primer/Probe Sequence

<400> SEQUENCE: 60
aagcactact ttcaattg                                                 18

<210> SEQ ID NO 61
<211> LENGTH: 14
<212> TYPE: DNA
<213> ORGANISM: Artificial Sequence
<220> FEATURE:
<223> OTHER INFORMATION: Primer/Probe Sequence

<400> SEQUENCE: 61
aagcaccact ttca                                                     14

<210> SEQ ID NO 62
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 62
agatgccttg ctcagtggac                                               20

<210> SEQ ID NO 63
<211> LENGTH: 22
<212> TYPE: DNA
<213> ORGANISM: Artificial Sequence
<220> FEATURE:
<223> OTHER INFORMATION: Primer/Probe Sequence

<400> SEQUENCE: 63
atgatgaatg tgttgagcca at                                            22

<210> SEQ ID NO 64
<211> LENGTH: 14
<212> TYPE: DNA
<213> ORGANISM: Artificial Sequence
<220> FEATURE:
<223> OTHER INFORMATION: Primer/Probe Sequence

<400> SEQUENCE: 64
ccccatcacc atac                                                     14
```

```
<210> SEQ ID NO 65
<211> LENGTH: 14
<212> TYPE: DNA
<213> ORGANISM: Artificial Sequence
<220> FEATURE:
<223> OTHER INFORMATION: Primer/Probe Sequence

<400> SEQUENCE: 65
accccaccac cata                                                         14

<210> SEQ ID NO 66
<211> LENGTH: 22
<212> TYPE: DNA
<213> ORGANISM: Artificial Sequence
<220> FEATURE:
<223> OTHER INFORMATION: Primer/Probe Sequence

<400> SEQUENCE: 66
agaaaccttc caaagctctt gg                                                22

<210> SEQ ID NO 67
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 67
tagggaggca cttgacaacc                                                   20

<210> SEQ ID NO 68
<211> LENGTH: 15
<212> TYPE: DNA
<213> ORGANISM: Artificial Sequence
<220> FEATURE:
<223> OTHER INFORMATION: Primer/Probe Sequence

<400> SEQUENCE: 68
caacatccga gtcca                                                        15

<210> SEQ ID NO 69
<211> LENGTH: 15
<212> TYPE: DNA
<213> ORGANISM: Artificial Sequence
<220> FEATURE:
<223> OTHER INFORMATION: Primer/Probe Sequence

<400> SEQUENCE: 69
caacatcaga gtcca                                                        15

<210> SEQ ID NO 70
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 70
ttttgacccc cagagagttg                                                   20

<210> SEQ ID NO 71
<211> LENGTH: 20
<212> TYPE: DNA
<213> ORGANISM: Artificial Sequence
<220> FEATURE:
```

```
<223> OTHER INFORMATION: Primer/Probe Sequence

<400> SEQUENCE: 71
ttgcaagcct aaaggatggt                                              20

<210> SEQ ID NO 72
<211> LENGTH: 19
<212> TYPE: DNA
<213> ORGANISM: Artificial Sequence
<220> FEATURE:
<223> OTHER INFORMATION: Primer/Probe Sequence

<400> SEQUENCE: 72
ctatctctac acgatgtgt                                               19

<210> SEQ ID NO 73
<211> LENGTH: 16
<212> TYPE: DNA
<213> ORGANISM: Artificial Sequence
<220> FEATURE:
<223> OTHER INFORMATION: Primer/Probe Sequence

<400> SEQUENCE: 73
ctatctccac acgatg                                                  16

<210> SEQ ID NO 74
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 74
tcccacttga tcttgcagaa                                              20

<210> SEQ ID NO 75
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 75
tacggtgggt ggattattcg                                              20

<210> SEQ ID NO 76
<211> LENGTH: 15
<212> TYPE: DNA
<213> ORGANISM: Artificial Sequence
<220> FEATURE:
<223> OTHER INFORMATION: Primer/Probe Sequence

<400> SEQUENCE: 76
cctccaatgg catac                                                   15

<210> SEQ ID NO 77
<211> LENGTH: 17
<212> TYPE: DNA
<213> ORGANISM: Artificial Sequence
<220> FEATURE:
<223> OTHER INFORMATION: Primer/Probe Sequence

<400> SEQUENCE: 77
cctccaatag catacat                                                 17
```

```
<210> SEQ ID NO 78
<211> LENGTH: 22
<212> TYPE: DNA
<213> ORGANISM: Artificial Sequence
<220> FEATURE:
<223> OTHER INFORMATION: Primer/Probe Sequence

<400> SEQUENCE: 78
agaaaagcag cagaaagagg ac                                              22

<210> SEQ ID NO 79
<211> LENGTH: 22
<212> TYPE: DNA
<213> ORGANISM: Artificial Sequence
<220> FEATURE:
<223> OTHER INFORMATION: Primer/Probe Sequence

<400> SEQUENCE: 79
cttcatgaat cccaacatca ga                                              22

<210> SEQ ID NO 80
<211> LENGTH: 17
<212> TYPE: DNA
<213> ORGANISM: Artificial Sequence
<220> FEATURE:
<223> OTHER INFORMATION: Primer/Probe Sequence

<400> SEQUENCE: 80
ctctaattcc acatctg                                                    17

<210> SEQ ID NO 81
<211> LENGTH: 18
<212> TYPE: DNA
<213> ORGANISM: Artificial Sequence
<220> FEATURE:
<223> OTHER INFORMATION: Primer/Probe Sequence

<400> SEQUENCE: 81
cctctaattt cacatctg                                                   18

<210> SEQ ID NO 82
<211> LENGTH: 22
<212> TYPE: DNA
<213> ORGANISM: Artificial Sequence
<220> FEATURE:
<223> OTHER INFORMATION: Primer/Probe Sequence

<400> SEQUENCE: 82
tcaaaccatt ttgtttccca gt                                              22

<210> SEQ ID NO 83
<211> LENGTH: 21
<212> TYPE: DNA
<213> ORGANISM: Artificial Sequence
<220> FEATURE:
<223> OTHER INFORMATION: Primer/Probe Sequence

<400> SEQUENCE: 83
tgctagcctt tgatacccaa c                                               21

<210> SEQ ID NO 84
<211> LENGTH: 16
<212> TYPE: DNA
<213> ORGANISM: Artificial Sequence
<220> FEATURE:
<223> OTHER INFORMATION: Primer/Probe Sequence
```

```
<400> SEQUENCE: 84
ttgcattgta ttctct                                                    16

<210> SEQ ID NO 85
<211> LENGTH: 15
<212> TYPE: DNA
<213> ORGANISM: Artificial Sequence
<220> FEATURE:
<223> OTHER INFORMATION: Primer/Probe Sequence

<400> SEQUENCE: 85
ttgcattgta ttttc                                                     15

<210> SEQ ID NO 86
<211> LENGTH: 21
<212> TYPE: DNA
<213> ORGANISM: Artificial Sequence
<220> FEATURE:
<223> OTHER INFORMATION: Primer/Probe Sequence

<400> SEQUENCE: 86
gtctcaggca gtgaatctgc t                                              21

<210> SEQ ID NO 87
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 87
cagccttacc atcaacatcg                                                20

<210> SEQ ID NO 88
<211> LENGTH: 13
<212> TYPE: DNA
<213> ORGANISM: Artificial Sequence
<220> FEATURE:
<223> OTHER INFORMATION: Primer/Probe Sequence

<400> SEQUENCE: 88
ttccgtgaag atc                                                       13

<210> SEQ ID NO 89
<211> LENGTH: 15
<212> TYPE: DNA
<213> ORGANISM: Artificial Sequence
<220> FEATURE:
<223> OTHER INFORMATION: Primer/Probe Sequence

<400> SEQUENCE: 89
atgcttccgc gaaga                                                     15

<210> SEQ ID NO 90
<211> LENGTH: 26
<212> TYPE: DNA
<213> ORGANISM: Artificial Sequence
<220> FEATURE:
<223> OTHER INFORMATION: Primer/Probe Sequence

<400> SEQUENCE: 90
ggtagcagtt actttgtgat gtaagc                                         26

<210> SEQ ID NO 91
<211> LENGTH: 22
```

```
<212> TYPE: DNA
<213> ORGANISM: Artificial Sequence
<220> FEATURE:
<223> OTHER INFORMATION: Primer/Probe Sequence

<400> SEQUENCE: 91
catgcaataa aatccaaaac ca                                         22

<210> SEQ ID NO 92
<211> LENGTH: 17
<212> TYPE: DNA
<213> ORGANISM: Artificial Sequence
<220> FEATURE:
<223> OTHER INFORMATION: Primer/Probe Sequence

<400> SEQUENCE: 92
tactgatcac aggttat                                               17

<210> SEQ ID NO 93
<211> LENGTH: 17
<212> TYPE: DNA
<213> ORGANISM: Artificial Sequence
<220> FEATURE:
<223> OTHER INFORMATION: Primer/Probe Sequence

<400> SEQUENCE: 93
tactgaccac aggttat                                               17

<210> SEQ ID NO 94
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 94
ttgctttgga aaggactcca                                            20

<210> SEQ ID NO 95
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 95
cctcatcaac tcctgctgct                                            20

<210> SEQ ID NO 96
<211> LENGTH: 14
<212> TYPE: DNA
<213> ORGANISM: Artificial Sequence
<220> FEATURE:
<223> OTHER INFORMATION: Primer/Probe Sequence

<400> SEQUENCE: 96
ctcggtgctg tttt                                                  14

<210> SEQ ID NO 97
<211> LENGTH: 14
<212> TYPE: DNA
<213> ORGANISM: Artificial Sequence
<220> FEATURE:
<223> OTHER INFORMATION: Primer/Probe Sequence

<400> SEQUENCE: 97
```
ctcggtgctg tctt                                              14

<210> SEQ ID NO 98
<211> LENGTH: 23
<212> TYPE: DNA
<213> ORGANISM: Artificial Sequence
<220> FEATURE:
<223> OTHER INFORMATION: Primer/Probe Sequence

<400> SEQUENCE: 98
gaaaccaatt ttgatgtgaa gga                                    23

<210> SEQ ID NO 99
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 99
aagtgagagg ggtgcaaaga                                        20

<210> SEQ ID NO 100
<211> LENGTH: 14
<212> TYPE: DNA
<213> ORGANISM: Artificial Sequence
<220> FEATURE:
<223> OTHER INFORMATION: Primer/Probe Sequence

<400> SEQUENCE: 100
cagccctatc tcac                                              14

<210> SEQ ID NO 101
<211> LENGTH: 14
<212> TYPE: DNA
<213> ORGANISM: Artificial Sequence
<220> FEATURE:
<223> OTHER INFORMATION: Primer/Probe Sequence

<400> SEQUENCE: 101
agccctgtct cact                                              14

<210> SEQ ID NO 102
<211> LENGTH: 21
<212> TYPE: DNA
<213> ORGANISM: Artificial Sequence
<220> FEATURE:
<223> OTHER INFORMATION: Primer/Probe Sequence

<400> SEQUENCE: 102
gcaaatgaga aggctgaagc t                                      21

<210> SEQ ID NO 103
<211> LENGTH: 19
<212> TYPE: DNA
<213> ORGANISM: Artificial Sequence
<220> FEATURE:
<223> OTHER INFORMATION: Primer/Probe Sequence

<400> SEQUENCE: 103
gctgtccctc agtccatcc                                         19

<210> SEQ ID NO 104
<211> LENGTH: 15
<212> TYPE: DNA
<213> ORGANISM: Artificial Sequence
<220> FEATURE:
<223> OTHER INFORMATION: Primer/Probe Sequence

<400> SEQUENCE: 104
cggtatcgct cgtca        15

<210> SEQ ID NO 105
<211> LENGTH: 15
<212> TYPE: DNA
<213> ORGANISM: Artificial Sequence
<220> FEATURE:
<223> OTHER INFORMATION: Primer/Probe Sequence

<400> SEQUENCE: 105
tatcgctcgc caacg        15

<210> SEQ ID NO 106
<211> LENGTH: 23
<212> TYPE: DNA
<213> ORGANISM: Artificial Sequence
<220> FEATURE:
<223> OTHER INFORMATION: Primer/Probe Sequence

<400> SEQUENCE: 106
atccacttgc aagataggac act        23

<210> SEQ ID NO 107
<211> LENGTH: 26
<212> TYPE: DNA
<213> ORGANISM: Artificial Sequence
<220> FEATURE:
<223> OTHER INFORMATION: Primer/Probe Sequence

<400> SEQUENCE: 107
gtgtaagtac tgatgtgcag ttttga        26

<210> SEQ ID NO 108
<211> LENGTH: 19
<212> TYPE: DNA
<213> ORGANISM: Artificial Sequence
<220> FEATURE:
<223> OTHER INFORMATION: Primer/Probe Sequence

<400> SEQUENCE: 108
cttgacatta agactatcc        19

<210> SEQ ID NO 109
<211> LENGTH: 19
<212> TYPE: DNA
<213> ORGANISM: Artificial Sequence
<220> FEATURE:
<223> OTHER INFORMATION: Primer/Probe Sequence

<400> SEQUENCE: 109
agactaatcc ttaaacaag        19

<210> SEQ ID NO 110
<211> LENGTH: 27
<212> TYPE: DNA
<213> ORGANISM: Artificial Sequence
<220> FEATURE:
<223> OTHER INFORMATION: Primer/Probe Sequence

<400> SEQUENCE: 110
tcaacaggtt atgaatatac aggtcaa        27

```
<210> SEQ ID NO 111
<211> LENGTH: 22
<212> TYPE: DNA
<213> ORGANISM: Artificial Sequence
<220> FEATURE:
<223> OTHER INFORMATION: Primer/Probe Sequence

<400> SEQUENCE: 111
catcaccaat tgtttggagt tc                                              22

<210> SEQ ID NO 112
<211> LENGTH: 19
<212> TYPE: DNA
<213> ORGANISM: Artificial Sequence
<220> FEATURE:
<223> OTHER INFORMATION: Primer/Probe Sequence

<400> SEQUENCE: 112
ctattactct ccgttattt                                                  19

<210> SEQ ID NO 113
<211> LENGTH: 18
<212> TYPE: DNA
<213> ORGANISM: Artificial Sequence
<220> FEATURE:
<223> OTHER INFORMATION: Primer/Probe Sequence

<400> SEQUENCE: 113
ctattactcc ccgttatt                                                   18

<210> SEQ ID NO 114
<211> LENGTH: 18
<212> TYPE: DNA
<213> ORGANISM: Artificial Sequence
<220> FEATURE:
<223> OTHER INFORMATION: Primer/Probe Sequence

<400> SEQUENCE: 114
ttgttgaatg ggggcact                                                   18

<210> SEQ ID NO 115
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 115
ctcgagcaaa tctcgatggt                                                 20

<210> SEQ ID NO 116
<211> LENGTH: 17
<212> TYPE: DNA
<213> ORGANISM: Artificial Sequence
<220> FEATURE:
<223> OTHER INFORMATION: Primer/Probe Sequence

<400> SEQUENCE: 116
ttgaatgctt actctct                                                    17

<210> SEQ ID NO 117
<211> LENGTH: 19
<212> TYPE: DNA
<213> ORGANISM: Artificial Sequence
<220> FEATURE:
<223> OTHER INFORMATION: Primer/Probe Sequence
```

```
<400> SEQUENCE: 117
ttgaatgttt actctcttt                                                    19

<210> SEQ ID NO 118
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 118
ctgtggagga ggagcttgag                                                   20

<210> SEQ ID NO 119
<211> LENGTH: 22
<212> TYPE: DNA
<213> ORGANISM: Artificial Sequence
<220> FEATURE:
<223> OTHER INFORMATION: Primer/Probe Sequence

<400> SEQUENCE: 119
acaagtcaca accgtcaatg at                                                22

<210> SEQ ID NO 120
<211> LENGTH: 19
<212> TYPE: DNA
<213> ORGANISM: Artificial Sequence
<220> FEATURE:
<223> OTHER INFORMATION: Primer/Probe Sequence

<400> SEQUENCE: 120
agtctttgtt ttctctttt                                                    19

<210> SEQ ID NO 121
<211> LENGTH: 19
<212> TYPE: DNA
<213> ORGANISM: Artificial Sequence
<220> FEATURE:
<223> OTHER INFORMATION: Primer/Probe Sequence

<400> SEQUENCE: 121
agtctttgtt ttctctctt                                                    19
```